United States Patent
Kaspar et al.

(10) Patent No.: US 9,725,719 B2
(45) Date of Patent: Aug. 8, 2017

(54) COMPOSITIONS AND METHODS FOR INHIBITING NF-κB AND SOD-1 TO TREAT AMYOTROPHIC LATERAL SCLEROSIS

(71) Applicant: THE RESEARCH INSTITUTE AT NATIONWIDE CHILDREN'S HOSPITAL, Columbus, OH (US)

(72) Inventors: Brian K. Kaspar, New Albany, OH (US); Ashley E. Frakes, Columbus, OH (US)

(73) Assignee: THE RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 0 days.

(21) Appl. No.: 15/034,489

(22) PCT Filed: Nov. 4, 2014

(86) PCT No.: PCT/US2014/063890
§ 371 (c)(1),
(2) Date: May 4, 2016

(87) PCT Pub. No.: WO2015/069647
PCT Pub. Date: May 14, 2015

(65) Prior Publication Data
US 2016/0289676 A1   Oct. 6, 2016

Related U.S. Application Data

(60) Provisional application No. 61/900,105, filed on Nov. 5, 2013.

(51) Int. Cl.
*A61K 48/00*   (2006.01)
*C12N 15/11*   (2006.01)
(Continued)

(52) U.S. Cl.
CPC ........... *C12N 15/113* (2013.01); *A61K 48/00* (2013.01); *C12N 15/86* (2013.01);
(Continued)

(58) Field of Classification Search
USPC ........................................... 514/44, 2
See application file for complete search history.

(56) References Cited

U.S. PATENT DOCUMENTS

| 5,173,414 A | 12/1992 | Lebkowski et al. |
| 5,658,776 A | 8/1997 | Flotte et al. |

(Continued)

FOREIGN PATENT DOCUMENTS

| AU | 2001294088 | 9/2006 |
| AU | 2001294088 B2 | 9/2006 |

(Continued)

OTHER PUBLICATIONS

Frakes et al. (Neuron. Mar. 5, 2014; 81(5): 1009-1023).*
(Continued)

*Primary Examiner* — Terra C Gibbs
(74) *Attorney, Agent, or Firm* — Barnes & Thornburg LLP; Gregory H. Zayia

(57) ABSTRACT

The invention relates to pharmaceutical compositions, kits, methods, and uses for the treatment of amyotrophic lateral sclerosis. In particular, the invention relates to compositions, kits, methods, and uses for the treatment of amyotrophic lateral sclerosis by inhibiting NF-κB in microglia or macrophages and by inhibiting motor neuron death. The invention further relates to compositions, kits, methods, and uses for the treatment of amyotrophic lateral sclerosis by inhibiting NF-κB in microglia in combination with inhibiting SOD-1 in astrocytes. The invention also relates to a method for inhibiting the expression or the activity of NF-κB in microglia or macrophages to inhibit motor neuron death, (Continued)

alone or in combination with inhibiting SOD-1 expression in astrocytes.

10 Claims, 38 Drawing Sheets

(51) Int. Cl.
 C07H 21/02 (2006.01)
 C07H 21/04 (2006.01)
 C12N 15/113 (2010.01)
 C12N 15/86 (2006.01)
(52) U.S. Cl.
 CPC .... C12N 2310/14 (2013.01); C12N 2310/531 (2013.01); C12N 2750/14141 (2013.01); C12N 2750/14143 (2013.01)

(56) References Cited

U.S. PATENT DOCUMENTS

| | | | |
|---|---|---|---|
| 5,786,211 | A | 7/1998 | Johnson |
| 5,871,982 | A | 2/1999 | Wilson et al. |
| 6,258,595 | B1 | 7/2001 | Gao et al. |
| 6,566,118 | B1 | 5/2003 | Atkinson et al. |
| 6,723,315 | B1 | 4/2004 | Mallet et al. |
| 2004/0009479 | A1 | 1/2004 | Wohlgemuth et al. |
| 2005/0053922 | A1 | 3/2005 | Schaffer et al. |
| 2009/0202490 | A1 | 8/2009 | Schaffer et al. |
| 2010/0081705 | A1 | 4/2010 | Bennett et al. |
| 2010/0152053 | A1 | 6/2010 | Russwurm |
| 2011/0053861 | A1 | 3/2011 | Xie et al. |
| 2012/0177605 | A1 | 7/2012 | Kaspar et al. |

FOREIGN PATENT DOCUMENTS

| | | |
|---|---|---|
| KR | 2013-0107947 | 10/2013 |
| WO | 95/13365 A1 | 5/1995 |
| WO | 95/13392 A1 | 5/1995 |
| WO | 96/17947 A1 | 6/1996 |
| WO | 97/06243 A1 | 2/1997 |
| WO | 97/08298 A1 | 3/1997 |
| WO | 97/09441 A2 | 3/1997 |
| WO | 97/21825 A1 | 6/1997 |
| WO | 98/09657 A2 | 3/1998 |
| WO | 98/18600 A1 | 5/1998 |
| WO | 99/11764 A2 | 3/1999 |
| WO | 0183692 A2 | 11/2001 |
| WO | 2005096781 A2 | 10/2005 |
| WO | 2006066203 A2 | 6/2006 |
| WO | 2009013290 A1 | 1/2009 |
| WO | 2009043936 A1 | 4/2009 |
| WO | 2009102427 A2 | 8/2009 |
| WO | WO 2009/102427 | 8/2009 |
| WO | 2010071832 A1 | 6/2010 |
| WO | 2011133890 A1 | 10/2011 |
| WO | 2012058220 A2 | 5/2012 |
| WO | 2012121403 A1 | 9/2012 |
| WO | WO 2012/121403 | 9/2012 |
| WO | 2013078316 A1 | 5/2013 |
| WO | 2013123503 A1 | 8/2013 |
| WO | WO 2013/123503 | 8/2013 |
| WO | 2014052753 A1 | 4/2014 |
| WO | 2014071219 A1 | 5/2014 |
| WO | 2015031392 A1 | 3/2015 |

OTHER PUBLICATIONS

Crosio et al., "Astroglial Inhibition of NF-κB Does Not Ameliorate Disease Onset and Progression in a Mouse Model for Amyotrophic Lateral Sclerosis (ALS)," *PLoS ONE*, 6(3): E17187 (Mar. 18, 2011).
Frakes, "NF-κB Activation in Microglia Induces Motor Neuron Death in Amyotrophic Lateral Sclerosis," Abstract, *27th Hayes Graduate Research Forum*, (Feb. 18, 2015).

Haidet-Phillips et al., "Astrocytes From Familial and Sporadic ALS Patients Are Toxic to Motor Neurons," *Nature Biotechnology*, 29(9): 824-828 (Aug. 10, 2011).
Sommer et al., "Quantification of Adeno-Associated Virus Particles and Empty Capsids by Optical Density Measurement,." *Molecular Therapeutics.*, 7(1): 122-128 (2003).
International Search Report & Written Opinion for International Application No. PCT/US2014/063890 Dated Mar. 25, 2015 (27 pages).
Vallabhupurapu and Karin, "Regulation and Function of NF-κB Transcription Factors in the Immune System", Annu. Rev. Immunol. 2009, 27: 693-733.
Kigerl et al., "Identification of Two Distinct Macrophage Subsets with Divergent Effects Causing either Neurotoxicity or Regeneration in the Injured Mouse Spinal Cord", The Journal of Neuroscience, Oct. 28, 2009, 29 (43):13435-13444.
Beers et al, "Neuroinflammation modulates distinct regional and temporal clinical responses in ALS mice", Brain, Behavior, and Immunity, 25 (2011), pp. 1025-1035.
Norden and Godbout, "Review: Microglia of the aged brain: primed to be activated and resistant to regulation", Neuropathology and Applied Neurobiology, 2013, 39, 19-14.
Dahlman & Guttridge, "Detection of NF-κB Activity in Skeletal Muscle Cells by Electrophoretic Mobility Shift Analysis", Myogenesis: Methods and Protocols, Methods in Molecular Biology, vol. 798, 2012.
Foust et al, "Intravascular AAV0 preferentially targets neonatal neurons and adult astrocytes", Nat. Biotechnol. 27, 59-65, 2008.
Foust et al, "Rescue of the spinal muscular atrophy phenotype in a mouse model by early postnatal delivery of SMN", Nature Biotechnology, vol. 28, No. 3, Mar. 2010.
Noble and Mayer-Proschel, "Culture of astrocytes, oligodendrocytes, and O-2A progenitor cells", MIT Press, Cambridge,1998. Book Reference available upon specific request from Examiner.
Henry et al., "Peripheral lipopolysaccharide (LPS) challenge promotes microglial hyperactivity in aged mice that is associated with exaggerated induction of both pro-inflammatory IL-1beta and anti-inflammatory IL-10 cytokines", Brain, Behavior, and Immunity, 23 (2009), pp. 309-317.
Frakes, A., NF-KB Activation in Microglia Induces motor Neuro Death in Amyotrophic Lateral Sclerosis, 27th Hayes Graduate Research Forum presentation, Mar. 2013.
Sommer et al, Quanitifcation of Adeno-Associated Virus partciles and Empty Capsids by Optical Density Measurement, Mol Therapeutics, (2003), 7(1): 122-128.
PCT International Search Report/Written Opinion for PCT/US2014/063890, completed on Feb. 20, 2015.
Frakes, A.E., et al. Microglia induce motor neuron death via the classical NFkappaB pathway in amyotrophic lateral sclerosis. Neuron, 81, 1009-1023 (2014).
Meyer, K., et al. Direct conversion of patient fibroblasts demonstrates non-cell autonomous toxicity of astrocytes to motor neurons in familial and sporadic ALS. Proc Natl Acad Sci U S A, 111, 829-832 (2014).
Hester, M.E., et al. Two factor reprogramming of human neural stem cells into pluripotency. PLoS One, 4, e7044 (2009).
Kim, J.B., et al. Pluripotent stem cells induced from adult neural stem cells by reprogramming with two factors. Nature, 454, 646-650 (2008).
Kaech, S. & Banker, G. Culturing hippocampal neurons. Nat Protoc, 1, 2406-2415 (2006).
McConnell, M.J., Huang, Y.H., Datwani, A. & Shatz, C.J. H2-K(b) and H2-D(b) regulate cerebellar long-term depression and limit motor learning. Proc Natl Acad Sci U S A, 106, 6784-6789 (2009).
Syken, J. & Shatz, C.J. Expression of T cell receptor beta locus in central nervous system neurons. Proc Natl Acad Sci U S A, 100, 13048-13053 (2003).
Nardo, G., et al. Transcriptomic indices of fast and slow disease progression in two mouse models of amyotrophic lateral sclerosis. Brain 136, 3305-3332 (2013).

(56) References Cited

OTHER PUBLICATIONS

Thams, S., et al. Classical major histocompatibility complex class I molecules in motoneurons: new actors at the neuromuscular junction. J Neurosci 29, 13503-13515 (2009).
Dodge, J.C., et al. Delivery of AAV-IGF-1 to the CNS extends survival in ALS mice through modification of aberrant glial cell activity. Mol Ther 16, 1056-1064 (2008).
Re, D.B., et al. Necroptosis drives motor neuron death in models of both sporadic and familial ALS. Neuron 81, 1001-1008 (2014).
Goodridge, J.P., Burian, A., Lee, N. & Geraghty, D.E. HLA-F and MHC class I open conformers are ligands for NK cell Ig-like receptors. J Immunol 191, 3553-3562 (2013).
PCT International Search Report/Written Opinion for PCT/US2014/052753, completed on Nov. 24, 2014.
Charcot, "Lectures on the diseases of the nervous system", 1989. [submitted in two parts].
Kaplitt et al, Lancet 369: 2097-2105, 2007.
Marks et al, "Safety and tolerability of intraputaminal delivery of CERE-120 (adeno-associated virus serotype 2-neurturin) to patients with idiopathic Parkinson's disease: an open-label, phase I trial", Lancet Neurol 7: 400-408 , 2008.
Worgall et al, Hum Gen Ther, 2008.
Srivastava et al, J. Virol, 45: 555-564, (1983).
Ruffing et al, J Gen Virol, 75: 3385-3392 (1994).
Pacak et al, Circ Res, 99(4): 3-9 (1006).
Wang et al, Nature Biotech, 23(3), 321-328, (2005).
Grimm et al, Adeno-associated virus vectors for short hairpin RNA Expression, Methods in Enzymology, Academic Press, US, vol. 392, (2005), pp. 381-405. Book Reference.
Machida et al, Intraperitoneal administration of AAV9-shRNA inhibits target gene expression in the forsal root ganglia of neonatal mice, Molecular Pain, Biomed Central, 9(1): 36, (2013).
Ding et al, Selective siliencing by RNAi of a dominant allele that causes amyotrophic lateral sclerosis, Aging Cell, Blackwell Publichsing, vol. 2, pp. 209-217, (2003).
Musatov et al, RNAi-mediated silencing of estrogen receptor in ventromedial nucleus of hypothalamus abolishes female sexual behaviors, PNAS, 103(27): pp. 10456-10460, (2006).
Muzyczka, Current Topics in Microbiology and Immunology, 158: 97-129(1992).
Gao et al., J. Virol., 78: 6381-6388 (2004).
De, B.P., et al., "High Levels of Persistent Expression of alpha1-Antirypsin Mediated by the Nonhuman Primate Serotype rh. 10 Adeno-associated Virus Despite Preexisting Immunity to Common Human Adeno-associated Viruses", Mol. Ther., 13( 1): 67-76 (2006).
Mori et al., "Two Novel adeno-associated viruses from cynomolgus monkey: pseudotyping characterization of capsid protein", Virology, 330(2): 375-383 (2004).
Samulski et al., 1982, Proc. Natl. Acad. S6. USA, 79:2077-2081.
Laughlin et al., 1983, Gene, 23:65-73.
Senapathy & Carter, 1984, J. Biol. Chem., 259:4661-4666.
Carter, 1992, Current Opinions in Biotechnology, 533-539.
Tratschin et al., Mol. Cell. Biol. Oct. 1984, vol. 4, No. 10, 2072-2081.
Hermonat et al., Proc. Natl. Acad. Sci. USA, 81:6466 (1984).
Tratschin et al., Mol. Cell. Biol. 5:3251 (1985).
McLaughlin et al., J. Virol., 62:1963 (1988).
Lebkowski et al., 1988 Mol. Cell. Biol., 7:349 (1988).
Samulski et al., "Helper-Free Stocks of Recombinant Adeno-Associated Viruses: Normal Integration Does Not Require Viral Gene Expression", (1989, J. Virol., 63:3822-3828).
Perrin et al. (1995) Vaccine 13:1244-1250.
Paul et al. (1993) Human Gene Therapy 4:609-615.
Clark et al., "A stable cell line carrying adenovirus-inducible rep and cap genes allows for infectivity titration of adeno-associated virus vectors", (1996) Gene Therapy 3:1124-1132.
Clark el al., Hum. Gene Ther., 10(6): 1031-1039 (1999).
Schenpp and Clark, "Highly Purified Recombinant Adeno-Associated Virus Vectors", Methods Mol. Med.., 69: 427-443 (2002).

Da Cruz, S. & Cleveland, D.W. Understanding the role of TDP-43 and FUS/TLS in ALS and beyond. Curr Opin Neurobiol 21, 904-919 (2011).
Rosen, D.R. et al. Mutations in Cu/Zn superoxide dismutase gene are associated with familial amyotrophic lateral sclerosis. Nature 362, 59-62 (1993).
Ilieva, H., Polymenidou, M. & Cleveland, D.W. Non-cell autonomous toxicity in neurodegenerative disorders: ALS and beyond. The Journal of cell biology 187, 761-772 (2009).
Chattopadhyay, M. & Valentine, J.S. Aggregation of copper-zinc superoxide dismutase in familial and sporadic ALS. Antioxidants & redox signaling 11, 1603-1614 (2009).
Prudencio, M., Hart, P.J., Borchelt, D.R. & Andersen, P.M. Variation in aggregation propensities among ALS-associated variants of SOD1: correlation to human disease. Human molecular genetics 18, 3217-3226 (2009).
Boillee, S. et al. Onset and progression in inherited ALS determined by motor neurons and microglia. Science 312, 1389-1392 (2006).
Kang, S.H. et al. Degeneration and impaired regeneration of gray matter oligodendrocytes in amyotrophic lateral sclerosis. Nature neuroscience 16, 571-579 (2013).
Yamanaka, K. et al. Astrocytes as determinants of disease progression in inherited amyotrophic lateral sclerosis. Nature neuroscience 11, 251-253 (2008).
Di Giorgio, F.P., Boulting, G.L., Bobrowicz, S. & Eggan, K.C. Human embryonic stem cell-derived motor neurons are sensitive to the toxic effect of glial cells carrying an ALS-causing mutation. Cell Stem Cell 3, 637-648 (2008).
Di Giorgio, F.P., Carrasco, M.A., Siao, M.C., Maniatis, T. & Eggan, K. Non-cell autonomous effect of glia on motor neurons in an embryonic stem cell-based ALS model. Nature neuroscience 10, 608-614 (2007).
Marchetto, M.C. et al. Non-cell-autonomous effect of human SOD1 G37R astrocytes on motor neurons derived from human embryonic stem cells. Cell Stem Cell 3, 649-657 (2008).
Bosco, D.A. et al. Wild-type and mutant SOD1 share an aberrant conformation and a common pathogenic pathway in ALS. Nature neuroscience 13, 1396-1403 (2010).
Pokrishevsky, E. et al. Aberrant localization of FUS and TDP43 is associated with misfolding of SOD1 in amyotrophic lateral sclerosis. PloS one 7, e35050 (2012).
Forsberg, K. et al. Novel antibodies reveal inclusions containing non-native SOD1 in sporadic ALS patients. PLoS One 5, el 1552 (2010).
Aggarwal, S. & Cudkowicz, M. ALS drug development: reflections from the past and a way forward. Neurotherapeutics : the journal of the American Society for Experimental NeuroTherapeutics 5, 516-527 (2008).
Gurney, M.E. et al. Benefit of vitamin E, riluzole, and gabapentin in a transgenic model of familial amyotrophic lateral sclerosis. Ann Neurol 39, 147-157 (1996).
Duque, S. et al. Intravenous administration of self-complementary AAV9 enables transgene delivery to adult motor neurons. Mol Ther 17, 1187-1196 (2009).
Zhong, Z. et al. ALS-causing SOD1 mutants generate vascular changes prior to motor neuron degeneration. Nature neuroscience 11, 420-422 (2008).
Miller, R.G., Mitchell, J.D. & Moore, D.H. Riluzole for amyotrophic lateral sclerosis (ALS)/motor neuron disease (MND). Cochrane Database Syst Rev 3, CD001447 (2012).
Smith, R.A. et al. Antisense oligonucleotide therapy for neurodegenerative disease. The Journal of clinical investigation 116, 2290-2296 (2006).
Raoul, C. et al. Lentiviral-mediated silencing of SOD1 through RNA interference retards disease onset and progression in a mouse model of ALS. Nat Med 11, 423-428 (2005).
Ralph, G.S. et al. Silencing mutant SOD1 using RNAi protects against neurodegeneration and extends survival in an ALS model. Nat Med 11, 429-433 (2005).
Miller, T.M. et al. Virus-delivered small RNA silencing sustains strength in amyotrophic lateral sclerosis. Annals of neurology 57, 773-776 (2005).

(56) References Cited

OTHER PUBLICATIONS

Miller, T.M. et al. An antisense oligonucleotide against SOD1 delivered intrathecally for patients with SOD1 familial amyotrophic lateral sclerosis: a phase 1, randomised, first-in-man study. Lancet neurology 12, 435-442 (2013).
Towne, C., Raoul, C., Schneider, B.L. & Aebischer, P. Systemic AAV6 delivery mediating RNA interference against SOD1: neuromuscular transduction does not alter disease progression in fALS mice. Mol Ther 16, 1018-1025 (2008).
Towne, C., Setola, V., Schneider, B.L. & Aebischer, P. Neuroprotection by gene therapy targeting mutant SOD1 in Individual pools of motor neurons does not translate into therapeutic benefit in fALS mice. Mol Ther 19, 274-283 (2011).
Mandel, R.J., Lowenstein, P.R. & Byrne, B.J. AAV6-mediated gene silencing fALS short. Mol Ther 19, 231-233 (2011).
Synofzik, M. et al. Mutant superoxide dismutase-1 indistinguishable from wild-type causes ALS. Human molecular genetics 21, 3568-3574 (2012).
Guareschi, S. et al. An over-oxidized form of superoxide dismutase found in sporadic amyotrophic lateral sclerosis with bulbar onset shares a toxic mechanism with mutant SOD1. Proc Natl Acad SciUSA 109, 5074-5079 (2012).
Bevan, A.K. et al. Systemic gene delivery in large species for targeting spinal cord, brain, and peripheral tissues for pediatric disorders. Mol Ther 19, 1971-1980 (2011).
Gray, S.J. et al. Preclinical differences of intravascular AAV9 delivery to neurons and glia: a comparative study of adult mice and nonhuman primates. Mol Ther 19, 1058-1069 (2011).
Lioy, D.T. et al. A role for glia in the progression of Rett's syndrome. Nature 475, 497-500 (2011).
Miranda, C.J. et al. Aging brain microenvironment decreases hippocampal neurogenesis through Wnt-mediated survivin signaling. Aging Cell 11, 542-552 (2012).
Yamanaka, K. et al. Mutant SOD1 in cell types other than motor neurons and oligodendrocytes accelerates onset of disease in ALS mice. Proc Natl Acad Sci USA 105, 7594-7599 (2008).
Swarup et al, Deregulation of TDP-43 in amyotrophic lateral sclerosis triggers nuclear factor κB-mediated pathogenic pathways, J Exp Med, 208(12): p. 2429-2447.
Lewis et al., "The Neuroinflammmatory Response in ALS: The Roles of Microglia and T Cells," Neurology Research Int'l., 23(12): 5197-8 (Jan. 1, 2012).
Trapani et al., "Functional significance of the perforin/granzyme cell death pathway," J. Immunology, 2(10): 735-747 (Oct. 1, 2002).
Ilzecka et al., "Granzymes A and B levels in serum of patients with amyotrophic lateral sclerosis," Clinical Biochemistry, 44(8): 650-653 (Feb. 13, 2011).
Gasque et al., Identification of Astrocyte Cell Population from Human Brain that Expresses Perforin, a Cytotoxic Protein Implicated in Immune Defense, J Exp Med, 1998, 187(4): 451-460.
Ruocco et al, "IκB binase (IKK)beta, but not IKKalpha, is a critical mediator of osteoclast survival and is required for inflammation-induced bone loss", The Journal of Experimental Medicine, vol. 201, No. 10, May 16, 2005, pp. 1677-1687.
Haidet-Phillips et al, Astrocytes from familial and sporadic ALS patients are toxic to motor neurons, Nat Biotech, 2011, 29(9): 824-828.
GenBank: M28393.1, Human perforin mRNA, complete cds (retrieved on Apr. 3, 2014 from http://www.ncbi.nlm.nih.gov/nuccore/M28393), 1995.
Marchetto et al., Non-Cell-Autonomous Effect of Human SOD1G37R Astrocytes on Motor Neurons Derived from Human Embryonic Stem Cells, Cell Stem Cell 3, 649?657, 2008.
PCT International Search Report/Written Opinion for PCT/US2013/060153, completed on Apr. 3, 2014.
Sambrook et al., "Molecular Cloning: A Laboratory Manual", 3rd Edition, Cold Spring Harbor Laboratory Press, (2001). Book Reference.

Goodchild, et al., "Inhibition of replication and expression of human T-cell lymphotropic virus type III in cultured cells by exogenous synthetic oligonucleotides complementary to viral RNA", Proc. Natl. Acad. Sci. 83:4143-4146 (1986).
Foust, K.D., et al. Intravascular AAV9 preferentially targets neonatal neurons and adult astrocytes. Nat Biotechnol, 27, 59-65, (2009).
Remington: The Science & Practice of Pharmacy, 21st Edition (Lippincott Williams & Wilkins, 2005). Book Reference.
Tiscornia et al., Nat Protoc, 2006, 1, 241.
Foust et al, Therapeutic AAV9-mediated Suppression of Mutant SOD1 Slows Disease Progerssion and Extends Survival in Models of Inherited ALS, Molecular Therapy, 21(12): 2148-2159 (2013).
The Science & Practice of Pharmacy,21st Edition (Lippincott Williams & Wilkins, 2005). Book Reference.
Thompson, A., van der Slik, A.R., Koning, F. & van Bergen, J. An improved RT-PCR method for the detection of killer-cell immunoglobulin-like receptor (KIR) transcripts. Immunogenetics, 58, 865-872 (2006).
Cardona et al., "Isolation of murine microglial cells for RNA analysis or flow cytometry", Nature Protocols, vol. 1, No. 4, Nov. 2006.
Moussaud and Draheim, "A new method to isolate microglia from adult mice and culture them for an extended period of time", Journal of Neuroscience Methods 187, 2010.
Erblich et al, "Absence of Colony Stimulation Factor-1 Receptor Results in Loss of Microglia, Disrupted Brain Development and Olfactory Deficits", PloS One, vol. 6, Issue 10, Oct. 2011.
Wichterle et al., "Directed Differentiation of Embryonic Stem Cells into Motor Neurons", Cell, vol. 110, Aug. 2002.
Miranda, C.J., et al. Aging brain microenvironment decreases hippocampal neurogenesis through Wnt-mediated survivin signaling. Aging Cell (2012).
Ghosh and Karin, "Mising Pieces in the NF-κB Puzzle", Cell, vol. 109,. Apr. 2002.
Ray, J. & Gage, F.H. Differential properties of adult rat and mouse brain-derived neural stem/progenitor cells. Mol Cell Neurosci, 31, 560-573 (2006).
Nagai et al, "Astrocytes expressing ALS-linked mutated SOD1 release factors selectively toxic to motor neurons", Nature Neuroscience, vol. 10, No. 5, May 2007.
Wang et al., "Congrol of inducible chemoresistance: Enhanced anti-tumor therapy through increased apoptosis by inhibition of NF=κB", Nature Medicine, vol. 5, No. 4, Apr. 1999.
Li et al, "IKKbeta Is Required for Peripheral B Cell Survival and Proliferation", The Journal of Immunology, 2003.
Park et al., "Macrophage Apoptosis by Anthrax Lethal Factor Through p38 MAP Kinase Inhibition", Science, vol. 297, Sep. 2002.
Crosio et al, 2011, Astroglial Inhibtition of NF-KB Does not Ameliorate Disease Onset and Progression in a Mouse Model for Amyotrophic Lateral Sclerosis (ALS), PLoS One, 6(3): e17187.
Magness et al., "In Vivo Pattern of Lipopolysaccharide and Anti-CD3-Induced NF-κB Activation Using a Novel Gene-Targeted Enhanced GFP Reporter Gene Mouse", J. Immunol, 2004.
Xiao et al, "Mutant SOD1 G93A microglia are more neurotoxic relative to wild-type microglia", Journal of Neurochemistry, 2007, 102, pp. 2008-2019.
Sasmono et al, "A macrophage colony-stimulating factor receptor-green fluorescent protein transgene is expressed throughout the mononuclear phagocyte system of the mouse", Blood, Feb. 1, 2003, vol. 101, No. 3, pp. 1155-1163.
Frakes et al., "The Role of Neuroinflammation in the Pathogenesis of Amyotrophic Lateral Sclerosis," (2014), pp. 1-175, Retrieved Mar. 24, 2017 from the Internet: https://etd.ohiolink.edu/!etd.send_file?accession=osu14176499548&disposition=attachment.
Labuzek et al., "Ambivalent effects of compound C (dorsomorphin) on inflammatory response in LPS-stimulated rat primary microglial cultures," Naunyn-Schmiedebergs Arch Pharmacol., (2010) 381(1):41-57.
Yang et al., "AAV-based shRNA silencing of NF-κB ameliorates muscle pathologies in mdxmice," Gene Therapy, (2012) 19: 1196-1204.

(56) References Cited

OTHER PUBLICATIONS

Zhang et al., "Hypothalamic programming of systemic ageing involving IKK-β, NF-κB and GnRH," Nature, (2013) 497: 211-216.
Extended European Search Report in App. No. EP14859909.5, issued Apr. 12, 2017.

* cited by examiner

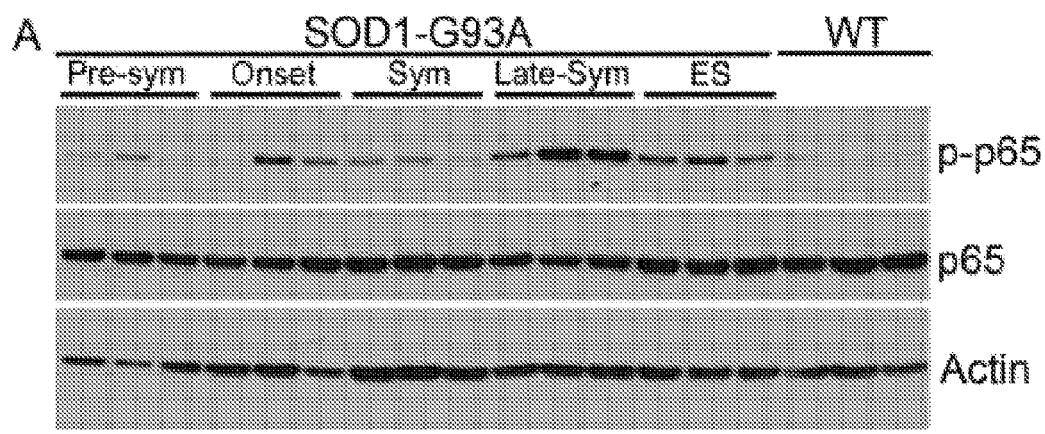
FIG. 1A
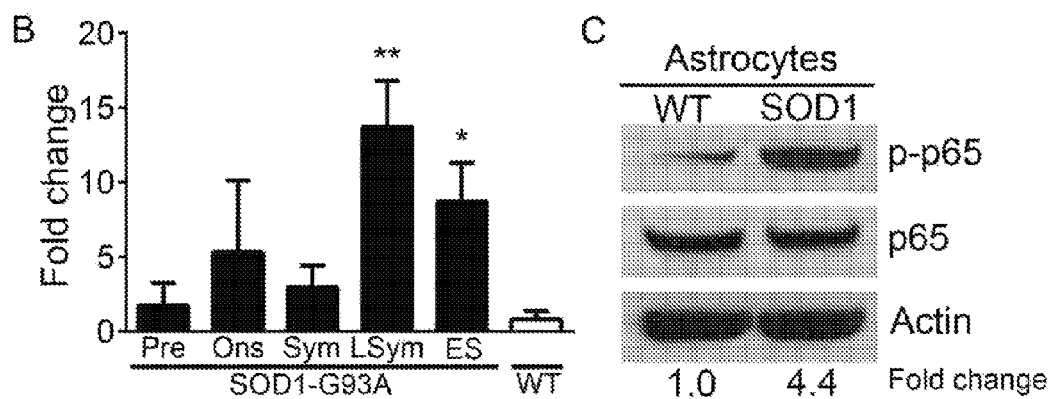
FIG. 1B
FIG. 1C

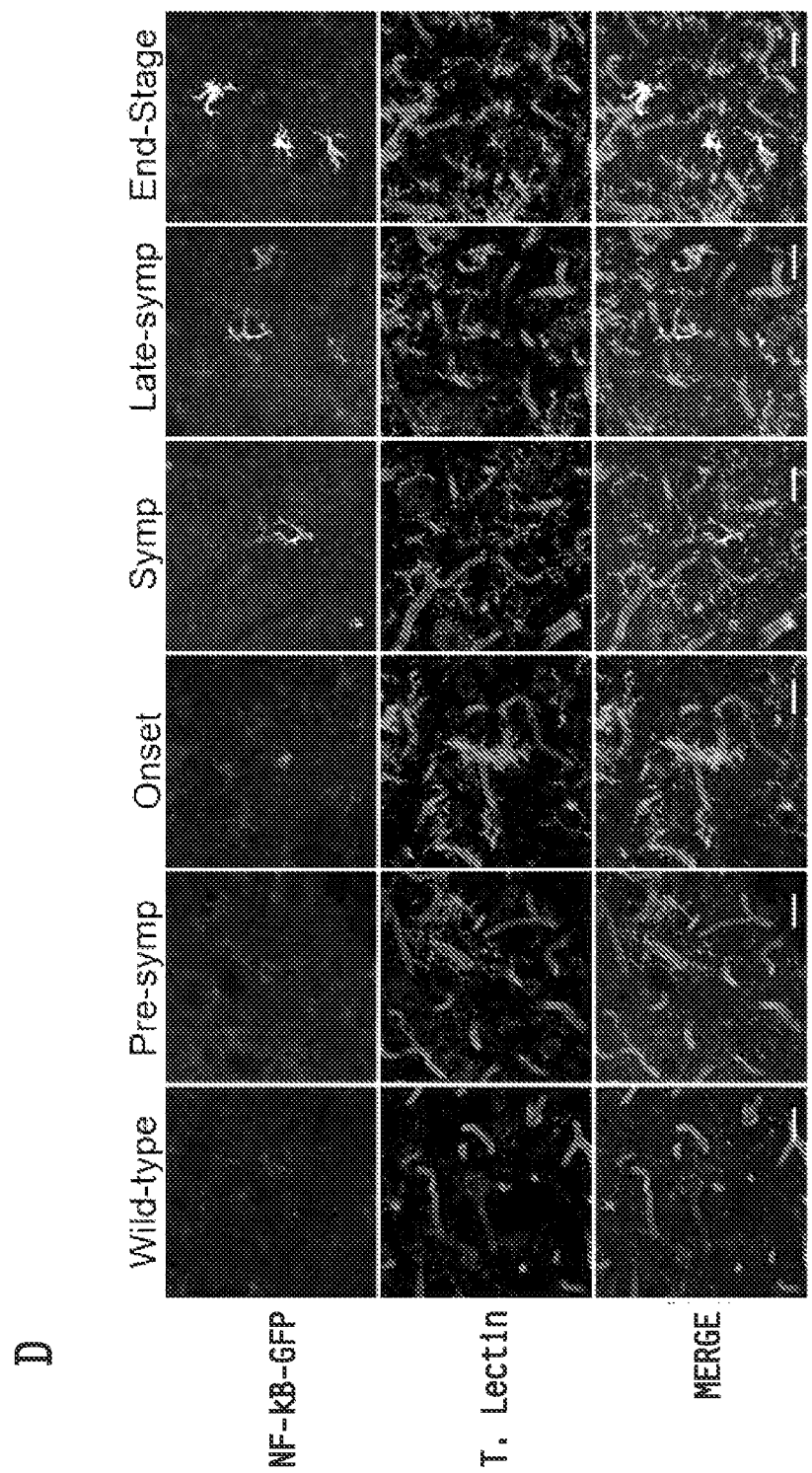

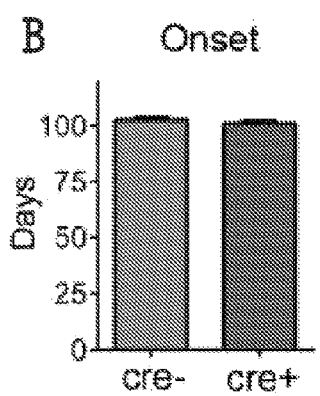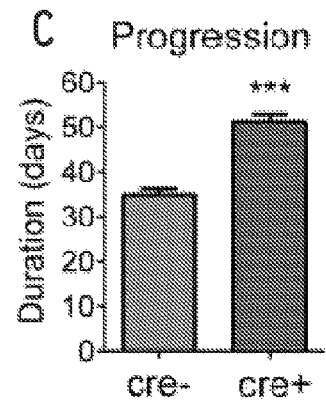
FIG. 5B
FIG. 5C
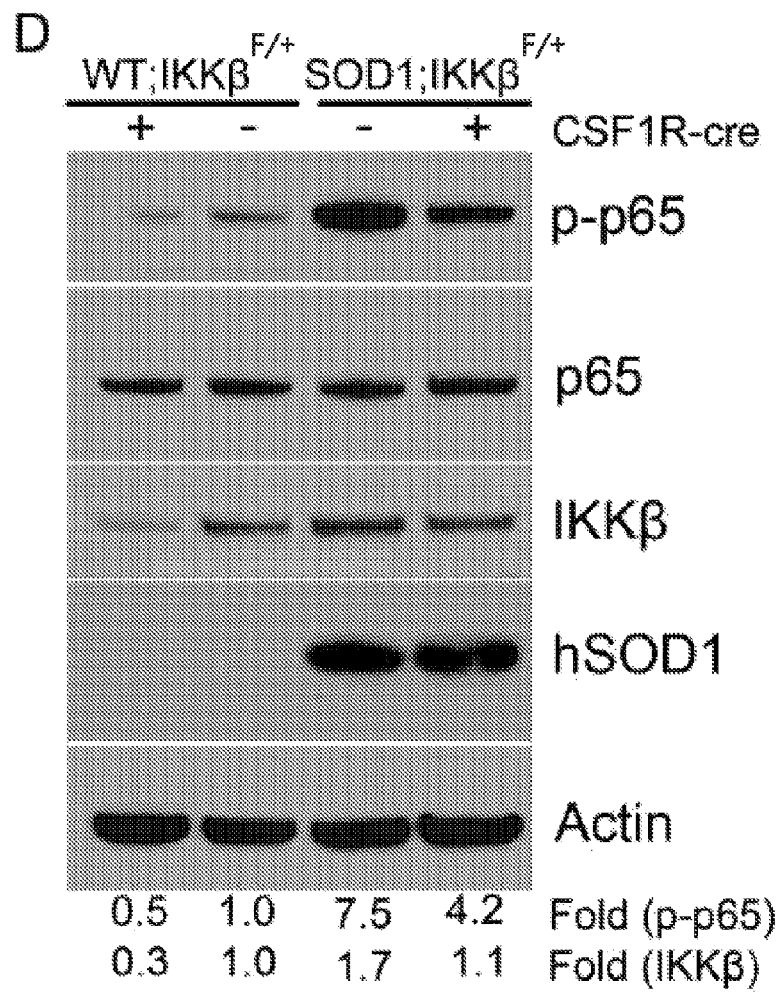
FIG. 5D

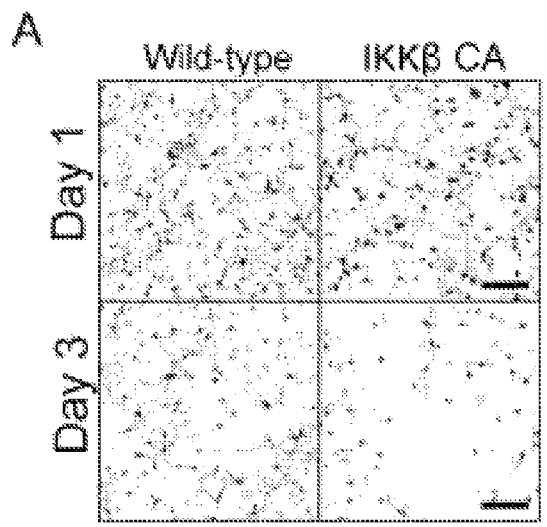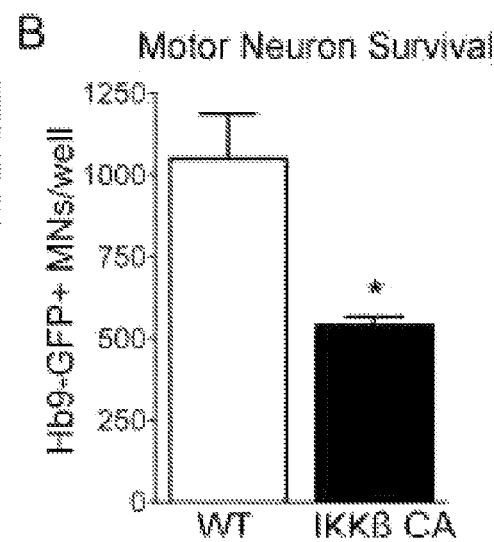
FIG. 7A    FIG. 7B
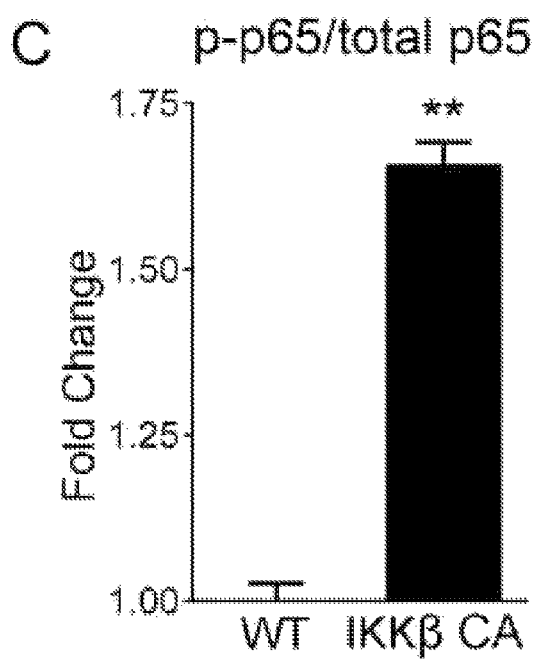
FIG. 7C

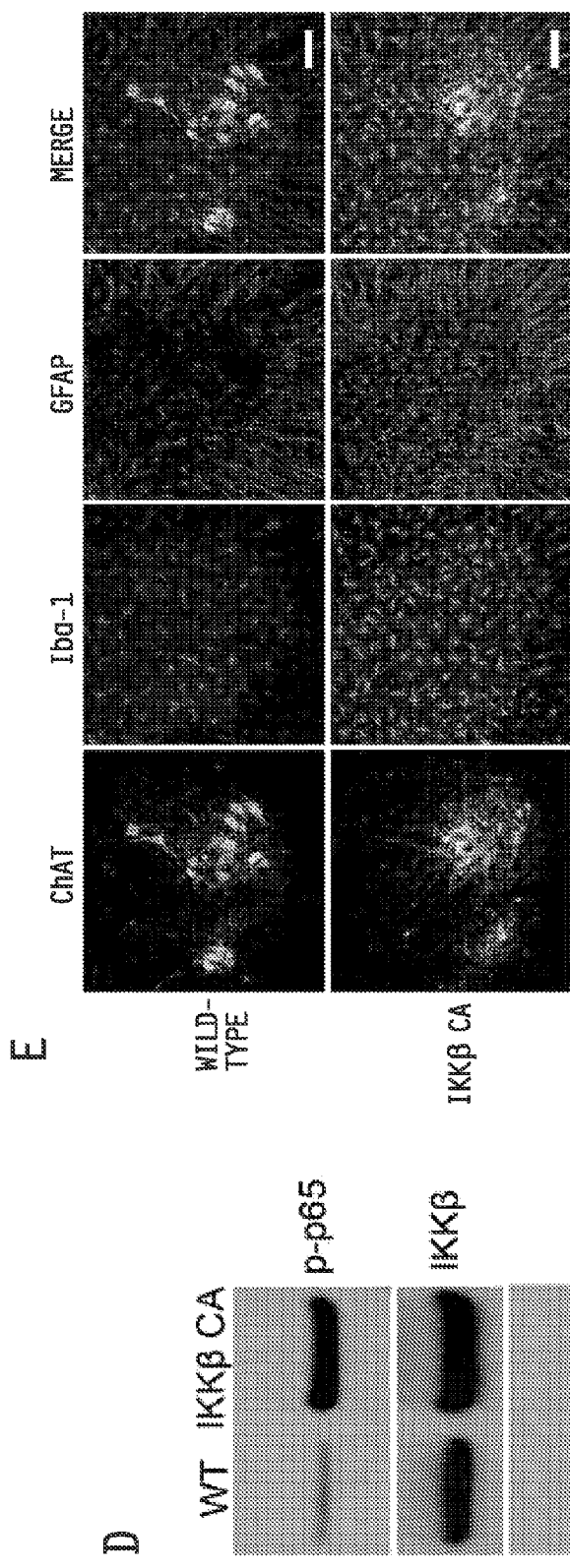

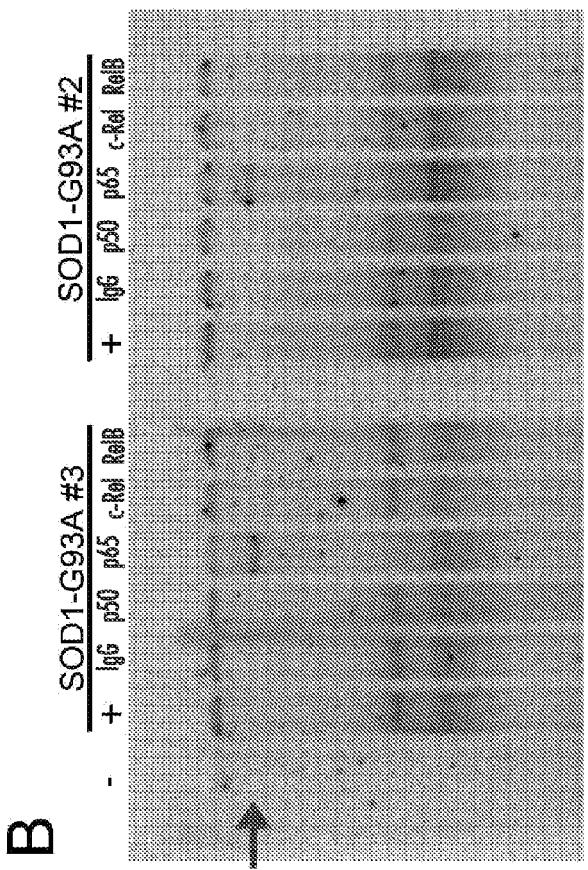
FIG. S1-A
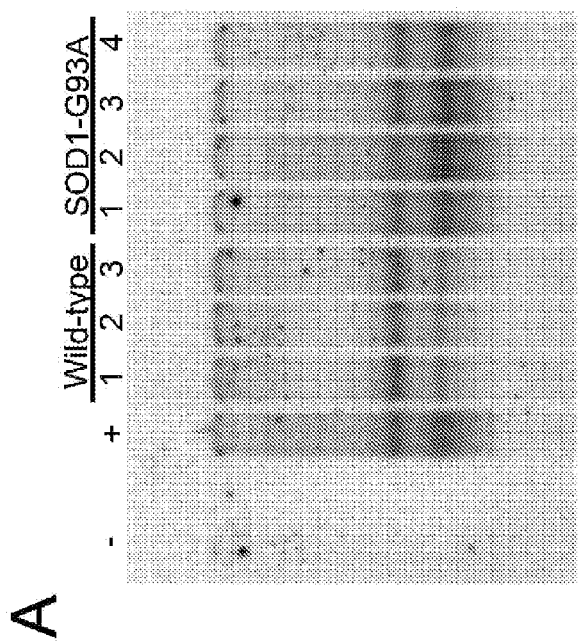
FIG. S1-B
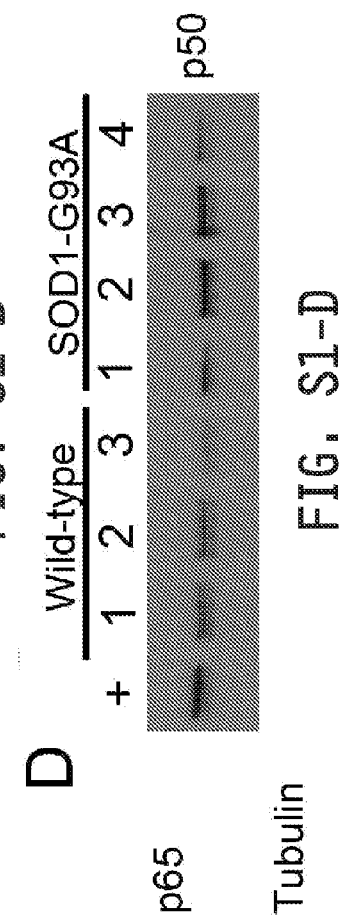
FIG. S1-C
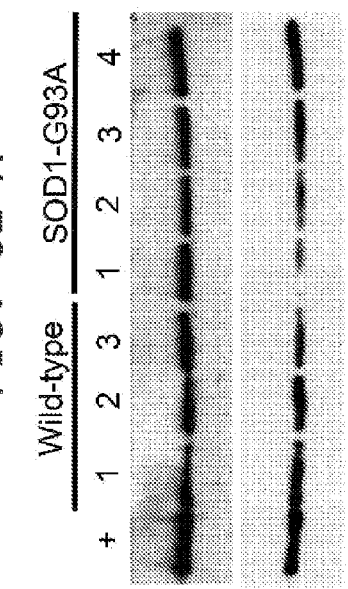
FIG. S1-D

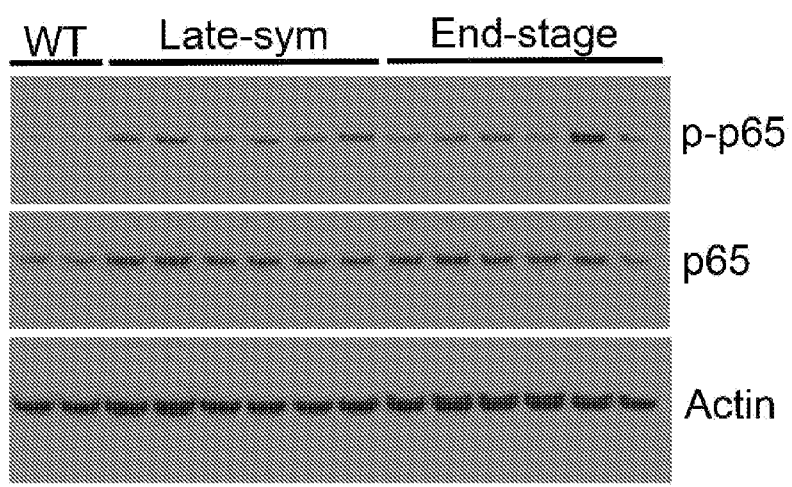
FIG. S1-E
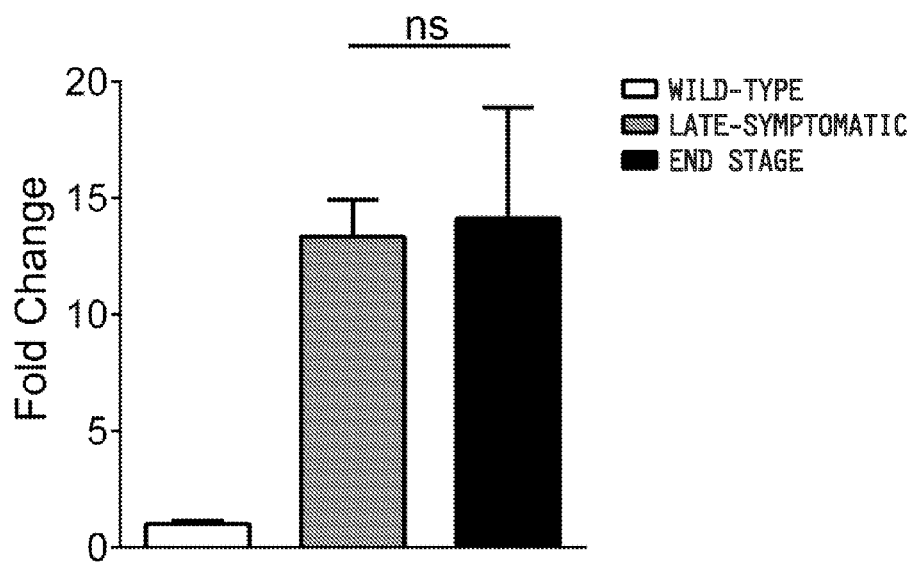
FIG. S1-F

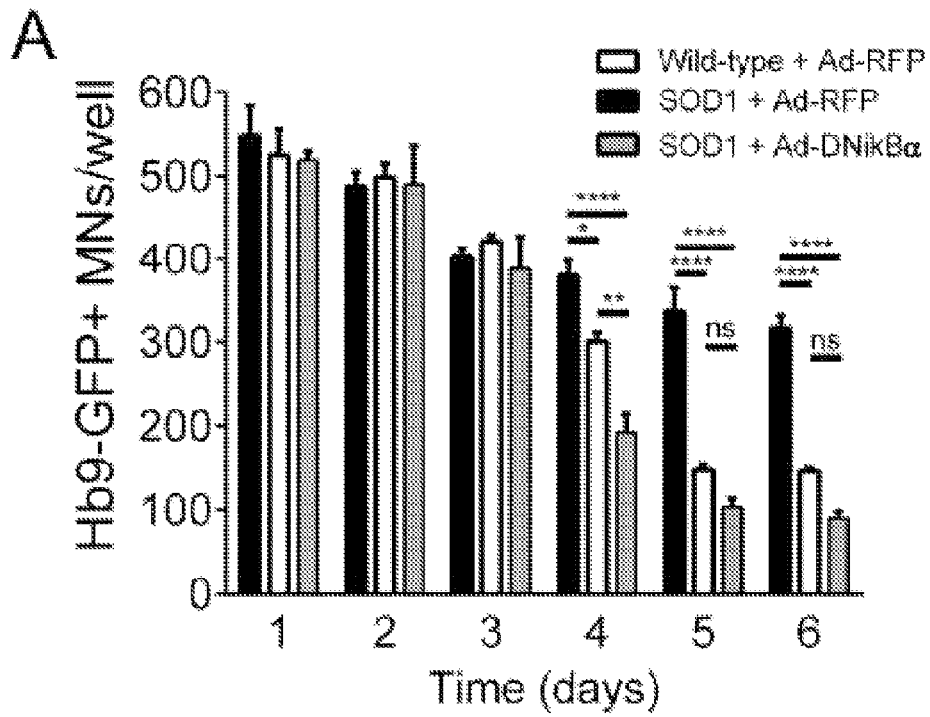
FIG. S2-A
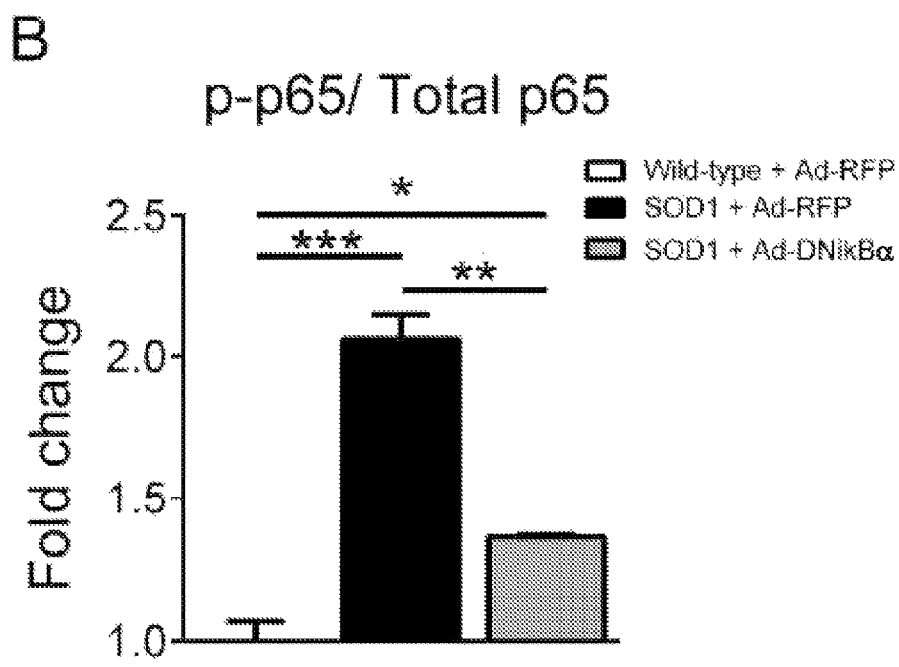
FIG. S2-B

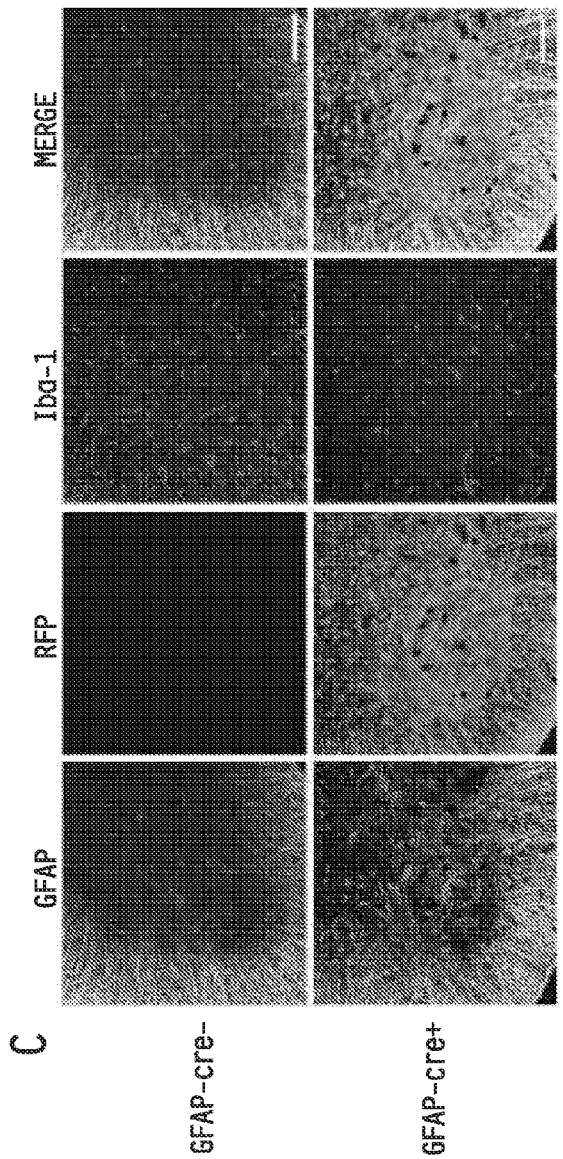
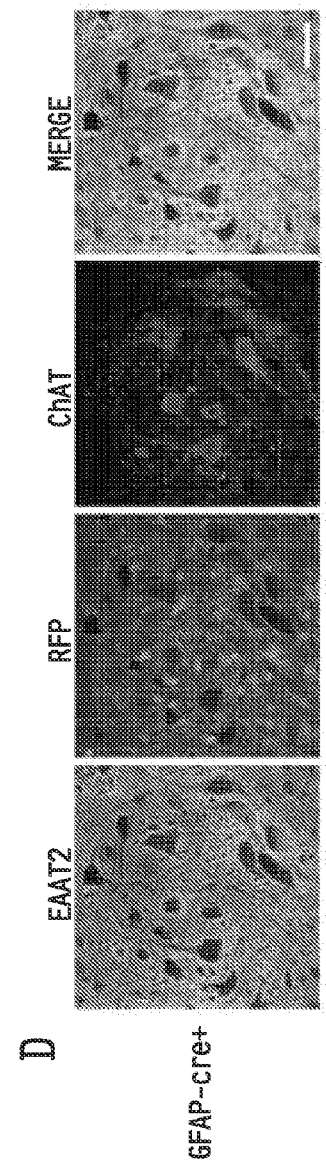
FIG. S2-C
FIG. S2-D

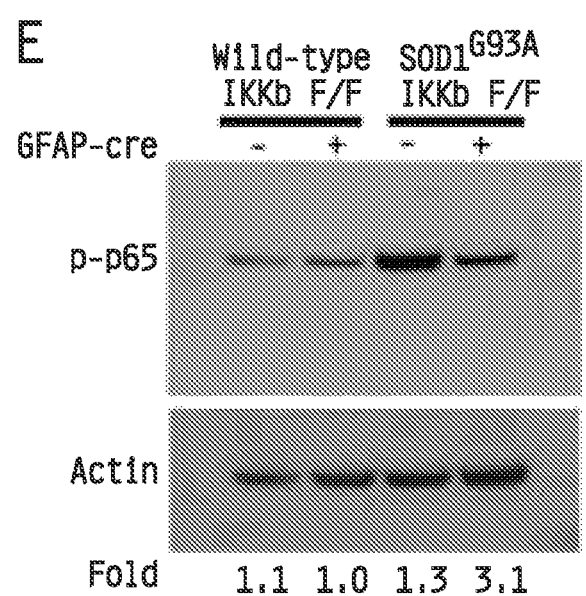
FIG. S2-E

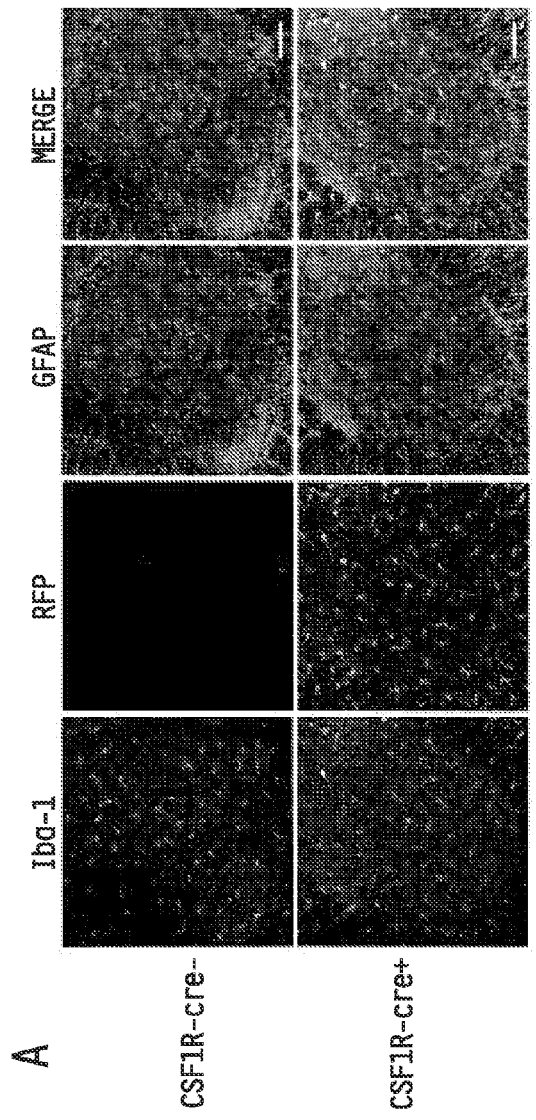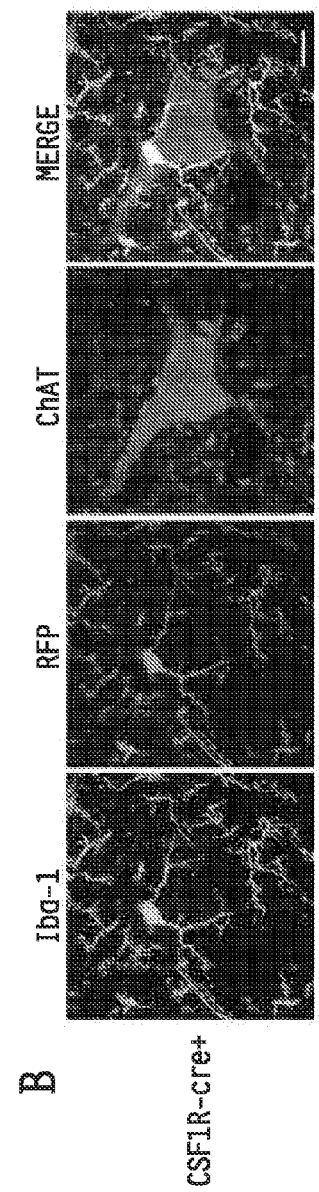
FIG. S3-A
FIG. S3-B

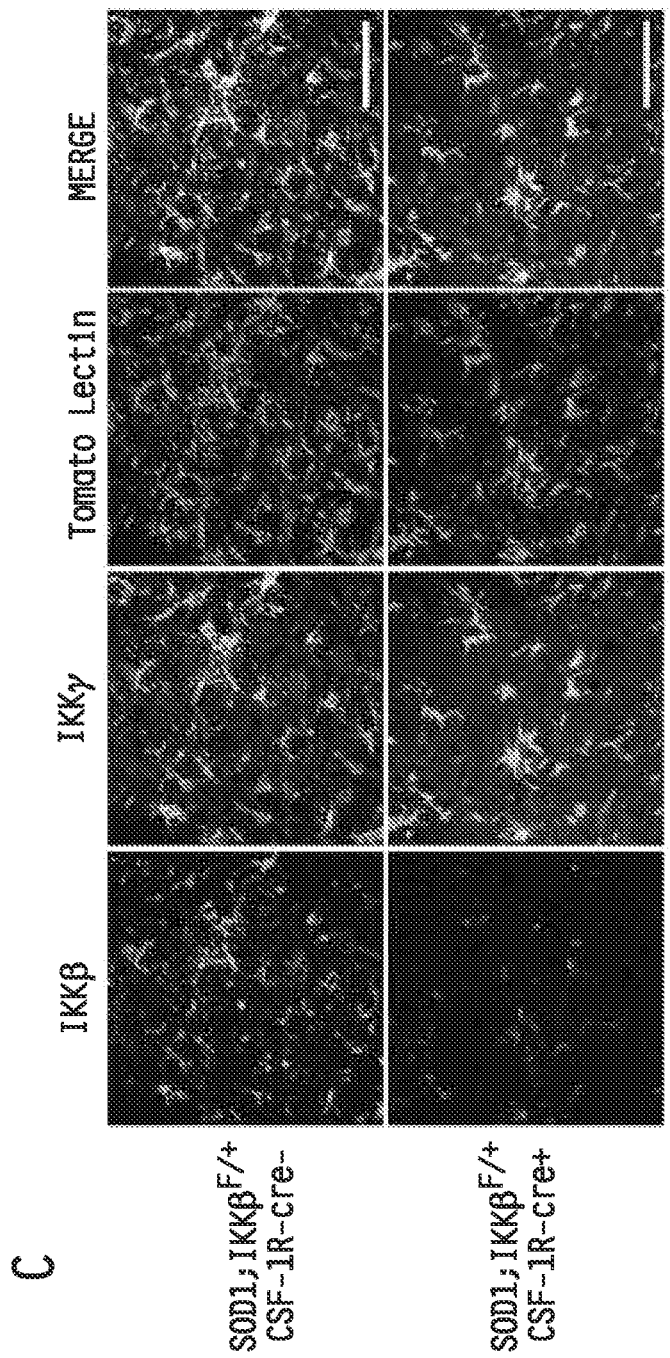
FIG. S3-C

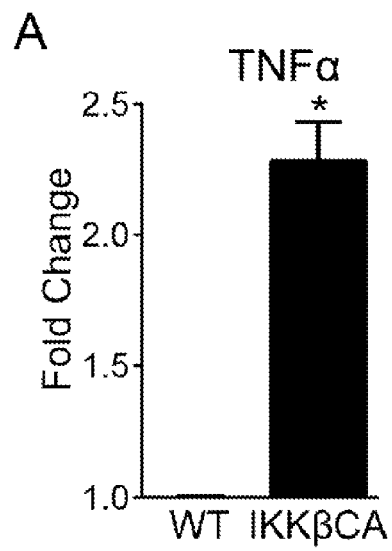
FIG. S4-A
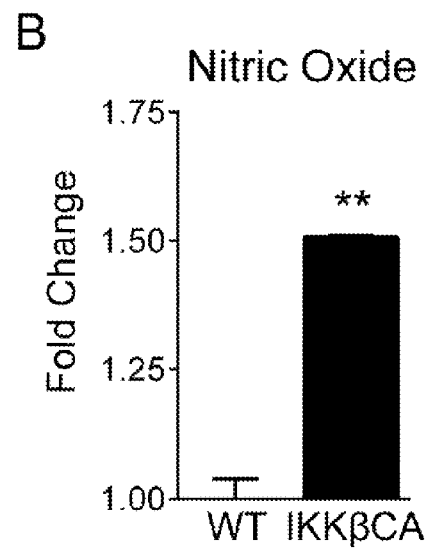
FIG. S4-B
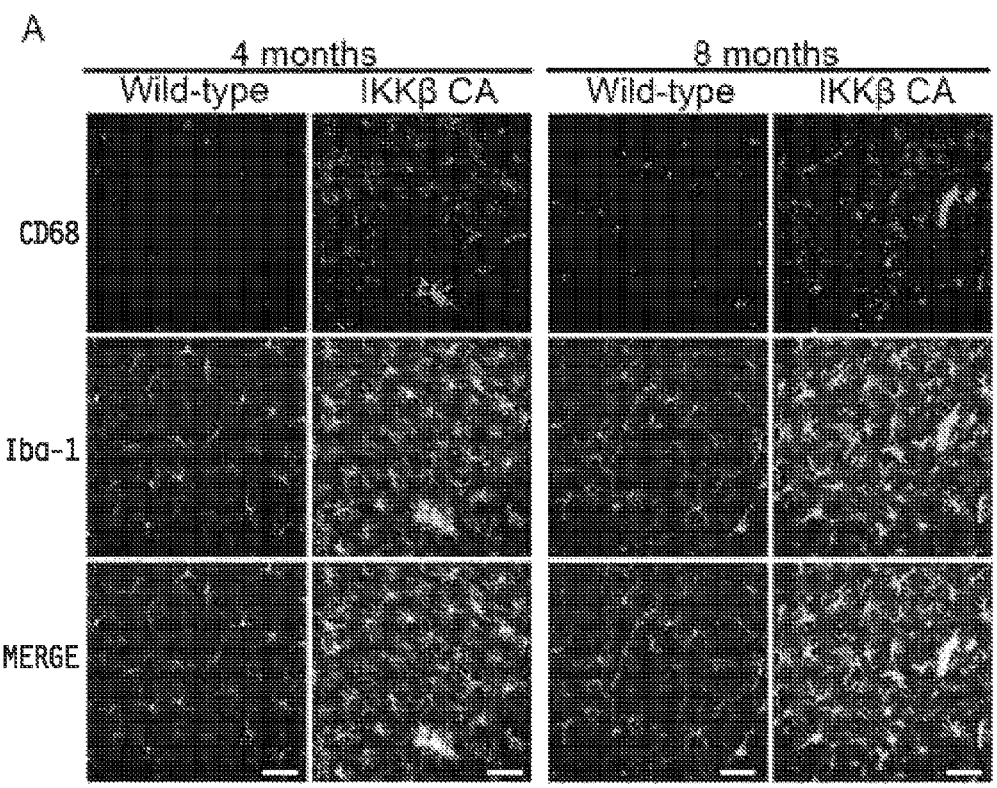
FIG. S5-A

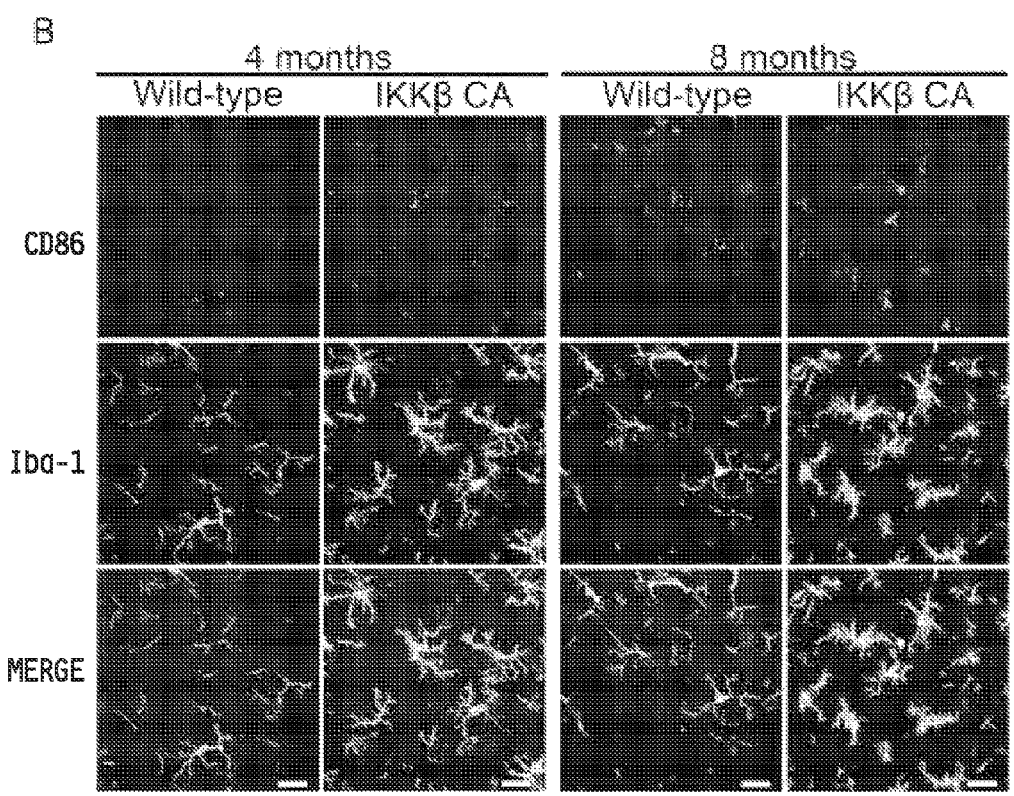
FIG. S5-B

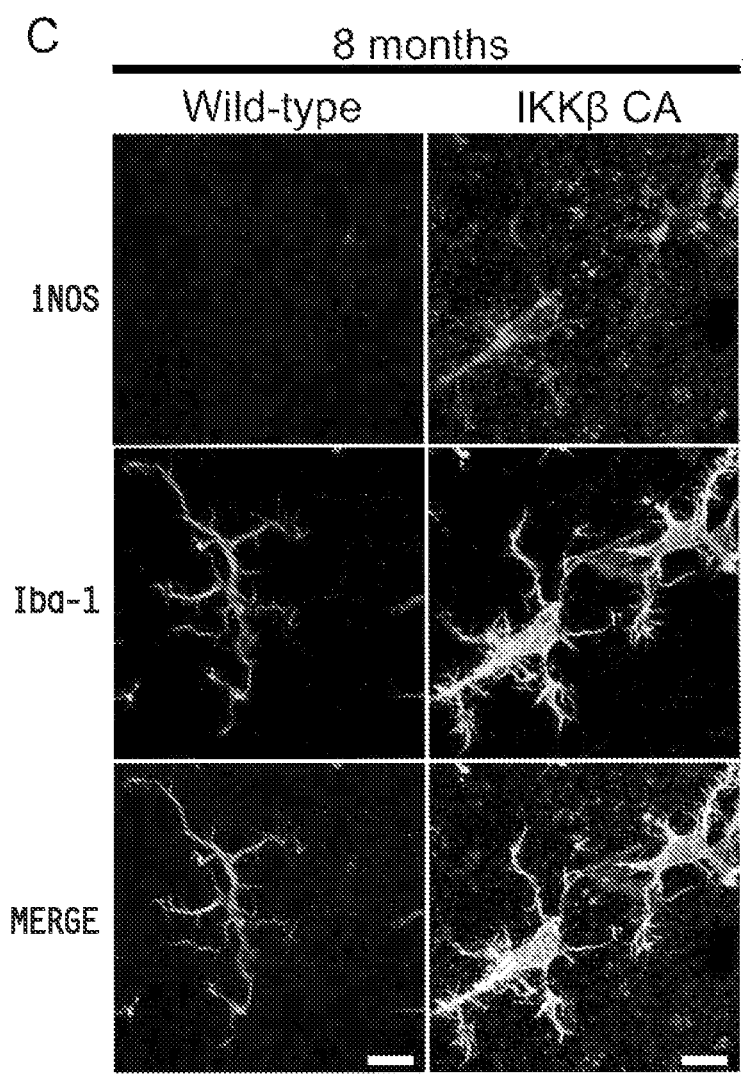
FIG. S5-C

COMPOSITIONS AND METHODS FOR INHIBITING NF-κB AND SOD-1 TO TREAT AMYOTROPHIC LATERAL SCLEROSIS

CROSS-REFERENCE TO RELATED APPLICATIONS

This application is the National Stage, under 35 U.S.C. §371, of International Application No. PCT/US2014/063890, filed Nov. 4, 2014, which claims the benefit, under 35 U.S.C. §119(e), to U.S. Provisional Application No. 61/900,105, filed on Nov. 5, 2013, the contents of both of which applications are incorporated herein by reference in their entireties.

GOVERNMENT RIGHTS

This invention was made with government support under T32NS077984 and R01 NS644912 awarded by NIH/NINDS. The government has certain rights in the invention.

TECHNICAL FIELD

The invention relates to compositions, kits, methods, and uses for the treatment of amyotrophic lateral sclerosis. In particular, the invention relates to compositions, kits, methods, and uses for the treatment of amyotrophic lateral sclerosis by inhibiting NF-κB in microglia and by inhibiting motor neuron (MN) death. The invention further relates to compositions, kits, methods, and uses for the treatment of amyotrophic lateral sclerosis by inhibiting NF-κB in microglia in combination with inhibiting SOD-1 in astrocytes, motor neurons, neurons, and oligodendrocytes. The invention also relates to a method for inhibiting the expression or the activity of NF-κB in microglia or macrophages to inhibit motor neuron death, and to a method for inhibiting the expression or the activity of NF-κB in microglia or macrophages and for inhibiting SOD-1 expression in astrocytes to inhibit motor neuron death.

BACKGROUND AND SUMMARY

Amyotrophic lateral sclerosis, commonly referred to as Lou Gehrig's disease, is characterized by selective, premature degeneration and death of motor neurons in the motor cortex, brain stem and spinal cord. The loss of motor neurons causes progressive muscle paralysis ultimately leading to death from respiratory failure. Approximately 90% of all amyotrophic lateral sclerosis cases are sporadic amyotrophic lateral sclerosis, without a family history of the disease, and the other approximately 10 percent of cases are cases of familial amyotrophic lateral sclerosis. Despite significant efforts to identify risk factors and potential susceptibility genes, the etiology of sporadic amyotrophic lateral sclerosis remains largely unknown.

Various rodent models carrying dominant mutations of the human superoxide dismutase (SOD1) that is causative in about 20 percent of familial amyotrophic lateral sclerosis cases, have been instrumental to model motor neuron toxicity in amyotrophic lateral sclerosis. These models have demonstrated that not only motor neurons, but also non-neuronal cell types including microglia and astrocytes play a significant role in disease onset and progression. Studies have identified microglia as mediators of motor neuron death in amyotrophic lateral sclerosis by a yet undetermined inflammatory mechanism. Insight into the mechanisms underlying motor neuron death in amyotrophic lateral sclerosis as a result of neuroinflammatory effects is pertinent for the development of successful therapies for amyotrophic lateral sclerosis.

Accordingly, the present inventors have discovered that the mechanism underlying motor neuron death as a result of neuroinflammation is activation of NF-κB in microglia, and have used this knowledge to develop therapies for amyotrophic lateral sclerosis. The pharmaceutical compositions, methods and uses, and kits described herein can be used to treat sporadic or familial amyotrophic lateral sclerosis.

Several embodiments of the invention are described by the following enumerated clauses:

1. A method for treating a patient with amyotrophic lateral sclerosis by decreasing the expression of NF-κB in the patient, the method comprising the steps of
   administering to the patient a composition comprising an effective amount of a compound that decreases the expression of NF-κB in microglia or macrophages of the patient; and
   inhibiting motor neuron death in the patient.
2. The method of clause 1 wherein the expression of NF-κB is decreased in microglia.
3. The method of clause 1 wherein the expression of NF-κB is decreased in macrophages.
4. The method of any one of clauses 1 to 3 wherein the decrease in expression of NF-κB in microglia is effective for reducing the symptoms of amyotrophic lateral sclerosis.
5. The method of any one of clauses 1 to 4 wherein a decrease in the level of expression of NF-κB in astrocytes is not effective for reducing the symptoms of amyotrophic lateral sclerosis.
6. The method of any one of clauses 1 to 5 wherein the composition comprises an aqueous solution.
7. The method of any one of clauses 1 to 6 wherein the compound is selected from the group consisting of a drug, a peptide, and a nucleic acid.
8. The method of clause 7 wherein the compound is a nucleic acid.
9. The method of clause 8 wherein the nucleic acid functions by RNA interference or is an antisense RNA molecule.
10. The method of clause 8 wherein the nucleic acid is selected from the group consisting of an siRNA, an miRNA, and an shRNA.
11. The method of clause 10 wherein the nucleic acid is an shRNA.
12. The method of any one of clauses 8 to 11 wherein the nucleic acid is delivered to the patient in a bacterial vector or in a viral vector.
13. The method of any one of clauses 8 to 11 wherein the nucleic acid has the sequence of SEQ ID NO: 1 or SEQ ID NO: 2.
14. The method of any one of clauses 12 to 13 wherein the vector is a viral vector.
15. The method of any one of clauses 1 to 14 wherein the amyotrophic lateral sclerosis is sporadic amyotrophic lateral sclerosis.
16. The method of any one of clauses 1 to 14 wherein the amyotrophic lateral sclerosis is familial amyotrophic lateral sclerosis.
17. The method of any one of clauses 1 to 16 wherein the amount of the compound is in the range of about 1 ng/kg of patient body weight to about 1 mg/kg of patient body weight.

18. The method of any one of clauses 1 to 17 wherein the amount of the compound is in the range of about 1 ng/kg of patient body weight to about 500 ng/kg of patient body weight.

19. The method of any one of clauses 1 to 18 wherein the amount of the compound is in the range of about 1 ng/kg of patient body weight to about 100 ng/kg of patient body weight.

20. The method of any one of clauses 1 to 19 wherein the composition further comprises a carrier, an excipient, or a diluent, or a combination thereof.

21. The method of clause 20 wherein the composition comprises a pharmaceutically acceptable carrier, wherein the pharmaceutically acceptable carrier is a liquid carrier.

22. The method of clause 21 wherein the liquid carrier is selected from the group consisting of saline, glucose, alcohols, glycols, esters, amides, and a combination thereof.

23. The method of any one of clauses 1 to 22 wherein the composition is administered in a single-dose or a multiple-dose regimen.

24. A method for treating amyotrophic lateral sclerosis by inhibiting the activity of NF-κB in microglia or macrophages of a patient, the method comprising the step of
    administering to the patient a composition comprising an effective amount of a compound that inhibits the activity of NF-κB in microglia or macrophages of the patient; and
    inhibiting motor neuron death in the patient.

25. The method of clause 24 wherein the activity of NF-κB is decreased in microglia.

26. The method of clause 24 wherein the activity of NF-κB is decreased in macrophages.

27. The method of any one of clauses 24 to 26 wherein the decrease in activity of NF-κB in microglia is effective for reducing the symptoms of amyotrophic lateral sclerosis.

28. The method of any one of clauses 24 to 27 wherein a decrease in the level of activity of NF-κB in astrocytes is not effective for reducing the symptoms of amyotrophic lateral sclerosis.

29. The method of any one of clauses 24 to 28 wherein the composition comprises an aqueous solution.

30. The method of any one of clauses 24 to 29 wherein the compound is selected from the group consisting of a drug, a peptide, and a nucleic acid.

31. The method of clause 30 wherein the compound is a nucleic acid.

32. The method of clause 31 wherein the nucleic acid is delivered to the patient in a bacterial vector or in a viral vector.

33. The method of clause 32 wherein the vector is a viral vector.

34. The method of clause 33 wherein the vector is selected from the group consisting of a lentiviral vector, an adeno-associated virus vector, and an adenovirus vector.

35. The method of any one of clauses 31 to 34 wherein the nucleic acid has the sequence of SEQ ID NO: 1 or SEQ ID NO: 2.

36. The method of any one of clauses 24 to 35 wherein the amyotrophic lateral sclerosis is sporadic amyotrophic lateral sclerosis.

37. The method of any one of clauses 24 to 35 wherein the amyotrophic lateral sclerosis is familial amyotrophic lateral sclerosis.

38. The method of any one of clauses 24 to 37 wherein the amount of the compound is in the range of about 1 ng/kg of patient body weight to about 1 mg/kg of patient body weight.

39. The method of any one of clauses 24 to 38 wherein the amount of the compound is in the range of about 1 ng/kg of patient body weight to about 500 ng/kg of patient body weight.

40. The method of any one of clauses 24 to 39 wherein the amount of the compound is in the range of about 1 ng/kg of patient body weight to about 100 ng/kg of patient body weight.

41. The method of any one of clauses 24 to 40 wherein the composition further comprises a carrier, an excipient, or a diluent, or a combination thereof.

42. The method of clause 41 wherein the composition comprises a pharmaceutically acceptable carrier, wherein the pharmaceutically acceptable carrier is a liquid carrier.

43. The method of clause 42 wherein the liquid carrier is selected from the group consisting of saline, glucose, alcohols, glycols, esters, amides, and a combination thereof.

44. The method of any one of clauses 24 to 43 wherein the composition is administered in a single-dose or a multiple-dose regimen.

45. A pharmaceutical composition comprising a dosage form of a compound effective to decrease the expression of NF-κB in the microglia or macrophages of a patient with amyotrophic lateral sclerosis.

46. The composition of claim 45 wherein the expression of NF-κB in microglia is decreased.

47. The composition of claim 45 wherein the expression of NF-κB in macrophages is decreased.

48. The composition of any one of clauses 45 to 47 wherein the compound is selected from the group consisting of a drug, a peptide, and a nucleic acid.

49. The composition of clause 48 wherein the compound is a nucleic acid.

50. The composition of clause 49 wherein the nucleic acid is selected from the group consisting of siRNA, an miRNA, and an shRNA.

51. The composition of clause 50 wherein the compound is an antisense RNA molecule.

52. The composition of clause 50 wherein the nucleic acid is an shRNA.

53. The composition of any one of clauses 49 to 52 wherein the nucleic acid has the sequence of SEQ ID NO: 1 or SEQ ID NO: 2.

54. The composition of any one of clauses 45 to 53, wherein the composition further comprises one or more carriers, diluents, or excipients, or a combination thereof.

55. The composition of clause 54 wherein the composition comprises a pharmaceutically acceptable carrier, wherein the pharmaceutically acceptable carrier is a liquid carrier.

56. The composition of clause 55 wherein the liquid carrier is selected from the group consisting of saline, glucose, alcohols, glycols, esters, amides, and a combination thereof.

57. The composition of any one of clauses 45 to 56 wherein the purity of the compound is at least 98 percent based on weight percent.

58. The composition of any one of clauses 45 to 57 wherein the composition is in an ampoule or a sealed vial.

59. The composition of any one of clauses 45 to 54 or 57 to 58 in the form of a reconstitutable lyophilizate.

60. A pharmaceutical composition comprising a dosage form of a compound effective to decrease the activity of NF-κB in the microglia or macrophages of a patient with amyotrophic lateral sclerosis.

61. The composition of claim 60 wherein the expression of NF-κB in microglia is decreased.

62. The composition of claim 60 wherein the expression of NF-κB in macrophages is decreased.

63. The composition of any one of clauses 60 to 62 wherein the compound is selected from the group consisting of a drug, a peptide, and a nucleic acid.

64. The composition of clause 63 wherein the compound is a nucleic acid.

65. The composition of clause 64 wherein the nucleic acid is selected from the group consisting of siRNA, an miRNA, and an shRNA.

66. The composition of any one of clauses 63 to 65 wherein the compound is an antisense RNA molecule.

67. The composition of clause 65 wherein the nucleic acid is an shRNA.

68. The composition of clause 67 wherein the nucleic acid has the sequence of SEQ ID NO: 1 or SEQ ID NO: 2.

69. The composition of any one of clauses 60 to 68, wherein the composition further comprises one or more carriers, diluents, or excipients, or a combination thereof.

70. The composition of clause 69 wherein the composition comprises a pharmaceutically acceptable carrier, wherein the pharmaceutically acceptable carrier is a liquid carrier.

71. The composition of clause 70 wherein the liquid carrier is selected from the group consisting of saline, glucose, alcohols, glycols, esters, amides, and a combination thereof.

72. The composition of any one of clauses 60 to 71 wherein the purity of the compound is at least 98 percent based on weight percent.

73. The composition of any one of clauses 60 to 72 wherein the composition is in an ampoule or a sealed vial.

74. The composition of any one of clauses 60 to 69 or 72 to 73 in the form of a reconstitutable lyophilizate.

75. The method or pharmaceutical composition of any one of clauses 1 to 74 wherein the composition is in a dosage form selected from the group consisting of an inhalation dosage form, an oral dosage form, and a parenteral dosage form.

76. The method or pharmaceutical composition of clause 75 wherein the composition is in a parenteral dosage form and the parenteral dosage form is selected from the group consisting of an intradermal dosage form, a subcutaneous dosage form, an intramuscular dosage form, an intraperitoneal dosage form, an intravenous dosage form, and an intrathecal dosage form.

77. The composition of clause 59 or 74 in the form of a lyophilizate.

78. The composition of any one of clauses 45 to 54, 57 to 69, or 72 to 77 in the form of a solid.

79. A kit comprising a sterile vial, the composition of any one of clauses 45 to 78, and instructions for use describing use of the composition for treating a patient with amyotrophic lateral sclerosis.

80. The kit of clause 79 wherein the compound or composition is in the form of a reconstitutable lyophilizate.

81. The kit of clause 79 or 80 wherein the dose of the compound is in the range of 1 to 5 μg/kg of patient body weight.

82. The kit of any one of clauses 79 to 81 wherein the purity of the compound is at least 99 percent based on weight percent.

83. The kit of any one of clauses 79 to 82 wherein the compound or the composition is in a parenteral dosage form.

84. The kit of clause 83 wherein the parenteral dosage form is selected from the group consisting of an intradermal dosage form, a subcutaneous dosage form, an intramuscular dosage form, an intraperitoneal dosage form, an intravenous dosage form, and an intrathecal dosage form.

85. The kit of any one of clauses 79 to 84 wherein the composition further comprises a pharmaceutically acceptable carrier.

86. The kit of clause 85 wherein the pharmaceutically acceptable carrier is a liquid carrier selected from the group consisting of saline, glucose, alcohols, glycols, esters, amides, and a combination thereof.

87. Use of the composition of any one of clauses 45 to 78 for the manufacture of a medicament for treating amyotrophic lateral sclerosis.

88. The pharmaceutical composition of any one of clauses 45 to 78 for use in treating amyotrophic lateral sclerosis.

89. The method of any one of clauses 12, 33, or 34 wherein the nucleic acid is delivered to the patient in a viral vector and the viral vector is a lentiviral vector.

90. The method or composition of any one of clauses 1 to 89 wherein administration of the composition increases the survival of the patient by 90 days or greater.

91. The method or composition of any one of clauses 1 to 90 wherein the patient has a mutation in the SOD1 gene.

92. The method or composition of any one of clauses 1 to 91 wherein the purity of the compound is at least 90 percent based on weight percent.

93. The method of any one of clauses 1 to 44 wherein the expression of a proinflammatory marker is decreased.

94. The method of clause 93 wherein the proinflammatory marker is selected from the group consisting of CD68, CD86, and NOS.

95. A method for inhibiting the expression or the activity of NF-κB in microglia or macrophages to inhibit motor neuron death, the method comprising the steps of
    contacting the microglia or macrophages with a composition comprising an effective amount of an exogenous compound that decreases the expression or the activity of NF-κB in the microglia or the macrophages; and
    inhibiting motor neuron death.

96. The method of clause 95 wherein the expression of NF-κB is decreased in microglia.

97. The method of clause 95 wherein the expression of NF-κB is decreased in macrophages.

98. The method of any one of clauses 95 to 97 wherein the composition comprises an aqueous solution.

99. The method of any one of clauses 95 to 98 wherein the compound is selected from the group consisting of a drug, a peptide, and a nucleic acid.

100. The method of clause 99 wherein the compound is a nucleic acid.

101. The method of clause 100 wherein the nucleic acid functions by RNA interference or is an antisense RNA molecule.

102. The method of clause 100 wherein the nucleic acid is selected from the group consisting of an siRNA, an miRNA, and an shRNA.

103. The method of clause 100 wherein the nucleic acid is an shRNA.

104. The method of any one clauses 100 to 103 wherein the nucleic acid is delivered in a bacterial vector or in a viral vector.

105. The method of any one of clauses 100 to 104 wherein the nucleic acid has the sequence of SEQ ID NO: 1 or SEQ ID NO: 2.

106. A method for treating a patient with amyotrophic lateral sclerosis, the method comprising the steps of
    administering to the patient a first composition comprising an effective amount of a first compound that decreases the expression or the activity of NF-κB in microglia or macrophages of the patient;

administering to the patient a second composition comprising an effective amount of a second compound that decreases the expression of SOD-1 in astrocytes, motor neurons, neurons, and/or oligodendrocytes of the patient; and inhibiting motor neuron death in the patient.

107. A method for inhibiting the expression or activity of NF-κB in microglia or macrophages of a patient with amyotrophic lateral sclerosis and for inhibiting the expression of SOD-1 in the patient, the method comprising the steps of contacting the microglia or macrophages in the patient with a first composition comprising an effective amount of a first compound that decreases the expression or the activity of NF-κB in the microglia or the macrophages in the patient;

contacting the astrocytes in the patient with a second composition comprising an effective amount of a second compound that decreases the expression of SOD-1 in astrocytes, motor neurons, neurons, and/or oligodendrocytes of the patient; and inhibiting motor neuron death.

108. The method of clause 106 or 107 wherein the expression of NF-κB is decreased in microglia.

109. The method of clause 106 or 107 wherein the expression of NF-κB is decreased in macrophages.

110. The method of any one of clauses 106 to 109 wherein the decrease in expression of NF-κB in microglia is effective for reducing the symptoms of amyotrophic lateral sclerosis.

111. The method of any one of clauses 106 to 110 wherein a decrease in the level of expression of NF-κB in astrocytes is not effective for reducing the symptoms of amyotrophic lateral sclerosis.

112. The method of any one of clauses 106 to 111 wherein the composition comprises an aqueous solution.

113. The method of any one of clauses 106 to 112 wherein the first compound is selected from the group consisting of a drug, a peptide, and a nucleic acid.

114. The method of any one of clauses 106 to 113 wherein the second compound is selected from the group consisting of a drug, a peptide, and a nucleic acid.

115. The method of clause 113 or 114 wherein the compound is a nucleic acid.

116. The method of clause 115 wherein the nucleic acid functions by RNA interference or is an antisense RNA molecule.

117. The method of clause 116 wherein the nucleic acid is selected from the group consisting of an siRNA, an miRNA, and an shRNA.

118. The method of clause 117 wherein the nucleic acid is an shRNA.

119. The method of clause 118 wherein the nucleic acid is delivered to the patient in a bacterial vector or in a viral vector.

120. The method of clause 119 wherein the nucleic acid has the sequence of SEQ ID NO: 1 or SEQ ID NO: 2.

121. The method of clause 119 wherein the vector is a viral vector.

122. The method of any one of clauses 106 to 121 wherein the amyotrophic lateral sclerosis is sporadic amyotrophic lateral sclerosis.

123. The method of any one of clauses 106 to 121 wherein the amyotrophic lateral sclerosis is familial amyotrophic lateral sclerosis.

124. The method of any one of clauses 106 to 123 wherein the amount of the compound is in the range of about 1 ng/kg of patient body weight to about 1 mg/kg of patient body weight.

125. The method of any one of clauses 106 to 124 wherein the amount of the compound is in the range of about 1 ng/kg of patient body weight to about 500 ng/kg of patient body weight.

126. The method of any one of clauses 106 to 125 wherein the amount of the compound is in the range of about 1 ng/kg of patient body weight to about 100 ng/kg of patient body weight.

127. The method of any one of clauses 106 to 126 wherein the composition further comprises a carrier, an excipient, or a diluent, or a combination thereof.

128. The method of clause 127 wherein the composition comprises a pharmaceutically acceptable carrier, wherein the pharmaceutically acceptable carrier is a liquid carrier.

129. The method of clause 128 wherein the liquid carrier is selected from the group consisting of saline, glucose, alcohols, glycols, esters, amides, and a combination thereof.

130. The method of any one of clauses 106 to 129 wherein the composition is administered in a single-dose or a multiple-dose regimen.

131. The method of any one of clauses 106 to 130 wherein the composition is in a dosage form selected from the group consisting of an inhalation dosage form, an oral dosage form, and a parenteral dosage form.

132. The method of clause 131 wherein the composition is in a parenteral dosage form and the parenteral dosage form is selected from the group consisting of an intradermal dosage form, a subcutaneous dosage form, an intramuscular dosage form, an intraperitoneal dosage form, an intravenous dosage form, and an intrathecal dosage form.

133. The method of any one of clauses 106 to 132 wherein administration of the first or the second composition increases the survival of the patient by 90 days or greater.

134. The method of any one of clauses 106 to 133 wherein the patient has a mutation in the SOD1 gene.

135. The method of any one of clauses 106 to 134 wherein the purity of the first or the second compound is selected from the group consisting of at least 90 percent, at least 95 percent, at least 96 percent, at least 97 percent, at least 98 percent, at least 99 percent, and at least 99.5 percent.

136. The method of any one of clauses 1 to 44, 75, 76, or 90 to 105 wherein the purity of the compound is selected from the group consisting of at least 90 percent, at least 95 percent, at least 96 percent, at least 97 percent, at least 98 percent, at least 99 percent, and at least 99.5 percent.

137. The method of any one of clauses 106 to 135 wherein the first composition and/or the second composition comprises an aqueous solution.

138. The method of any one of clauses 1 to 44, 75, 76, or 90 to 137 wherein the compound comprises an adeno-associated virus vector.

139. The method of any one of clauses 1 to 44, 75, 76, or 89 to 105 wherein the administration of the compound increases the survival of the patient for a number of days selected from the group consisting of at least 20 days, at least 30 days, at least 35 days, at least 40 days, at least 45 days, at least 50 days, at least 55 days, at least 60 days, at least 65 days, at least 70 days, at least 75 days, at least 80 days, at least 85 days, at least 90 days, at least 95 days, at least 100 days, at least 150 days, at least 200 days, at least 250 days, and at least 300 days compared to a patient who is not treated with the compound.

140. The method of any one of clauses 106 to 132, 134 to 135, or 137 wherein the administration of the first compound or the second compound increases the survival of the patient for a number of days selected from the group consisting of at least 20 days, at least 30 days, at least 35 days, at least 40 days, at least 45 days, at least 50 days, at least 55 days, at least 60 days, at least 65 days, at least 70 days, at least 75 days, at least 80 days, at least 85 days, at least 90 days, at least 95 days, at least 100 days, at least 150 days, at least 200 days, at least 250 days, and at least 300 days compared to a patient who is not treated with the first or the second compound.

Figure 1D:
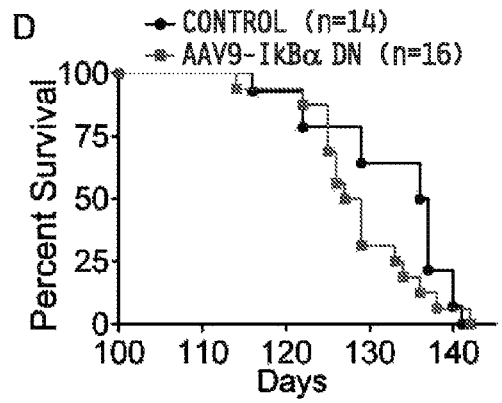
FIG. 1. The NF-κB pathway is activated with disease progression in the SOD1-G93A mouse model and astroglial NF-κB inhibition does not confer neuroprotection.
Figure 1E:
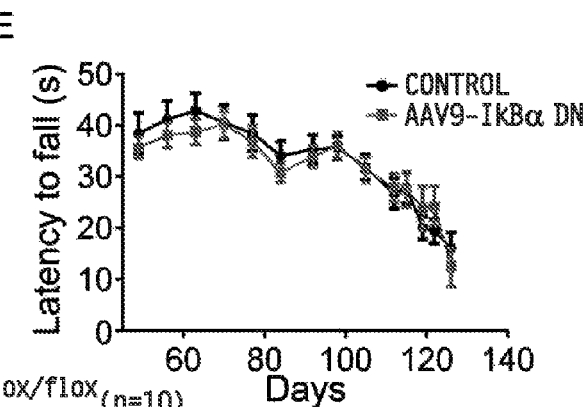

(A) Immunoblot of lumbar spinal cord protein isolated from wild-type mice at 120 days of age and from SOD1-G93A female mice at pre-symptomatic (Pre), onset (Ons), symptomatic (Sym), late-symptomatic (LSym), and end-stage (ES) shows increase in phospho-p65 with disease progression (top). The blot was reprobed for total p65 (middle) and Actin (bottom) as loading controls. n=3 for each time point.

(B) Fold change of the immunoblot in (A). Phospho-p65 was found to be significantly upregulated by 13.7 fold at the late-symptomatic stage and by 8.7 fold at end stage. Band intensities were normalized to p65/Actin.

(C) Immunoblot of protein isolated from astrocytes obtained from late-symptomatic SOD1-G93A and wild-type littermates shows 4.4 fold increase in activated NF-κB.

(D and E) Kaplan-Meier survival curve (D) of SOD1-G93A mice injected with AAV9-DN-ikBa (median survival=128, n=16) and non-injected controls (median survival=136.5, n=14) and motor performance on accelerating rotarod test (E).

(F and G) Kaplan-Meier survival curve (F) of SOD1-G93A; IKKβf/f; GFAP-cre− (median survival=154, n=10) and SOD1-G93A; IKKβf/f; GFAP-cre+ mice (median survival=149, n=14) and motor performance on accelerating rotarod test (G). Error bars represent s.e.m. *, P<0.05, **, P<0.01.

FIG. 2. NF-κB activation occurs predominately in microglia in the SOD1-G93A mouse model.

(A and B) Representative high magnification images of NF-κB-GFP-positive cells (green) in the lumbar ventral horn of late-symptomatic NF-κBEGFP; SOD1-G93A mice. Most predominant GFP+ cells (A) also positive for microglial marker Iba1+ (red). Other GFP+ cells positive for astrocyte maker GFAP (blue) Scale bar=5 microns (A) 20 microns (B).

(C) Immunoblot of protein isolated from primary microglia obtained from late-symptomatic SOD1-G93A mice and WT littermates confirm NF-κB is activated 12.4 fold in SOD1-G93A microglia compared to control littermates. Microglia from 6 mice were pooled together for protein isolation. Fold change determined by phospho-p65 band intensity normalized to p65/Actin.

(D) Immunohistochemistry of lumbar ventral horn of WT; NF-κB-GFP at 120 days, and SOD1-G93A; NF-κB-GFP mice pre-symptomatic, onset, symptomatic, late-symptomatic, and end-stage. NF-κB activation shown by NF-κBEGFP (green) and microglia shown by tomato lectin (red). Scale bar=50 microns.

(E) Quantification of GFP+ cells co-localizing with tomato lectin in lumbar spinal cord sections of SOD1-G93A; NF-κB -GFP mice.

Error bars represent s.e.m. , P<0.01, **, P<0.0001.

FIG. 3. Adult SOD1-G93A microglia are toxic to motor neurons in vitro.

(A and B) Immunocytochemistry of WT and SOD1-G93A microglia for prototypic microglial markers Iba-1, CD11b, F4/80, and astrocytes (GFAP), oligodendrocyte precursors (NG2), and motor neurons (ChAT). Quantification of positive microglial cells per well (B). DAPI (blue) Scale bar=20 microns.

(C) Flow cytometry of adult microglia for CD45 and CD11b.

(D and E) Representative microscopic field (D) and quantification of entire well (E) of surviving Hb9-GFP+ motor neurons after 3 days (72 hours) of co-culture with either WT or SOD1-G93A microglia that were not infected (black bars) or infected with Lv-RFP (dashed bars) or Lv-shRNA-SOD1 (white bars). Scale bar=200 microns (F) Quantification of human SOD1 protein in SOD1-G93A microglia infected with Lv-RFP and Lv-shRNA-SOD1 determined by ELISA.

Error bars represent s.e.m. *, P<0.001, **, P<0.0001.

FIG. 4. Adult SOD1-G93A microglia induce motor neuron death in an NF-κB dependent mechanism in vitro.

(A and B) Representative microscopic fields (A) and entire well counts (B) of Hb9-GFP+ motor neurons after 12 hours and 72 hours in co-culture with WT or SOD1-G93A microglia not infected (black bars), infected with Ad-RFP (dashed bars) or Ad-DNikBα (white bars). MNs co-cultured with either WT; IKKβf/f or SOD1-G93A; IKKβf/f microglia infected with Ad-cre shown with dashed bars. Scale bar=200 microns.

(C and D) Quantification of TNF-α (C) and nitric oxide (D) in the co-culture medium by ELISA. Nitric oxide measured indirectly by sum of nitrate and nitrite.

(E) Quantification of phospho-p65 by ELISA from microglial-MN co-cultures. Phospho-p65 normalized to total levels of p65 determined by ELISA.

Error bars represent s.e.m. **, P<0.0001, *, P<0.001.

FIG. 5. SOD1-G93A microglia induce motor neuron death in an NF-κB dependent mechanism in vivo.

(A) Kaplan-Meier survival curve of SOD1-G93A; IKKβF/wt; CSF1R-cre− (n=22) and SOD1-G93A; IKKβF/wt; CSF-1R-cre+ mice (n=25). Median survival SOD1-G93A; IKKβF/wt; CSF1R-cre−=133 days, SOD1-G93A; IKKβF/wt; CSF-1R-cre+=153 days. Mean survival SOD1-G93A; IKKβF/wt; CSF1R-cre−=134.9±1.4 days, SOD1-G93A; IKKβF/wt; CSF-1R-cre+=153.7±0.9 days, P<0.0001.

(B) Disease onset determined by age at which peak weight was achieved. SOD1-G93A; IKKβF/wt; CSF1R-cre− reached peak onset at 102.8±1.1 days and SOD1-G93A; IKKβF/wt; CSF1R-cre+ mice reached onset at 101.2±1.3 days.

(C) Disease progression defined as time from disease onset to end-stage. SOD1-G93A; IKKβF/wt; CSF1R-cre− had a mean disease progression of 34.8±1.4 days and SOD1-G93A; IKKβF/wt; CSF1R-cre+ had an average disease progression of 51.1±1.7 days.

(D) Immunoblot of lumbar spinal cord protein isolated from WT; IKKβ$^{F/wt}$; CSF1R-cre+, WT; IKKβ$^{F/wt}$; CSF1R-cre−, and end-stage SOD1-G93A; IKKβ$^{F/wt}$; CSF1R-cre−, SOD1-G93A; IKKβ$^{F/wt}$ CSF1R-cre+ mice probed for phospho-p65 (top), total p65, IKKβ, human SOD1 and Actin (bottom). Fold change represents band intensities of phospho-p65 normalized to p65/Actin and IKKβ normalized to Actin.

(E) Immunohistochemistry of Iba1-positive microglia (red) and GFAP-positive astrocytes (green) in the lumbar spinal cords of end-stage SOD1-G93A; IKKβf/wt CSF1R-cre−, and age-matched SOD1-G93A; IKKβf/wt CSF1R-cre+, and WT IKKβf/wt CSF1R-cre+ littermates. Scale bar=200 microns.

(F and G) Quantification of GFAP and Iba-1 signal intensity in SOD1-G93A; IKKβ$^{F/wt}$ CSF1R-cre− and age-matched SOD1-G93A; IKKβ$^{f/wt}$ CSF1R-cre+ immunohistochemistry represented in (E).

FIG. 6. NF-κB inhibition in SOD1-G93A microglia impairs microglial activation to a pro-inflammatory, neurotoxic phenotype.

(A) Immunohistochemistry of CD68 (red) and Iba1 (green) cells in lumbar spinal cord of disease-matched end-stage SOD1-G93A; IKKβF/wt CSF1R-cre− and SOD1-G93A; IKKβF/wt CSF1R-cre+ littermates. Scale bar=200 microns.

(B) Quantification of CD68+/Iba-1+ cells per section of SOD1-G93A; IKKβF/wt CSF1R-cre− and SOD1-G93A; IKKβF/wt CSF1R-cre+.

(C) Immunohistochemistry of iNOS (red) and Iba1 (green) cells in lumbar spinal cord of disease-matched end-stage SOD1-G93A; IKKβF/wt CSF1R-cre− and SOD1-G93A; IKKβF/wt CSF1R-cre+ littermates. Scale bar=20 microns.

(D) Quantification of iNOS+/Iba-1+ cells per section of SOD1-G93A; IKKβF/wt CSF1R-cre− and SOD1-G93A; IKKβF/wt CSF1R-cre+.

(E) Immunohistochemistry of CD86 (red) and Iba1 (green) cells in lumbar spinal cord of disease-matched end-stage SOD1-G93A; IKKβF/wt CSF1R-cre− and SOD1-G93A; IKKβF/wt CSF1R-cre+ littermates. Scale bar=20 microns.

(F) Quantification of CD86+/Iba-1+ cells per section of SOD1-G93A; IKKβF/wt CSF1R-cre− and SOD1-G93A; IKKβF/wt CSF1R-cre+.

FIG. 7. NF-κB activation in microglia induces motor neuron death.

(A and B) Representative microscopic fields (A) and entire well counts (B) of Hb9-GFP+ motor neurons after 1 day (12 hours) and 3 days (72 hours) in co-culture with wild-type microglia (WT) (white bar) or wild-type microglia with constitutively active IKKβ (IKKβCA) (black bar).

(C) Quantification of NF-κB activation (phospho-p65) and normalized to total p65, both determined by ELISA.

(D) Immunoblot of lumbar spinal cord protein from WT and IKKβCA mice. The blot was probed for p-p65 (top), IKKβ (top middle), p65 (bottom middle) and Actin (bottom). p-p65 band intensities normalized to p65/Actin. Fold change determined by densitometry in Image J.

(E) Immunohistochemistry of lumbar spinal cords of WT and IKKβCA littermates at 8 months. Iba1-positive microglia (red), GFAP-positive astrocytes (blue), ChAT-positive MNs (green). Scale bar=100 microns.

(F) Counts of ChAT+ MNs in ventral horn of lumbar spinal cord from 8-month old IKKβCA and WT littermates. (n=3).

(G) Mass of IKKβCA (n=6) and WT littermates (n=8).

(H) Grip strength of IKKβCA (n=6) and WT littermates (n=8).

(I) Immunohistochemistry of lumbar spinal cords of WT and IKKβCA littermates at 4 months and 8 months. Iba1-positive microglia (red), GFAP-positive astrocytes (green), ChAT-positive motor neurons (blue). Scale bar=200 microns.

Figure 8A:
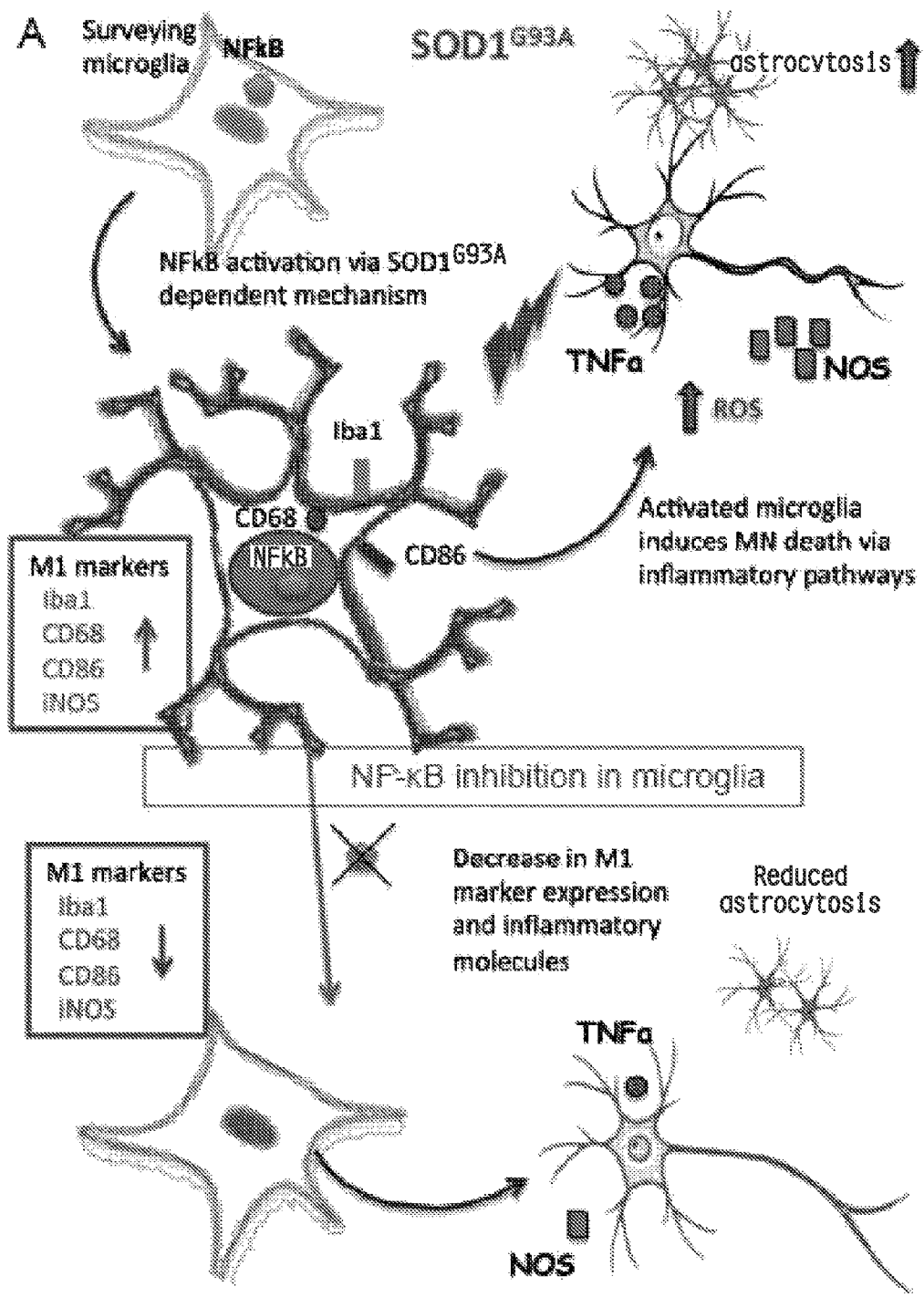
Figure 8B:
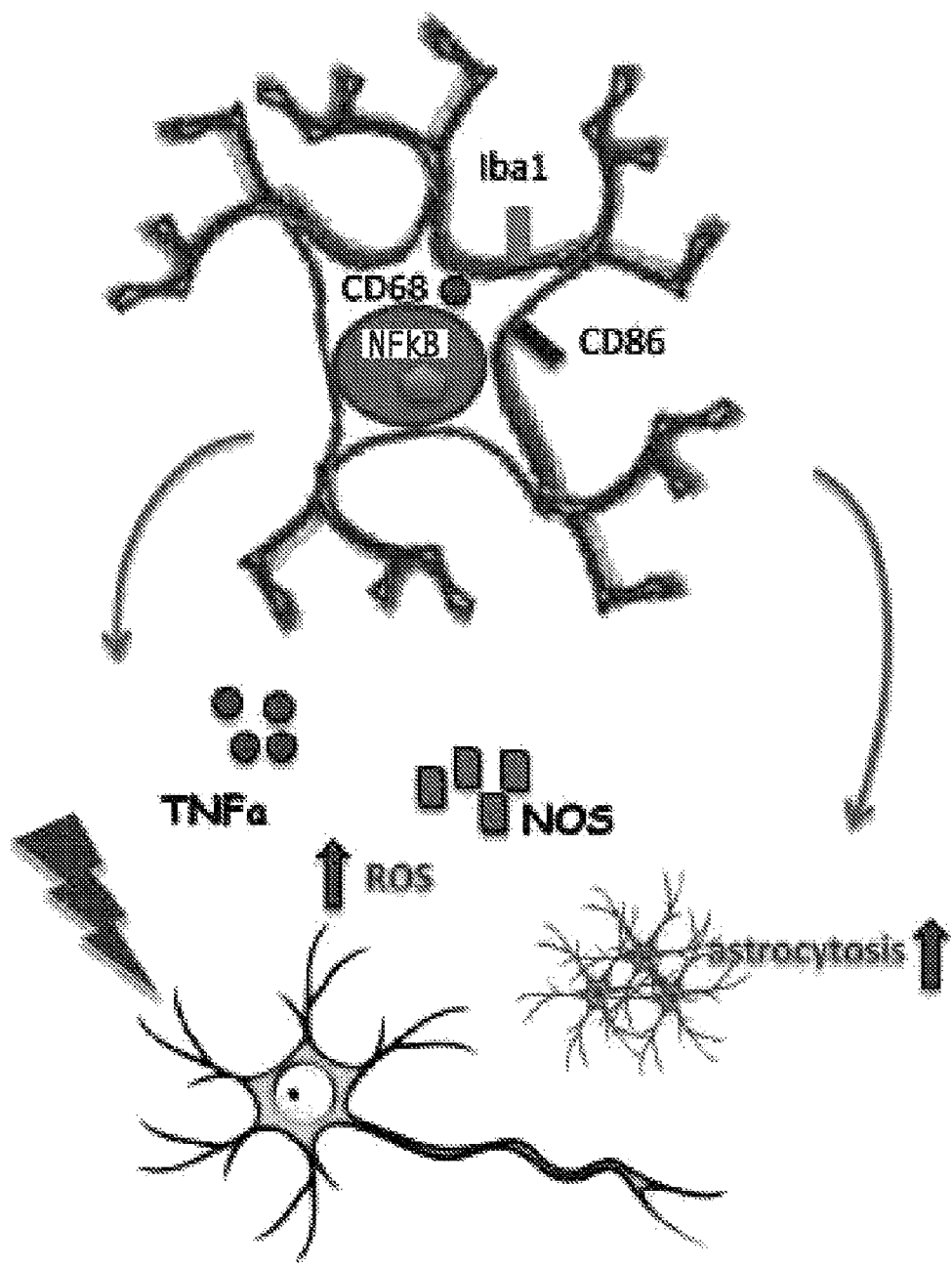

FIG. 8. The classical NF-κB pathway mediates microglial activation and motor neuron death.

(A) Model of the mechanism by which SOD1-G93A microglia induce motor neuron death in ALS. SOD1-G93A microglia initiate the NF-κB pathway by a SOD1-G93A-dependent mechanism leading to activation of microglia, characterized by an increase in Iba-1, CD68, iNOS, and CD86 cellular markers. Subsequently, activated microglia induce motor neuron death via inflammatory pathways. Inhibition of NF-κB in ALS mice blocks microglial activation, down-regulates pro-inflammatory markers, and delays motor neuron death.

(B) Model of IKKβCA mice in which NF-κB is constitutively active only in myeloid cells. Microglia in these mice have shorter, thickened processes and exhibit a pro-inflammatory phenotype characterized by an increase in Iba-1, CD68, iNOS, and CD86 markers. These activated microglia induce motor neuron death in a mutant SOD1-independent mechanism.

FIG. S1. The classical NF-κB pathway is activated in SOD1-G93A mice.

(A) Electrophoretic mobility shift assay of total spinal cord nuclear extracts from 130 day old wild-type mice and end-stage SOD1-G93A mice.

(B) Supershifts of nuclear extract from SOD1-G93A sample #3 and #2. Arrow shows supershifted band from p65 antibody.

(C) and (D) Immunoblot of nuclear extracts probed for p65, p50, and Tubulin.

(E) Immunoblot of lumbar spinal cord protein lysate from wild-type (n=2), late-stage (n=6), and end-stage (n=6) SOD1-G93A mice. The blot was probed for phospho-p65 and reprobed for total p65 (middle) and Actin (bottom) as loading controls.

(F) Fold change of the immunoblot in (A) determined using Image J to measure band intensities of phospho-p65 normalized to p65/Actin. Phospho-p65 is upregulated by 13.4±1.6 fold compared to wild-type at the late-symptomatic stage and by 14.1±4.8 fold at end stage.

FIG. S2. NF-κB inhibition in astrocytes does not confer neuroprotection in vitro or in vivo in the SOD1-G93A mouse model.

(A) Quantification of surviving Hb9-GFP+ motor neurons per well during 6-day co-culture with wild-type (dashed) or SOD1-G93A astrocytes infected with Ad-RFP (black) or Ad-IκBα-SR (gray). (n=3)

(B) Quantification of phospho-p65 by ELISA in wild-type and SOD1-G93A astrocytes infected by Ad-RFP or Ad-IκBα-SR and stimulated with 10 ng/mL TNF-α for 12 hours.

(C and D) Representative images of GFAP-cre-negative and positive Rosa26-Stop$^{Flox}$-CAG-tdTomato mice. Native RFP fluorescence was analyzed for co-localization with immunohistochemical markers for (C) astrocytes (GFAP and EAAT2), microglia (Iba1), and (D) motor neurons (ChAT). Scale bar=100 microns (top) 50 microns (bottom).

(E) Immunoblot of lumbar spinal cord protein isolated from WT; IKKβ$^{f/f}$; GFAP-cre−, WT; IKKβ$^{f/f}$; GFAP-cre+, and symptomatic SOD1-G93A; IKKβ$^{f/f}$; GFAP-cre−, SOD1-G93A; IKKβ$^{f/f}$; GFAP-cre+ mice probed for phospho-p65 (top) and Actin (bottom) confirm reduction in NF-κB activation in cre+ mice. Fold change represents band intensities of phospho-p65/Actin determined by ImageJ.

Error bars represent s.e.m. *, P<0.05; , P<0.01; **, P<0.0001.

FIG. S3. CSF-1R-cre is selectively expressed in microglia in the CNS.

(A and B) Representative images of CSF1R-cre-negative and positive Rosa26-Stop$^{Flox}$-CAG-tdTomato mice. Native RFP fluorescence was analyzed for co-localization with immunohistochemical markers for (A) microglia (Iba-1) and astrocytes (GFAP), and (B) motor neurons (ChAT). Scale bar=100 microns (top) and 10 microns (bottom).

(C) Immunohistochemical analysis of end-stage SOD1-G93A; IKKβ$^{F/wt}$; CSF1R-cre negative and positive mice for IKKβ (red) and IKKγ (green) and tomato lectin (blue). Scale bar=50 microns.

FIG. S4. NF-κB activation in wild-type microglia in vitro induces microglial activation to a pro-inflammatory, neurotoxic phenotype.

(A and B) Quantification of TNF-α (A) and nitric oxide (B) in the co-culture medium by ELISA. Nitric oxide measured indirectly by sum of nitrate and nitrite.

Error bars represent s.e.m. *, P<0.05, **, P<0.01.

FIG. S5. NF-κB activation in wild-type microglia induces microglial activation to a pro-inflammatory, neurotoxic phenotype.

(A) Immunohistochemistry of CD68 (red) and Iba1 (green) cells in lumbar spinal cord of WT and IKKβCA littermates at 4 and 8 months. Scale bar=50 microns.

(B) Immunohistochemistry of CD86 (red) and Iba1 (green) cells in lumbar spinal cord of WT and IKKβCA littermates at 4 and 8 months. Scale bar=20 microns.

(C) Immunohistochemistry of iNOS (red) and Iba1 (green) cells in lumbar spinal cord of WT and IKKβCA littermates at 8 months. Scale bar=10 microns.

Figure 9A:
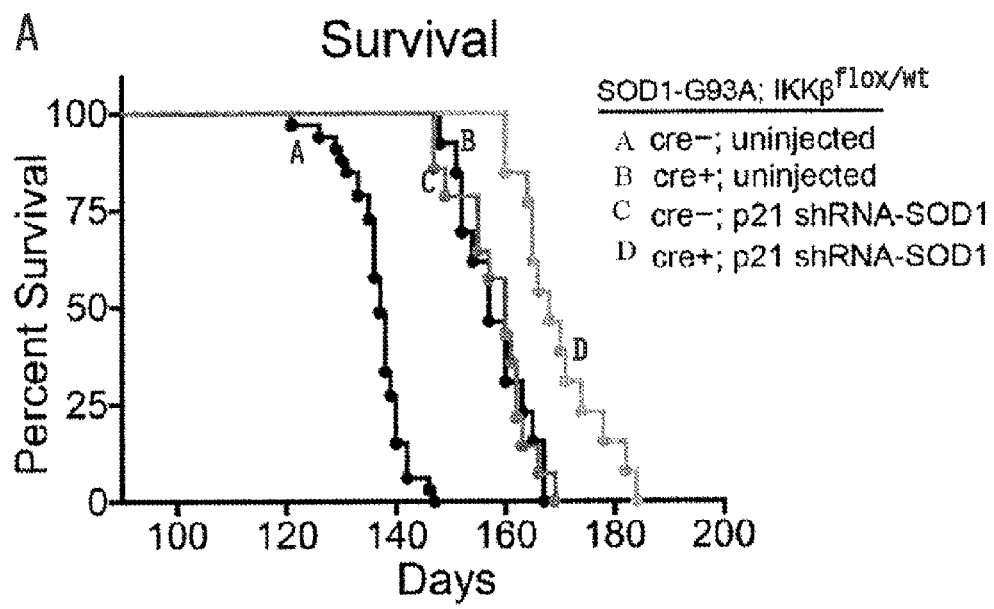

FIG. 9(A). Kaplan-Meier survival curve of SOD1-G93A; IKKβF/wt; CSF1R-cre– (labeled "A", n=33), SOD1-G93A; IKKβF/wt; CSF-1R-cre+ mice (labeled "B", n=13), CSF1R-cre– mice injected with SOD1-shRNA at p21 (labeled "C", n=14), and CSF1R-cre+ mice injected with SOD1-shRNA at p21 (labeled "D", n=13).

Figure 9B:
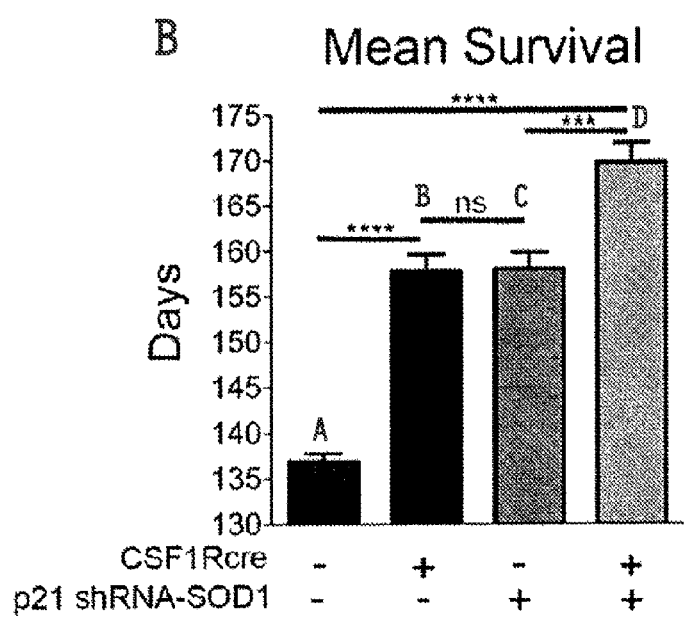

FIG. 9(B). Mean survival graph of SOD1-G93A; IKKβF/wt; CSF1R-cre– (show labeled "A", n=33), SOD1-G93A; IKKβF/wt; CSF-1R-cre+ mice (labeled "B", n=13), CSF1R-cre– mice injected with SOD1-shRNA at p21 (labeled "C", n=14), and CSF1R-cre+ mice injected with SOD1-shRNA at p21 (labeled "D", n=13). Median survival: uninjected CSF1R-cre–=137 days, uninjected CSF-1R-cre+=157 days, CSF1R-cre– p21 injected=160 days, CSF1R-cre+ p21 injected=168 days.

Figure 10A:
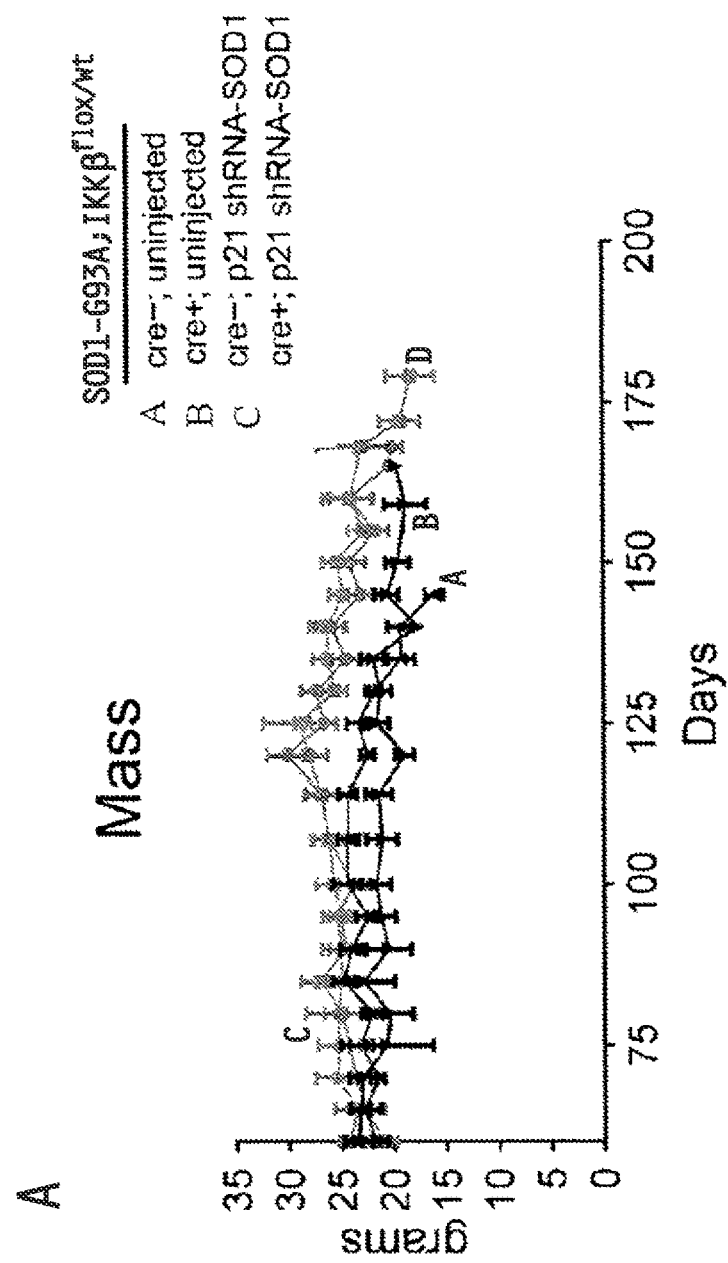

FIG. 10(A). Mass plot of SOD1-G93A; IKKβflox/wt mice: CSF1R-cre–; uninjected (labeled "A"), CSF1R-cre+; uninjected (labeled "B"), CSF1R-cre–; p21 injected (labeled "C"), CSF1R-cre+; p21 injected (labeled "D").

Figures 10B, 10C:
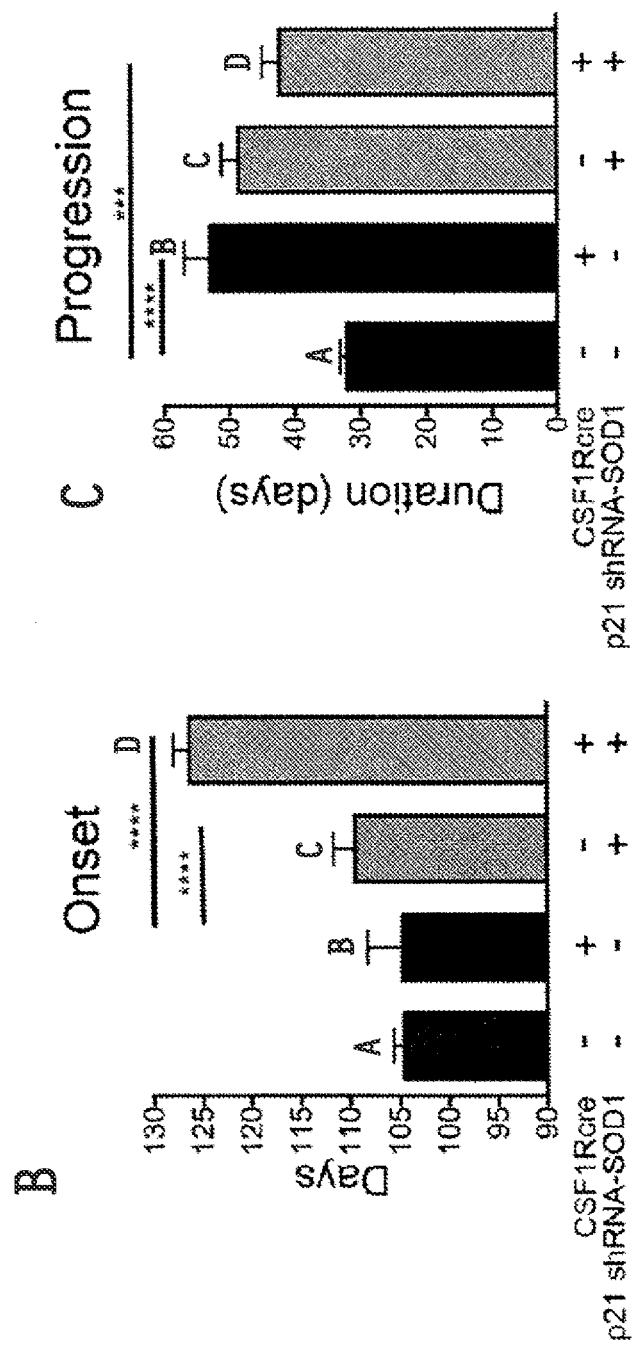

FIG. 10(B). Graph showing onset was delayed in CSF1R-cre+; p21 injected mice (labeled "D") compared to all uninjected (labeled "B" and labeled "D") and CSF1R-cre–; p21 injected mice (labeled "C").

FIG. 10(C). Graph showing disease progression was delayed in all mice with either microglia (labeled "B"), astrocytes (labeled "C"), or both (labeled "D") targeted, compared to untreated controls (labeled "A").

Figure 11A:
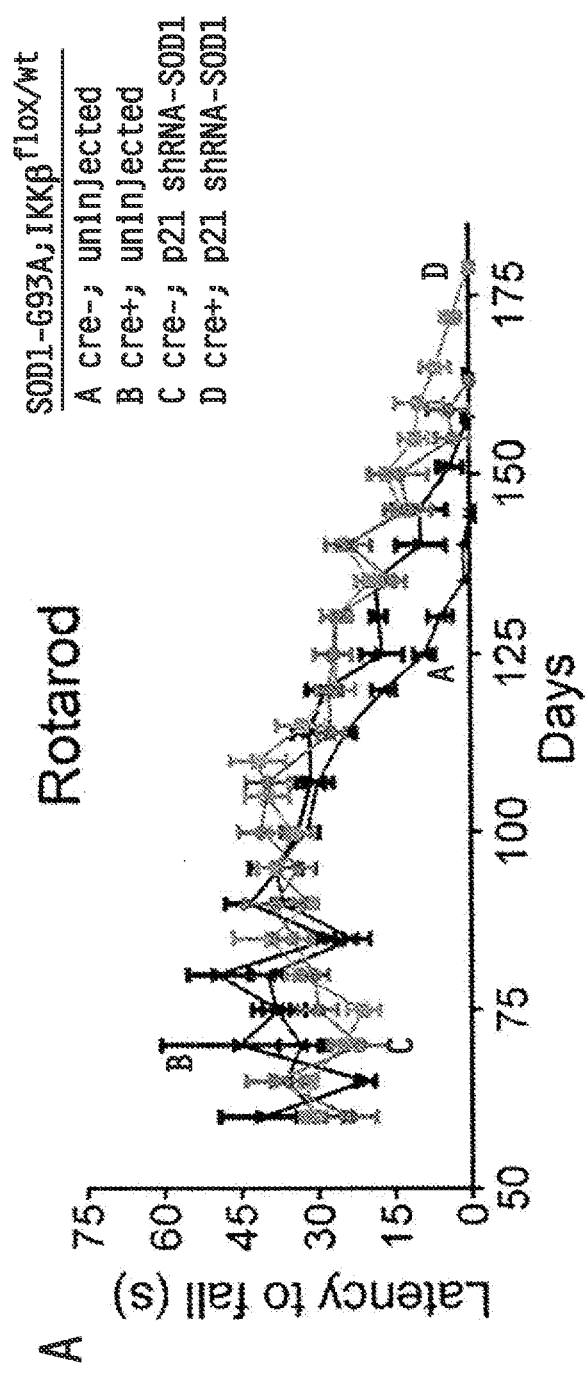

FIG. 11(A). Plot of rotarod testing showing SOD1-G93A; IKKflox/wt; CSF1R-cre+; p1 injected mice (labeled "D") exhibit improved motor performance over untreated controls (labeled "A"). All treated groups (labeled "A", labeled "B", and labeled "C") showed improved motor performance over untreated controls (red).

Figure 11B:
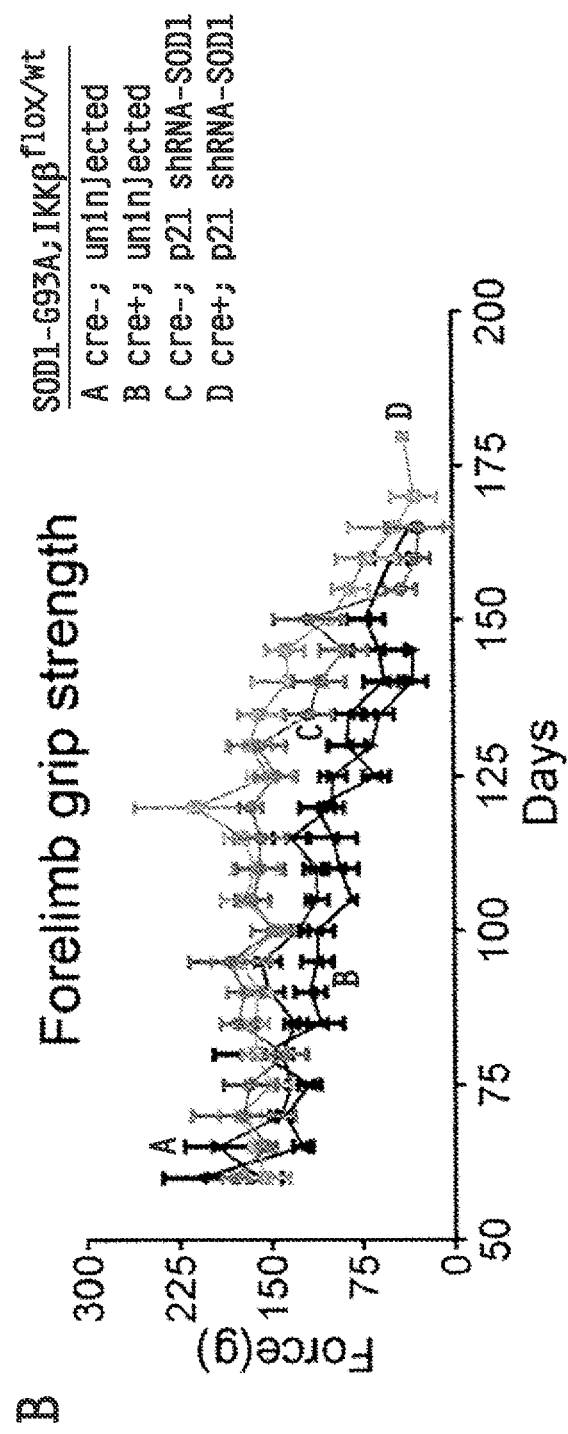

FIG. 11(B). Plot of forelimb grip strength showing SOD1-G93A; IKKflox/wt; CSF1R-cre+; p1 injected mice (labeled "D") exhibit improved motor performance over untreated controls (labeled "A").

Figure 11C:
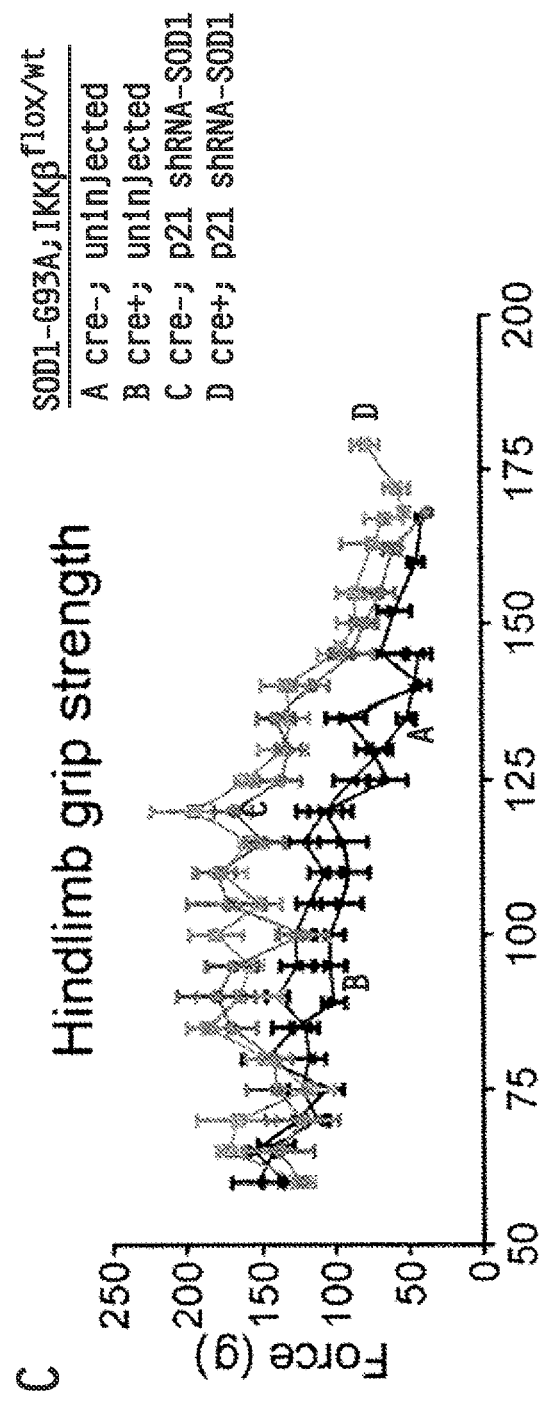

FIG. 11(C). Plot of hind-limb grip strength showing SOD1-G93A; IKKflox/wt; CSF1R-cre+; p1 injected mice (labeled "D") exhibit improved motor performance over untreated controls (labeled "A").

DETAILED DESCRIPTION OF ILLUSTRATIVE EMBODIMENTS

Several embodiments of the invention are described in this Detailed Description section of the patent application and each of the embodiments described in this Detailed Description section of the application applies to each of the embodiments, or combinations thereof, described in the enumerated clauses in the Background and Summary section of the patent application.

In any of the various embodiments described herein, the following features may be present where applicable, providing additional embodiments of the invention. For all of the embodiments, any applicable combination of embodiments is also contemplated.

In one embodiment there is provided a method for treating a patient with amyotrophic lateral sclerosis by decreasing the expression of NF-κB in the patient. The method comprises the steps of administering to the patient a composition comprising an effective amount of a compound that decreases the expression of NF-κB in microglia or macrophages of the patient, and inhibiting motor neuron (MN) death in the patient.

In another embodiment, a method is provided for treating amyotrophic lateral sclerosis by inhibiting the activity of NF-κB in microglia or macrophages of a patient. The method comprises the step of administering to the patient a composition comprising an effective amount of a compound that inhibits the activity of NF-κB in microglia or macrophages of the patient, and inhibiting motor neuron death in the patient.

In yet another embodiment, a method is provided for inhibiting the expression or the activity of NF-κB in microglia or macrophages to inhibit motor neuron death. The method comprises the steps of contacting the microglia or macrophages with a composition comprising an effective amount of an exogenous compound that decreases the expression or the activity of NF-κB in the microglia or the macrophages, and inhibiting motor neuron death.

In still another embodiment, a method is provided for treating a patient with amyotrophic lateral sclerosis. The method comprises the steps of administering to the patient a first composition comprising an effective amount of a first compound that decreases the expression or the activity of NF-κB in microglia or macrophages of the patient, administering to the patient a second composition comprising an effective amount of a second compound that decreases the expression of SOD-1 in astrocytes of the patient, and inhibiting motor neuron death in the patient. In this embodiment, the first and second compositions can contain different compounds (i.e., active agents), and the first and second compounds may, thus, be different compounds (i.e., active agents).

In another illustrative aspect, a method for inhibiting the expression or activity of NF-κB in microglia or macrophages of a patient with amyotrophic lateral sclerosis and for inhibiting the expression of SOD-1 in the patient is provided. The method comprises the steps of contacting the microglia or macrophages in the patient with a first composition comprising an effective amount of a first compound that decreases the expression or the activity of NF-κB in the microglia or the macrophages in the patient, contacting the astrocytes in the patient with a second composition comprising an effective amount of a second compound that decreases the expression of SOD-1 in astrocytes in the patient, and inhibiting motor neuron death. In this embodiment, the first and second compositions can contain different compounds (i.e., active agents), and the first and second compounds may, thus, be different compounds (i.e., active agents).

In any of these method embodiments, or any corresponding use, the decreased expression or activity of NF-κB in microglia or macrophages of the patient, results in an effect on motor neurons of the patient selected from, but not limited to, the group consisting of an increase in the number of motor neurons, a decrease in soma atrophy, and an increase in neurite length after administration of the compound. In various embodiments, the motor neurons may be in the motor cortex, brain stem, or spinal cord of the patient, or combinations thereof. In any of the method embodiments described herein, the decreased expression or activity of NF-κB in microglia or macrophages of the patient may also slow down the progression of amyotrophic lateral sclerosis.

In another illustrative aspect, a pharmaceutical composition is provided. The composition comprises a dosage form of a compound effective to decrease the expression or the activity of NF-κB in microglia or macrophages of a patient with amyotrophic lateral sclerosis. Kits comprising these pharmaceutical compositions are also provided. In other aspects, uses of these pharmaceutical compositions for the manufacture of a medicament for treating amyotrophic lateral sclerosis are provided. In yet other embodiments, these pharmaceutical compositions are provided, for use in treating amyotrophic lateral sclerosis.

In another illustrative aspect of the invention, the methods and uses described herein may decrease the expression of proinflammatory markers. In one embodiment, the proinflammatory markers are selected from the group consisting of CD68, CD86, and NOS.

The methods, kits, uses, and pharmaceutical compositions described herein can be used to treat either sporadic or familial amyotrophic lateral sclerosis, and can be used for both human clinical medicine (i.e., the patient may be a human patient) and veterinary medicine. In one embodiment the patient may have a mutation in the SOD1 gene and may be a human patient. In one embodiment, the compounds described herein that can be used to treat sporadic or familial amyotrophic lateral sclerosis are compounds that are effective to decrease the expression, or reduce the activity, of NF-κB in microglia or macrophages of a patient with amyotrophic lateral sclerosis. In another embodiment, the compounds described herein can be effective to decrease the expression of SOD-1 in astrocytes of the patient. The compounds are selected from the group consisting of drugs, peptides, and nucleic acids, or combinations thereof.

Expression or activity of NF-κB can be reduced, for example, by treatment of a patient with a drug, peptide, or nucleic acid, or a combination thereof, that reduces the expression or the activity of NF-κB in microglia or macrophages of a patient with amyotrophic lateral sclerosis. For example, compounds that reduce activity of NF-κB include Withaferin A. In another embodiment, expression or activity of NF-κB in the microglia or macrophages of a patient with amyotrophic lateral sclerosis can be reduced by treatment of the patient with a pharmaceutical composition comprising a nucleic acid such as an antisense RNA molecule, an siRNA, an shRNA, or an miRNA that inhibits expression or activity of NF-κB. Inhibitors of NF-κB expression or activity also include, for example, Bay 11-7082 [(E)-3-(4-Methylphenylsulfonyl)-2-propenenitrile], Wedelolactone, BMS-345541 [N-(1,8-Dimethylimidazo[1,2-a]quinoxalin-4-yl)-1,2-ethanediamine hydrochloride], Withaferin A, Resveratrol, IMD 0354 [N-(3,5-Bis-trifluoromethylphenyl)-5-chloro-2-hydroxybenzamide], BOT-64 [6,6-Dimethyl-2-(phenylimino)-6,7-dihydro-5H-benzo[1,3]oxathiol-4-one], CAY1065 [3-[(aminocarbonyl)amino]-5-[4-(4-morpholinylmethyl) phenyl]-2-thiophenecarboxamide], Asprin, Sodium Salicylate, NF-κB Essential Modulator binding domain (NBD) peptides, SC-514 [4-amino-[2,3'-bithiophene]-5-carboxamide], AS602868 Ikk2 inhibitor, IKKβ inhibitors that are nucleic acids such as an antisense RNA molecule, an siRNA, an shRNA (e.g., the AAV9-DNiKβ-α construct described herein), or an miRNA, PS-1145 [N-(6-Chloro-9H-pyrido[3,4-b]indol-8-yl)-3-pyridinecarboxamide dihydrochloride], ML120B [N-(6-chloro-7-methoxy-9H-β-carbolin-8-yl)-2-methylnicotinamide], and TPCA-1 [[5-(p-Fluorophenyl)-2-ureido]thiophene-3-carboxamide].

In another embodiment, the expression of SOD-1 in a patient can be reduced, for example, by treatment of the patient with a drug, peptide, or nucleic acid, or a combination thereof, that reduces the expression of SOD-1 in the astrocytes of a patient with amyotrophic lateral sclerosis. For example, compounds that reduce expression of SOD-1 can include pharmaceutical compositions comprising a nucleic acid such as an antisense RNA molecule, an siRNA, an shRNA, or an miRNA that inhibits expression of SOD-1 in astrocytes. In one embodiment, such an shRNA is the shRNA of SEQ ID NO: 1 described herein.

Suitable methods for delivery of antisense RNA molecules, siRNAs, shRNAs, or miRNAs to a patient include bacterial or viral vectors, such as lentiviral vectors or adenovirus vectors. In another embodiment, a suitable method for delivery is an adeno-associated virus vector. Exemplary of such an RNA molecule is the nucleic acid with SEQ ID NO: 1 that targets the human SOD1 transgene in SOD1-$^{G93A}$ microglia shown by the present inventors to efficiently ablate expression of the mutant SOD1 gene in SOD1-$^{G93A}$ microglia, resulting in effective suppression of motor neuron toxicity in motor neurons exposed to the microglia (see Example 18). In another embodiment, a nucleic acid with SEQ ID NO: 2 can be delivered. The RNA molecule of SEQ ID NO: 1 can also inhibit expression of wild type SOD-1.

In accordance with these embodiments, pharmaceutical compositions are provided comprising a purified nucleic acid comprising, or consisting of, a sequence of SEQ ID NO: 1. A purified nucleic acid is also provided comprising a complement of SEQ ID NO: 1, or a sequence that hybridizes under highly stringent conditions to a complement of a sequence consisting of SEQ ID NO: 1. cDNAs are also contemplated and are in accordance with the invention. In accordance with the invention "highly stringent conditions" means hybridization at 65° C. in 5×SSPE and 50% formamide, and washing at 65° C. in 0.5×SSPE. Conditions for high, low, and moderately stringent hybridization are described in Sambrook et al., "Molecular Cloning: A Laboratory Manual", 3rd Edition, Cold Spring Harbor Laboratory Press, (2001), incorporated herein by reference. In some illustrative aspects, hybridization occurs along the full-length of the nucleic acid.

The invention encompasses isolated or substantially purified nucleic acids. An "isolated" or "purified" nucleic acid molecule is substantially free of chemical precursors or other chemicals when chemically synthesized, or is substantially free of cellular material if made by recombinant DNA techniques (e.g., a cDNA). In various embodiments described herein, the nucleic acids for use in the methods, compositions, and kits described herein may be double-stranded (e.g., antisense RNAs) or single-stranded, but the nucleic acids are typically single-stranded.

The nucleic acids for use in the methods, uses, pharmaceutical compositions, and kits described herein can be modified by substitution, deletion, truncation, and/or can be fused with other nucleic acid molecules wherein the resulting nucleic acids hybridize specifically under highly stringent conditions to the complement of SEQ ID NO: 1, for example, and wherein the modified nucleic acids are useful in the methods or uses described herein. Derivatives can also be made such as phosphorothioate, phosphotriester, phosphoramidate, and methylphosphonate derivatives (Goodchild, et al., *Proc. Natl. Acad. Sci.* 83:4143-4146 (1986), incorporated herein by reference).

In another embodiment, nucleic acid molecules are provided having about 60%, about 70%, about 75%, about 80%, about 85%, about 90%, about 95%, about 96%, about 97%, about 98%, or about 99% homology to SEQ ID NO: 1. Determination of percent identity or similarity between sequences can be done, for example, by using the GAP program (Genetics Computer Group, software; now available via Accelrys on http://www.accelrys.com), and alignments can be done using, for example, the ClustalW algorithm (VNTI software, InforMax Inc.). A sequence database can be searched using the nucleic acid sequence of interest. Algorithms for database searching are typically based on the BLAST software (Altschul et al., 1990). In some embodiments, the percent identity can be determined along the full-length of the nucleic acid.

Techniques for synthesizing the nucleic acids described herein, such as SEQ ID NO: 1, or fragments thereof, are well-known in the art and include chemical syntheses. Such techniques are described in Sambrook et al., "Molecular Cloning: A Laboratory Manual", 3rd Edition, Cold Spring Harbor Laboratory Press, (2001), incorporated herein by reference. Nucleic acids for use in the methods described herein can be made commercially. Techniques for purifying or isolating the nucleic acids described herein are well-known in the art. Such techniques are described in Sambrook et al., "Molecular Cloning: A Laboratory Manual", 3rd Edition, Cold Spring Harbor Laboratory Press, (2001), incorporated herein by reference.

In one embodiment, the compounds described herein for ablating expression of NF-κB in microglia or macrophages (i.e., drugs, peptides, or nucleic acids), for inhibiting activity of NF-κB in microglia or macrophages, or for inhibiting expression of SOD-1 in astrocytes may be administered as a formulation in association with one or more pharmaceutically acceptable carriers. The carriers can be excipients. The choice of carrier will to a large extent depend on factors such as the particular mode of administration, the effect of the carrier on solubility and stability, and the nature of the dosage form. Pharmaceutical compositions suitable for the delivery of the compound, or additional therapeutic agents to be administered with the compound, and methods for their preparation will be readily apparent to those skilled in the art. Such compositions and methods for their preparation may be found, for example, in Remington: The Science & Practice of Pharmacy, 21st Edition (Lippincott Williams & Wilkins, 2005), incorporated herein by reference.

In various illustrative embodiments, the compositions and compounds described herein may be in a dosage form selected from the group consisting of an inhalation dosage form, an oral dosage form, and a parenteral dosage form. The parenteral dosage form may be selected from the group consisting of an intradermal dosage form, a subcutaneous dosage form, an intramuscular dosage form, an intraperitoneal dosage form, an intravenous dosage form, and an intrathecal dosage form.

In one embodiment, a pharmaceutically acceptable carrier may be selected from any and all solvents, dispersion media, coatings, antibacterial and antifungal agents, isotonic and absorption delaying agents, and the like, and combinations thereof, that are physiologically compatible. In some embodiments, the carrier is suitable for parenteral administration. Pharmaceutically acceptable carriers include sterile aqueous solutions or dispersions, and sterile powders for the preparation of sterile injectable solutions or dispersions. Supplementary active compounds can also be incorporated into the pharmaceutical compositions of the invention.

In various embodiments, liquid formulations may include suspensions and solutions. Such formulations may comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, such as a lyophilizate. Thus, in one embodiment, the lyophilizate can be a reconstitutable lyophilizate.

In one illustrative aspect, an aqueous suspension may contain the active materials in admixture with appropriate excipients. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally-occurring phosphatide, for example, lecithin; a condensation product of an alkylene oxide with a fatty acid, for example, polyoxyethylene stearate; a condensation product of ethylene oxide with a long chain aliphatic alcohol, for example, heptadecaethyleneoxycetanol; a condensation product of ethylene oxide with a partial ester derived from fatty acids and a hexitol such as polyoxyethylene sorbitol monooleate; or a condensation product of ethylene oxide with a partial ester derived from fatty acids and hexitol anhydrides, for example, polyoxyethylene sorbitan monooleate. The aqueous suspensions may also contain one or more preservatives, for example, ascorbic acid, ethyl, n-propyl, or p-hydroxybenzoate; or one or more coloring agents. In other embodiments, isotonic agents, for example, sugars, polyalcohols such as mannitol, sorbitol, or sodium chloride can be included in the pharmaceutical composition.

In one embodiment the excipient comprises a buffer. In one embodiment, the pH of the buffer is about 5.0 to about 8.0. The buffer may be any acceptable buffer for the indicated pH range and physiological compatibility. In addition a buffer may additionally act as a stabilizer. In one embodiment, the buffer comprises an ascorbate, sorbate, formate, lactate, fumarate, tartrate, glutamate, acetate, citrate, gluconate, histidine, malate, phosphate or succinate buffer.

In one aspect, a compound (i.e., a drug, a peptide, or a nucleic acid), or additional therapeutic agent as described herein, may be administered directly into the blood stream, into muscle, or into an internal organ. Suitable routes for parenteral administration include intravenous, intraarterial, intraperitoneal, intrathecal, epidural, intracerebroventricular, intrasternal, intracranial, intramuscular, and subcutaneous delivery. Suitable means for parenteral administration include needle (including microneedle) injectors, needle-free injectors and infusion techniques. Examples of parenteral dosage forms include aqueous solutions of the active agent, in an isotonic saline, glucose (e.g., 5% glucose solutions), or other well-known pharmaceutically acceptable liquid carriers such as liquid alcohols, glycols, esters, and amides. Prolonged absorption of the injectable compositions can be brought about by including in the composition an agent which delays absorption, for example, monostearate salts and gelatin.

Also contemplated herein are kits comprising the pharmaceutical composition described herein. In another embodiment, a kit comprising a sterile vial, the pharmaceutical composition of any one of the preceding embodiments, and instructions for use describing use of the composition for treating a patient with amyotrophic lateral sclerosis is described.

In another embodiment, the kit of the preceding embodiment wherein the compound or the composition is in the form of a reconstitutable lyophlizate is described.

In another embodiment, any of the preceding kit embodiments wherein the dose of the compound in the pharmaceutical composition is in the range of 1 to 5 µg/kg is described.

In another embodiment, any of the preceding kit embodiments wherein the dose of the compound in the pharmaceutical composition is in the range of 1 to 3 µg/kg is described.

In another embodiment, the kit of any of the preceding kit embodiments is described wherein the purity of the compound is at least 90% based on weight percent. In another embodiment, the kit of any of the preceding embodiments is described wherein the purity of the compound is at least 95% based on weight percent. In another embodiment, the kit of any of the preceding kit embodiments is described wherein the purity of the compound is at least 98% based on weight percent. In another embodiment, the kit of any of the preceding kit embodiments is described wherein the purity of the compound is at least 99% based on weight percent.

In another illustrative aspect, the kit of any of the preceding kit embodiments is described wherein the compound or the composition is in a parenteral dosage form. The parenteral dosage form can be selected from the group consisting of an intradermal dosage form, a subcutaneous dosage form, an intramuscular dosage form, an intraperitoneal dosage form, an intravenous dosage form, and an intrathecal dosage form. In yet another embodiment, the kit can comprise the composition and the composition can further comprise a pharmaceutically acceptable carrier. The pharmaceutically acceptable carrier can be a liquid carrier selected from the group consisting of saline, glucose, alcohols, glycols, esters, amides, and a combination thereof.

Any effective regimen for administering the compound can be used. For example, the compound can be administered as a single dose, or can be divided and administered as a multiple-dose daily regimen. Further, a staggered regimen, for example, one to five days per week can be used as an alternative to daily treatment, and for the purpose of the pharmaceutical compositions, kits, methods, and uses described herein, such intermittent or staggered daily regimen is considered to be equivalent to every day treatment and is contemplated. In one illustrative embodiment the patient is treated with multiple injections of the compound to eliminate the disease state (i.e., amyotrophic lateral sclerosis) or to reduce or stabilize the symptoms of disease. In one embodiment, the patient is injected multiple times (preferably about 2 up to about 50 times), for example, at 12-72 hour intervals or at 48-72 hour intervals. Additional injections of the compound can be administered to the patient at an interval of days or months after the initial injections(s) of the compound, and the additional injections can prevent recurrence of the disease or can prevent an increase in the severity of the symptoms of disease.

In one embodiment, administration of the compounds and compositions described herein according to the methods and uses of the invention may increase the survival of the patient by 90 days or greater. In another embodiment, administration of the compounds and compositions described herein according to the methods and uses of the invention may increase the survival of the patient by at least 20 days, at least 30 days, at least 35 days, at least 40 days, at least 45 days, at least 50 days, at least 55 days, at least 60 days, at least 65 days, at least 70 days, at least 75 days, at least 80 days, at least 85 days, at least 90 days, at least 95 days, at least 100 days, at least 150 days, at least 200 days, at least 250 days, or at least 300 days as compared to a patient who does not receive the treatment described herein.

The unitary daily dosage of the compound can vary significantly depending on the patient condition, the purity of the compound and its route of administration and tissue distribution, and the possibility of co-usage of other therapeutic treatments. The effective amount to be administered to a patient is based on body surface area, mass, and physician assessment of patient condition. Effective doses can range, for example, from about 1 ng/kg to about 1 mg/kg, from about 1 µg/kg to about 500 µg/kg, and from about 1 µg/kg to about 100 µg/kg. These doses are based on an average patient weight of about 70 kg, and the kg are kg of patient body weight (mass). In one embodiment, the compound or pharmaceutical composition is in a multidose form. In another embodiment, the compound or pharmaceutical composition is a single dose form (i.e., a unit dose form or a dosage unit).

In one embodiment, the compound can be administered in a dose of from about 1.0 ng/kg to about 1000 µg/kg, from about 10 ng/kg to about 1000 µg/kg, from about 50 ng/kg to about 1000 µg/kg, from about 100 ng/kg to about 1000 µg/kg, from about 500 ng/kg to about 1000 µg/kg, from about 1 ng/kg to about 500 µg/kg, from about 1 ng/kg to about 100 µg/kg, from about 1 µg/kg to about 50 µg/kg, from about 1 µg/kg to about 10 µg/kg, from about 5 µg/kg to about 500 µg/kg, from about 10 µg/kg to about 100 µg/kg, from about 20 µg/kg to about 200 µg/kg, from about 10 µg/kg to about 500 µg/kg, or from about 50 µg/kg to about 500 µg/kg. The total dose may be administered in single or divided doses and may, at the physician's discretion, fall outside of the typical range given herein. These dosages are based on an average patient weight of about 70 kg and the "kg" are kilograms of patient body weight. The physician will readily be able to determine doses for subjects whose weight falls outside this range, such as infants and the elderly.

In another embodiment, the compound can be administered at a dose of from about 1 µg/m$^2$ to about 500 mg/m$^2$, from about 1 µg/m$^2$ to about 300 mg/m$^2$, or from about 100 µg/m$^2$ to about 200 mg/m$^2$. In other embodiments, the compound can be administered at a dose of from about 1 mg/m$^2$ to about 500 mg/m$^2$, from about 1 mg/m$^2$ to about 300 mg/m$^2$, from about 1 mg/m$^2$ to about 200 mg/m$^2$, from about 1 mg/m$^2$ to about 100 mg/m$^2$, from about 1 mg/m$^2$ to about 50 mg/m$^2$, or from about 1 mg/m$^2$ to about 600 mg/m$^2$. The total dose may be administered in single or divided doses and may, at the physician's discretion, fall outside of the typical range given herein. These dosages are based on m$^2$ of body surface area.

In the embodiment where a viral vector is used, the titer may be about $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, or $1\times10^{14}$, DNase resistant particles per ml. In another embodiment, the pharmaceutical compositions and/or dosage forms of the compound for administration are prepared from compounds with a purity of at least about 90%, or about 95%, or about 96%, or about 97%, or about 98%, or about 99%, or about 99.5%. In another embodiment, pharmaceutical compositions and or dosage forms of the compound for administration are prepared from compounds with a purity of at least 90%, or 95%, or 96%, or 97%, or 98%, or 99%, or 99.5%. The purity of the compound may be measured using any conventional technique, including various chromatography or spectroscopic techniques, such as high pressure or high performance liquid chromatography, nuclear magnetic resonance spectroscopy, TLC, UV absorbance spectroscopy, fluorescence spectroscopy, and the like.

As used herein, purity determinations may be based on weight percentage, mole percentage, and the like. In addition, purity determinations may be based on the absence or substantial absence of certain predetermined components. It is also to be understood that purity determinations are applicable to solutions of the compounds and pharmaceutical compositions prepared by the methods described herein. In those instances, purity measurements, including weight percentage and mole percentage measurements, are related to the components of the solution exclusive of the solvent. In another embodiment, the compound or the pharmaceutical composition is provided in a sterile container (e.g., a vial) or package, for example, an ampoule or a sealed vial.

In another embodiment, the methods, pharmaceutical compositions, uses, and kits, described herein include the following examples. The examples further illustrate additional features of the various embodiments of the invention described herein. However, it is to be understood that the examples are illustrative and are not to be construed as limiting other embodiments of the invention described herein. In addition, it is appreciated that other variations of the examples are included in the various embodiments of the invention described herein.

EXAMPLE 1

Transgenic Mice

All procedures were performed in accordance with the NIH Guidelines on the care and use of vertebrate animals and approved by the Institutional Animal Care and Use Committee of the Research Institute at Nationwide Children's Hospital. Animals were housed under light:dark (12:12 h) cycle and provided with food and water ad libitum. Transgenic female B6SJ/L(SOD1-G93A)1Gur/J mice and non-transgenic littermates (Jackson Laboratories) were utilized for time course immunoblot studies and primary cell isolations. Transgenic male B6SJ/L(SOD1-G93A)1Gur/J mice were used for breeding with other transgenic lines. SOD1 transgene copy number was confirmed by real time PCR. SOD1-G93A-NFκBEGFP reporter mice were generated by breeding SOD1-G93A mice to C57BL/6 NFκBEGFP mice (Christian Jobin) (Magness et al., 2004). SOD1-G93A; hGFAP-cre; IKKβflox/flox were generated by breeding SOD1-G93A mice to FVB hGFAP-cre (Jackson Labs) mice that had been crossed to C57B116 IKKβflox/flox mice (Li et al., 2003). SOD1-G93A; CSF-1R-icre; IKKβflox/wt were generated by breeding SOD1-G93A mice to C57BL/6 CSF-1R-cre mice (Deng et al., 2010) that had been bred to IKKβflox/flox mice. CSF1R-cre; IKKβCA were generated by breeding CSF-1R cre mice to C57BL/6 Rosa26-StopFloxIKKβCA mice (Jackson Labs). Cre specificity was confirmed by crossing cre lines to C57BL/6 Rosa26-StopFlox-CAG-tdTomato mice and assessed for tdTomato expression by immunohistochemistry. See FIGS. 8A and 8B. Genotypes were determined by qualitative PCR using the primers in Table 1.

TABLE 1

| Genotyping Qualitative PCR | | |
|---|---|---|
| PCR | Forward Primer (5'-3') | Reverse Primer (5'-3') |
| human SOD1 | CAT CAG CCC TAA TCC ATC TGA | CGC GAC TAA CAA TCA AAG TGA |
| Control for SOD1 reaction | CTA GGC CAC AGA ATT GAA AGA TCT | GTA GGT GGA AAT TCT AGC ATC ATC C |
| IKKβ | GTC ATT TCC ACA GCC CTG TGA | CCT TGT CCT ATA GAA GCA CAA |
| iCre | CAGGGCCTTCTCCACACCAGC | CTGGCTGTGAAGACCATC |
| Cre | GGACATGTTCAGGGATCGCCAGG CG | CGACGATGAAAGCATGTTTAGCT G |
| eGFP | GAG CTG AAG GGC ATC GAC TTC AAG | GGA CTG GGT GCT CAG GTA GTG G |
| negative for eGFP | TCAGGCCCACCTAGTCAGAT | AAAGCGGTCTGAGGAGGAA |
| tdTomato | CTG TTC CTG TAC GGC ATG G | GGC ATT AAA GCA GCG TAT CC |
| negative for tdTomato | AAG GGA GCT GCA GTG GAG TA | CCG AAA ATC TGT GGG AAG TC |

| Copy Number Real Time PCR | | | |
|---|---|---|---|
| Primer | 5' label | Sequence 5' -> 3' | 3' Label |
| Transgenic Probe | 6-FAM | CTG CAT CTG GTT CTT GCA AAA CAC CA | Zen probe with Iowa Black |
| Internal Positive Control Forward | — | CAC GTG GGC TCC AGC ATT | — |
| Internal Positive Control Reverse | — | TCA CCA TTC ATT TCT GCC TTT G | — |
| hSOD1 Forward | — | GGG AAG CTG TTG TCC CAA G | — |

TABLE 1-continued

| | | |
|---|---|---|
| hSOD1 Reverse | — | CAA GGG GAG GTA AAA GAG AGC |
| Internal Control Probe | Cy5 | CCA ATG GTC GGG CAC Black Hole Quencher 2 TGC TCA A |

EXAMPLE 2

AAV9-DNiκBα Injections

Adult tail vein injections were performed on 60 day old SOD1-G93A mice as previously described (Foust et al., 2009; 2010) with a 100 µl viral solution containing a mixture of PBS and 4×10$^{12}$ DNase-resistant particles of scAAV9-CB-DNiκBα or scAAV9-CB-GFP (Virapur).

EXAMPLE 3

Disease Scoring and Behavior Analysis

Mice were classified as "pre-symtomatic" when they displayed no clinical symptoms of disease and had not reached peak weight. "Onset" was determined at the stage mice reach peak body weight. The "symptomatic" stage was determined when mice had lost 10 percent of their body weight and displayed motor impairment tremors or impaired hindlimb splay reflex. The "late-symptomatic" stage was determined when mice experienced pronounced hindlimb paralysis, but could reach food and water using forelimbs. "End-stage" was determined when animals could no longer "right" themselves within 30 seconds after the animal was placed on its back.

Testing of motor function using a rotarod device (Columbus Instruments, Columbus, OH) began at 50 days of age. Each session consisted of three trials that were averaged on the elevated accelerating rotarod beginning at 5 r.p.m./minute measuring the time the mouse was able to remain on the rod. Grip strength measurements for hindlimb were tested weekly using a grip strength meter (Columbus Instruments). Each session consisted of three tests per animal and values were averaged.

EXAMPLE 4

Isolation and Culture of Adult Primary Astrocytes

Adult astrocyte cultures from brains of SOD1-G93A and wild-type littermates were prepared and purified as previously described (*Noble and Mayer-Proschel*, 1998) with minor modifications. Enzymatically dissociated cells were cultured for 2 to 3 weeks, and then shaken overnight when the cells reached confluency. Adhered confluent astrocytes were treated with cytosine arabinose (20 µM) for 48 hours to kill rapidly dividing cells. Astrocytes were cultured in DMEM GlutaMAX™ DMEM+10% FBS+N2+antibiotic-antimycotic (all from Life Technologies).

EXAMPLE 5

Isolation and Culture of Adult Primary Microglia

Adult microglia were isolated from brains of SOD1-G93A and wild-type littermates as previously described (Moussaud and Draheim, 2010) with minor modifications. Four-month old SOD1-G93A and wild-type littermate mice were deeply anesthetized and perfused transcardially with ice-cold Ringers solution (Fisher Scientific). Brains that appeared to not be fully exsanguinated were discarded. Brains were fragmented with a scalpel and incubated with an enzymatic solution containing papain for 60 minutes at 37° C., 5% CO2. The papain solution was quenched with 20% FBS in HBSS and centrifuged for 4 minutes at 200 g. The pellet was resuspended in 2 ml of 0.5 mg/ml DNase I (Worthington Biochemical) in HBSS and incubated for 5 min at room temperature. The brain tissue was gently disrupted with fire-polished Pasteur pipettes and then filtered through a 70 micron cell strainer (Fischer Scientific) and centrifuged at 200 g for 4 minutes. The resulting pellet was then resuspended in 20 ml of 20% isotonic Percoll (GE healthcare) in HBSS. 20 mL of pure HBSS was carefully laid on top the percoll layer and centrifugation was performed at 200 g for 20 min with slow acceleration and no brake. The interphase layer containing myelin and cell debris was discarded, and the pellet containing the mixed glial cell population was washed once with HBSS and suspended in Dulbecco's modified Eagle's/F12 medium with GlutaMAX™ (DMEM/F12) supplemented with 10% heat inactivated FBS, antibiotic-antimycotic (all from Life Technologies) and 5 ng/ml of carrier-free murine recombinant granulocyte and macrophage colony stimulating factor (GM-CSF) (R&D systems). The cell suspension from four mouse brains were plated on a 15 cm$^2$ plate (Corning) coated with poly-1-lysine (Sigma) and maintained in culture at 37° C. in a 95% air/5% CO2. The medium was replaced every 3 days until the cells reached confluency (after approximately 2 weeks). After the glial layer becomes confluent, microglia form a non-adherent, floating cell layer that can be collected, replated, and cultured for an extended period of time. After collecting the floating layer, microglia were incubated for 3 days without GM-CSF before re-plating for co-culture with motor neurons. Collected microglia were characterized by immunocytochemistry and flow cytometry (antibodies are listed in Table 2). Direct isolation of microglia for western blot analysis was performed as previously described (Cardona et al., 2006; Henry et al., 2009).

TABLE 2

| Western blot | | |
|---|---|---|
| Phospho-p65 | 1:500 | Cell Signaling |
| p65 | 1:500 | Cell Signaling |
| Beta-Actin | 1:1000 | Cell Signaling |
| IKK-beta | 1:125 | Imgenex |
| Immunohistochemistry | | |
| GFP | 1:400 | Abcam |
| Tomato Lectin | 1:300 | Vector Laboratories |
| GFAP | 1:500 | Abcam |
| Iba-1 | 1:400 | Wako |
| CD68 | 1:100 | AbDserotec |
| CD86 | 1:100 | Millipore |
| iNOS | 1:100 | Sigma |
| IKK-gamma | 1:100 | Cell Signaling |
| IKK-beta | 1:100 | Imgenex |

TABLE 2-continued

| Immunocytochemistry | | |
|---|---|---|
| CD11b | 1:200 | AbDserotec |
| F4/80 | 1:100 | AbDserotec |
| NG2 | 1:200 | Millipore |
| ChAT | 1:100 | Millipore |
| Iba-1 | 1:500 | Wako |
| GFAP | 1:200 | Abcam |
| Flow Cytometry | | |
| APC-CD11b | 1:50 | eBiosciences |
| PE-CD45 | 1:25 | eBiosciences |
|  | 1:50 |  |
| CD16/32 | 1:25 | eBiosciences |
| EMSA supershift and nuclear western blots | | |
| p65 | 1:1000 | Santa Cruz Biotechnology |
| p50 | 1:1000 | Santa Cruz Biotechnology |
| c-Rel | 1:1000 | Santa Cruz Biotechnology |
| Rel-B | 1:1000 | Santa Cruz Biotechnology |
| IgG | | |

EXAMPLE 6

Flow Cytometry of Microglia Cultures

Flow cytometric analysis of microglial cell surface markers was performed by first blocking Fc receptors with anti-CD16/CD32 antibody (eBiosciences, CA). Next, cells were incubated with anti-CD11b APC, anti-CD45 FITC (eBiosciences). Expression of these surface receptors was determined by flow cytometry using a Becton-Dickinson LSR II Cytometer. Ten thousand events were collected and microglia incubated with isotype control were used as a negative control. Flow data were analyzed using FlowJo software (Tree Star, San Carlos, Calif.).

EXAMPLE 7

Motor Neuron Differentiation

Mouse embryonic stem cells expressing GFP driven by the Hb9 promoter (HBG3 cells) were cultured on primary mouse embryonic fibroblasts (Millipore) and differentiated to motor neurons with the addition of 2 µM retinoic acid (Sigma) and 2 µM purmorphamine (Calbiochem). After 5 days of differentiation, the embryoid bodies were dissociated and sorted for GFP on a FACSVantage/DiVa sorter (Becton Dickinson).

EXAMPLE 8

Microglia/Motor Neuron Co-Culture

Hb9-GFP+ motor neurons were plated in 96-well plates coated with laminin (5 µg/ml, Invitrogen) at a density of 6,000 cells per well. The day after microglia were plated on top of motor neurons at a density of 35,000 cells per well in motor neuron media (DMEM:F12 (Invitrogen), 5% horse serum, 2% N2 (Invitrogen), 2% B27 (Invitrogen)+GDNF (10 ng/ml, Invitrogen), BDNF (10 ng/ml, Invitrogen), CNTF (10 ng/ml, Invitrogen)). The co-culture plate was imaged each day by the IN Cell Analyzer 6000 (GE Healthcare). Images were processed and analyzed using IN Cell Developer Toolbox 1.9 and IN Cell Analyzer Workstation 3.7 software (GE Healthcare) to quantify number of surviving GFP+ motor neurons per well.

EXAMPLE 9

Virus Production

Transgenic SOD1 expression in microglia was knocked down by lentiviral transduction expressing short interfering RNA sequences previously described (Haidet-Phillips et al., 2011; Miller et al., 2006). Lentivirus SOD1-shRNA and scramble-shRNA were produced by transient transfection into HEK293 cells using calcium phosphate, followed by supernatant viral purification by ultracentrifugation. Adenoviral vectors (Ad-RFP, Ad-cre, Ad-DNiκBα, and Ad-IκBα-SR) were purchased from Vector Biolabs. Microglia were infected with an MOI of 25 overnight, then washed with HBSS and incubated 3 days before co-culture with motor neurons.

EXAMPLE 10

Western Blot

Cells and tissues were homogenized in Tissue Protein Extraction Reagent (Pierce) with EDTA, Complete protease inhibitor (Roche) and Phospho-STOP (Roche). The samples were run on NuPAGE Novex 4-12% Bis-Tris polyacrilamide gels and transferred to a PVDF membrane (Life Technologies). Blots were blocked in 5% milk powder, 0.5% BSA in PBS-Tween for 1 h, and then incubated for overnight at 4° C. with primary antibody. Bound primary antibody was detected by horseradish peroxidase conjugated secondary antibody followed by chemiluminescence (ECL Western Blot Substrate, Pierce). Antibodies are listed in Table 2.

EXAMPLE 11

Immunohistochemistry

Animals were deeply anesthetized with a lethal dose of Xylazene/Ketamine and perfused transcardially with saline, then 4% paraformaldehyde. Spinal cords were sectioned 40 µm thick using a vibrating blade microtome (Leica microsystems). Sections were incubated for 2 h at room temperature in TBS+1% Triton-X+10% donkey serum. Samples were incubated for 72 h at 4° C. with primary antibodies, followed by 2 h incubation at RT with secondary antibodies. All images were captured on a Zeiss confocal microscope (Carl Zeiss Microscopy, Thornwood, NY, USA). Antibodies are listed in Table 2. For quantification of MNs and microglia, lumbar spinal cords were sectioned 40 µm thick from the end of thoracic level 14 to sacral level 1. For MN counts lumbar spinal cord sections were selected every $5^{th}$ section from the first identifiable L1 section through L6 and sections were selected every $8^{th}$ section for microglial quantification.

EXAMPLE 12

ELISAs

TNFα Quantikine ELISA kit (R&D Systems) was used according to manufacturer instructions to quantify the TNFα concentration in co-culture medium. Nitric oxide levels in the co-culture medium were determined using the Total Nitric Oxide and Nitrate/Nitrite Parameter Kit (R&D Systems) according to manufacturer instructions. Co-culture medium was collected, centrifuged for 2 minutes at 200 g, and 50 µL of medium was added to each well for analysis. Phospho-p65 and Total p65 ELISA kits were used according to manufacturer instructions to quantify NF-κB activation in cell lysates (Cell Signaling). All conditions were tested in triplicate.

EXAMPLE 13

Statistical Analyses

For all statistical tests Graph Pad Prism 6 software (La Jolla, Calif.) was used. Statistical analyses of mean differences between groups was performed by either Student's t-test or one-way ANOVA, followed by a Bonferroni post hoc analysis depending on the number of variables in each experiment. All p-values and n values are indicated in the Brief Description of the Drawings.

EXAMPLE 14

NF-κB Activation with Disease Progression in the SOD1-G93A Mouse

In order to gain insight into NF-κB regulation in ALS, EMSA analysis was performed on whole spinal cord nuclear lysates from the SOD1-G93A mouse model. NF-κB DNA binding activity was found to be increased in end-stage ALS mice compared to wild-type littermates (FIG. S1A). Supershift EMSAs and nuclear western anlayses revealed the binding contribution of the p65 and p50 subunits of NF-κB (FIG. 1B) and no binding contribution of the the c-Rel or RelB subunits (FIGS. S1B, S1C, and S1D). To investigate the extent of classical NF-κB (p65/p50) activation in the SOD1-G93A mouse model at different stages of disease, whole lumbar spinal cord protein was analyzed for phospho-p65 (active form of NF-κB) from three SOD1-G93A female mice at the pre-symptomatic stage (pre-SYM), disease onset, symptomatic (SYM), late-symptomatic (late-SYM), and end-stage (ES). As disease progressed in ALS animals, phospho-p65 levels increased modestly from pre-SYM to SYM, although fold changes were not statistically significant. However, at late-SYM phospho-p65 levels were 13.7-fold greater in SOD1-G93A mice compared to wild-types and 8.7-fold greater than wild-type at ES (FIGS. 1A and 1B).

In order to determine whether the increase in phospho-p65 levels observed at late-SYM stages is statistically different compared to the levels at ES, lumbar spinal cord lysates were analyzed from additional late-SYM (n=6) and ES SOD1-G93A mice (n=6). The experiments revealed that there is no statistical difference in NF-κB activation between late-SYM and ES (FIGS. S1E and S1F). To determine the contribution of astrocytes to this increase, primary astrocytes were isolated from the spinal cords of wild-type and SOD1-G93A mice at the late-SYM stage. Western blot analysis showed a 4.4-fold increase in phospho-p65 in ALS astrocytes compared to wild-type (FIG. 1C).

EXAMPLE 15

NF-κB Inhibition in Astrocytes Does Not Confer Neuroprotection In Vitro or In Vivo To determine the relevance of NF-κB activation to astrocyte-mediated MN death in ALS, NF-κB inhibition was tested in an in vitro co-culture model of familial ALS. An embryonic stem cell line containing an Hb9-GFP reporter was utilized, which has been shown to recapitulate aspects of MN pathology and cell death when co-cultured with ALS glia (Di Giorgio et al., 2007; Haidet-Phillips et al., 2011; Nagai et al., 2007). Additionally, the Hb9-GFP reporter allows for purification of MNs by fluorescence activated cell sorting (FACS) and easy visualization of these MNs in co-culture with astrocyes (Wichterle et al., 2002). After 5 days in co-culture, the number of MNs present on SOD1-G93A astrocytes was statistically reduced by 49% compared to the MNs surviving on wild-type astrocytes (FIG. S2A). To test the role of NF-κB in SOD1-G93A astrocytes, an adenovirus was utilized expressing the transdominant super repressor inhibitor of NF-κB (IκBα-SR) which is resistant to phosphorylation-induced degradation, thus inhibiting nuclear translocation and transactivation function of NF-κB (Wang et al., 1999). Adenoviral vectors were capable of targeting nearly 100% of astrocytes in vitro (data not shown) (Miranda et al., 2012). However, overexpression of IκBα-SR in SOD1-G93A astrocytes did not rescue MN death in vitro despite decreasing phospho-p65 levels (FIGS. S2A and S2B). In fact, there were less MNs surviving after 4 days in co-culture with SOD1-G93A astrocytes overexpressing IκBα-SR compared to SOD1-G93A astrocytes, however significance was lost on subsequent days (300.7±10.8 and 192.0±22.0, P<0.01) (FIG. S2A).

NF-κB inhibition was also tested in vivo using two independent, cell-type-specific approaches: viral-mediated gene delivery and transgenic cre-lox recombination. SOD1-G93A mice were injected with adeno-associated viral vector serotype 9 (AAV9) to deliver IκBαSR. Mice were injected at postnatal day 60 to preferentially target >50% astrocytes in the CNS (Foust et al., 2008; 2013). Overexpression of IκBα-SR in astrocytes utilizing AAV9 did not alter survival nor improve motor performance in the SOD1-G93A mice compared to non-injected controls (FIGS. 1D and E) or SOD1-G93A mice injected with AAV9-GFP (Foust 2013).

To transgenically inhibit NF-κB in astrocytes in SOD1-G93A mice, SOD1-G93A mice were mated to mice with conditional mutants of IKKβ (IKKβ$^{f/f}$), which have exon 3 of the ikbkb (IKKβ) gene flanked by loxP sites (Li et al., 2003; Park et al., 2002). These mice were then crossed to a mouse strain expressing cre recombinase under the regulation of the astrocytic glial fibrillary acidic protein (GFAP) promoter, thus ablating IKKβ and downstream NF-κB activity specifically in astrocytes.

Figure 1F:
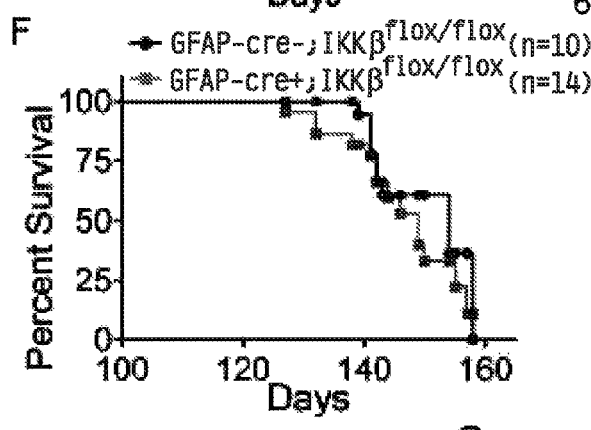
Figure 1G:
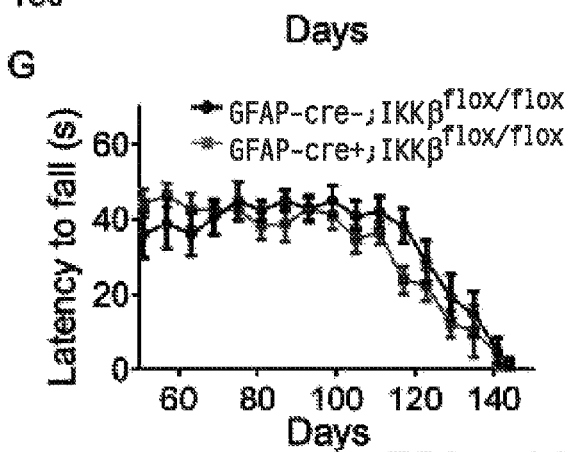

Confirmation that cre expression was restricted to GFAP-expressing astrocytes in the spinal cord was completed by crossing GFAP-cre mice to a Rosa26 line that expresses tdTomato (RFP) in all cre-expressing cells (FIG. S2C). Robust RFP expression was observed in GFAP+ and EAAT2+ cells (FIG. S2D); RFP expression was absent in Iba-1+ microglia as well as in ChAT+ neurons in the spinal cord (FIG. S2C). Immunoblot of lumbar spinal cord protein from WT; IKKβ$^{f/f}$ and SOD1; IKKβ$^{f/f}$ mice demonstrated a 58% reduction in phospho-p65 levels in SOD1; IKKβ$^{f/f}$; GFAP-cre+ mice compared to SOD1 cre– mice at the symptomatic stage of disease (FIG. S2E). Despite the reduction in phospho-p65, motor impairment and survival in the SOD1;IKKβ$^{f/f}$;GFAP-cre+ mice were not improved compared to GFAP-cre– negative controls (FIGS. 1F and 1G). These findings are consistent with a recent study crossing ALS mice to a strain overexpressing IκBα-SR under the GFAP promoter where no extension in survival or motor performance was observed (Crosio et al., 2011).

EXAMPLE 16

NF-κB Activation Occurs Predominately in Microglia

Figure 2A:
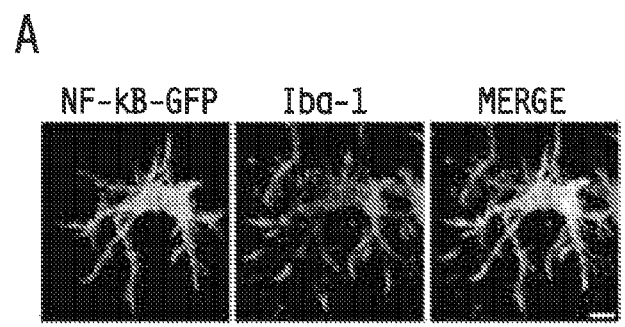
Figure 2B:
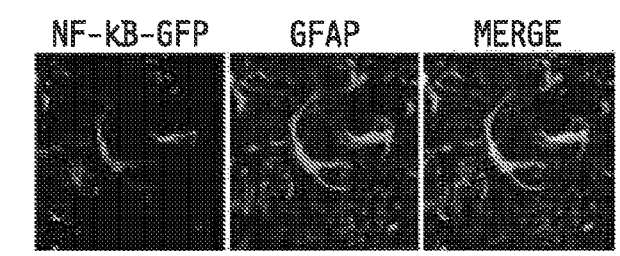
Figure 2C:
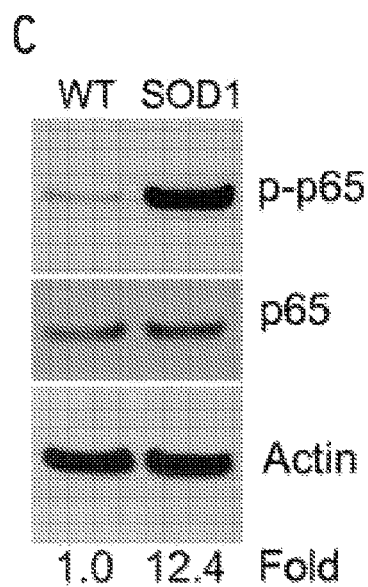
Figure 2E:
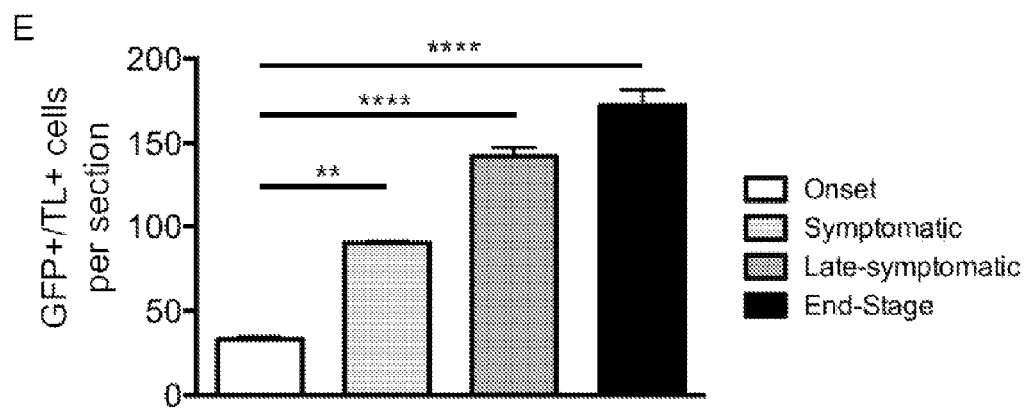

To evaluate whether astrocytes are the main or only cells contributing to the increase in lumbar NF-κB activation, SOD1-G93A mice were crossed to an NF-κB-GFP reporter mouse strain that expresses GFP under the control of NF-κB cis elements (Magness et al., 2004). Since robust NF-κB activation in SOD1-G93A was evident at late stages of disease in lumbar spinal cord protein, lumbar spinal cord sections were analyzed from late-symptomatic SOD1; NF-κB-GFP mice for GFP expression. A population of bright GFP+ cells was observed and was identified as microglia by overlapping Iba-1 staining (FIG. 2A). A dim GFP+ population of GFAP+ astrocytes (FIG. 2B) was also observed. These findings were confirmed by analyzing phospho-p65 levels in protein from microglia isolated from late-symptomatic SOD1-G93A mice. Phospho-p65 was 12.4 fold greater in SOD1-G93A microglia than WT microglia (FIG. 2C).

EXAMPLE 17

Time Course of NF-κB Activation

To determine the time course of NF-κB activation in microglia as disease progressed, immunohistochemistry was performed of SOD1; NF-κB-GFP lumbar spinal cord sections at pre-symptomatic, onset, symptomatic, late-symptomatic, and at end-stage. GFP+ cells were observed at disease onset with an increase in the number and GFP intensity as disease progressed. Furthermore, the majority of GFP+ cells co-localized with a marker for microglia (tomato lectin) suggesting NF-κB activation coincides with microglial activation and gliosis (FIGS. 2D and E). These data reveal that microglia contribute to the robust NF-κB activation that occurs during ALS disease progression.

EXAMPLE 18

Adult SOD1-G93A Microglia are Toxic to Motor Neurons In Vitro

Figure 3A:
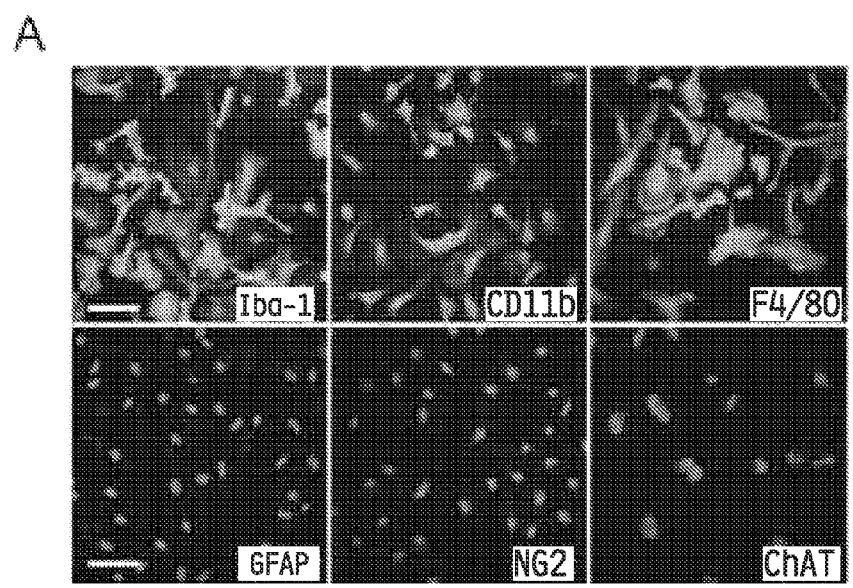
Figure 3B:
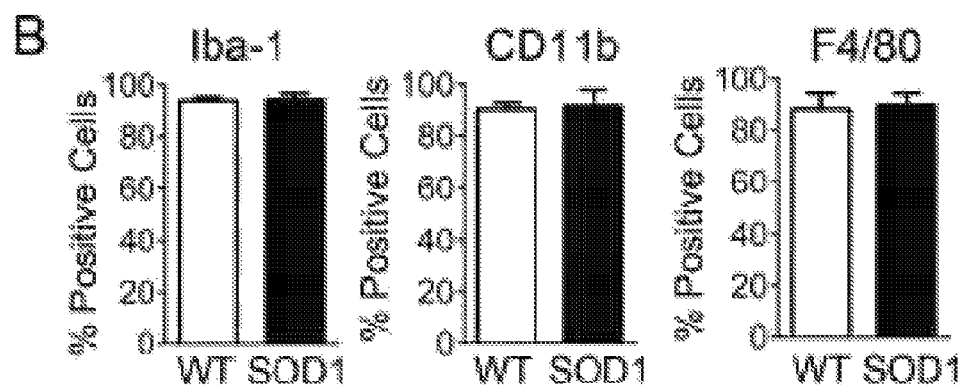
Figure 3C:
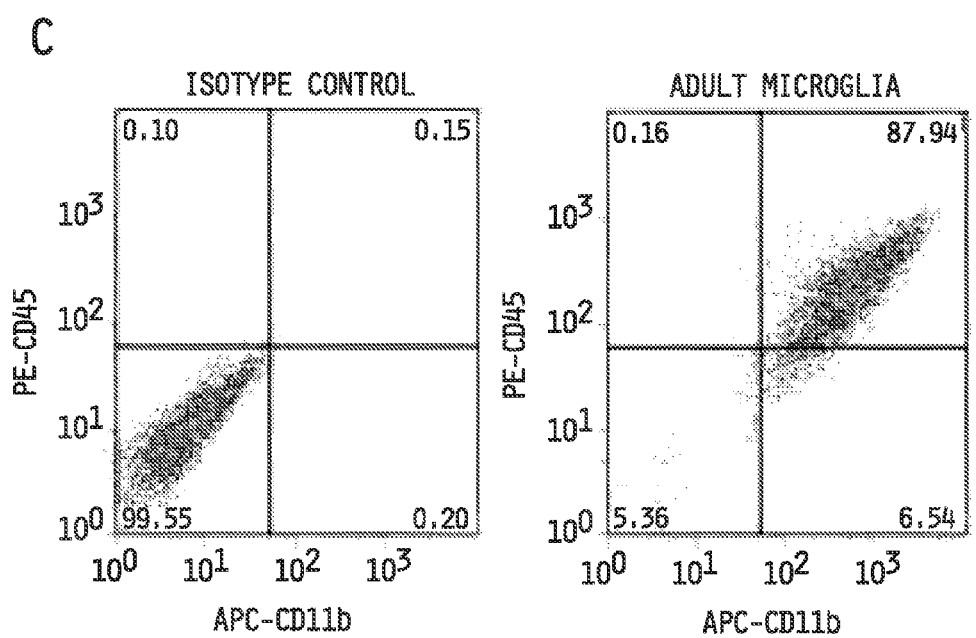

To further study the mechanisms by which microglia mediate motor neuron death in ALS and the possible contribution of NF-κB activation in this process, an in vitro co-culture model of ALS was established. Elegant studies have demonstrated that mutant SOD1 microglia isolated from neonatal mice induce approximately an 18% decrease in motor neuron survival compared to wild-type microglia (Xiao et al., 2007). Since motor neuron toxicity in this model is modest, it is possible that these young cells were not recapitulating important aspects of the adult-onset neurodegenerative disease. Therefore, a co-culture utilizing primary adult microglia isolated from symptomatic ALS mice was established. A previously described method that combines density separation and culture selection was used (Moussaud and Draheim, 2010). Briefly, brains from SOD1-G93A mice and wild-type littermates were mechanically and enzymatically dissociated and subjected to a percoll gradient to obtain a mixed population of glial cells. Once the glial cells were plated and reached confluency, microglia detached from the plate, floated into the medium and could be collected. Immunocytochemical characterization of the adult microglia obtained by this method showed over 90% of the microglia obtained by this method are positive for Iba-1, CD11b, and F4/80 and negative for GFAP, ChAT, and NG2 (FIGS. 3A and B). Flow cytometry showed a homogenous CD45+ and CD11b+ population of microglia (FIG. 3C). Thus microglia obtained by this method express all the prototypic microglial markers. No difference was observed in assays when spinal cord or brain-derived microglia were used. Therefore, experiments were performed utilizing brain microglia to decrease the number of animals used.

Figure 3D:
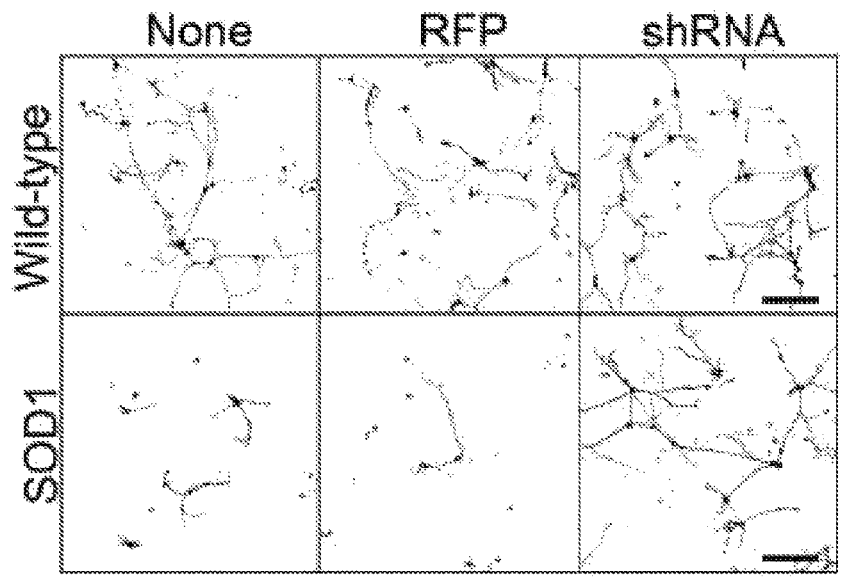
Figure 3E:
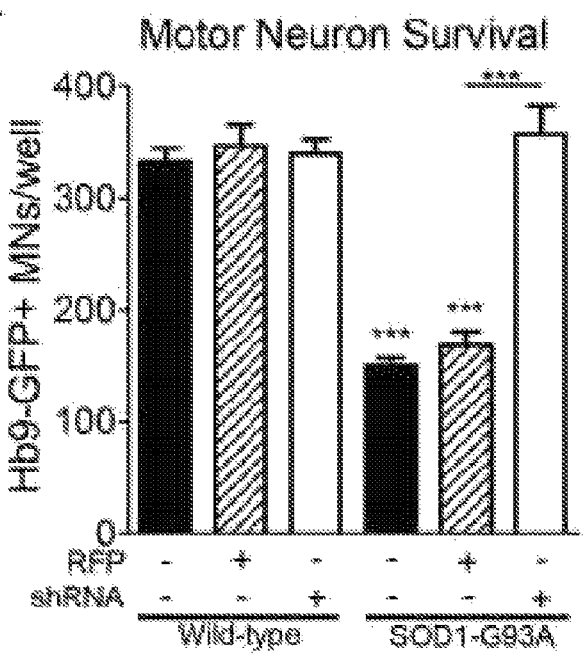

To determine the capacity for SOD1-G93A adult microglia to induce motor neuron death, WT Hb9::GFP+ motor neurons were co-cultured with WT or SOD1-G93A microglia. After 72 hours a 50% statistical decrease was observed in motor neurons when co-cultured with SOD1-G93A microglia compared to microglia isolated from WT littermates (FIGS. 3D and 3E). Additionally, motor neurons co-cultured with SOD1-G93A microglia had dramatically shortened processes (FIG. 3D).

Figure 3F:
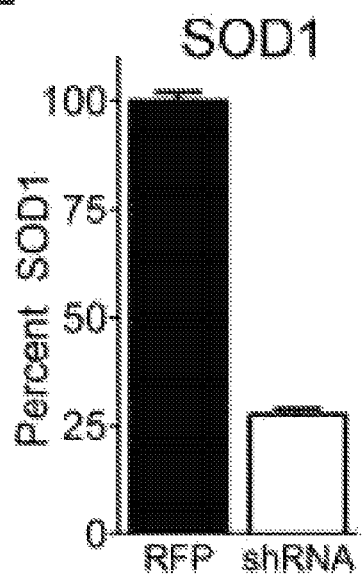

To confirm that this motor neuron death was specific to the causative SOD1 mutation, an shRNA was expressed targeting the human SOD1 transgene in the SOD1-G93A microglia by lentivirus. ELISA results showed that the shRNA reduced mutant protein by 75% (FIG. 3F). When mutant SOD1 protein was reduced in SOD1-G93A microglia, motor neurons survival was completely rescued compared to SOD1-G93A microglia infected with RFP (FIGS. 3D and 3E). The shRNA used had the sequence CATGGATTCCATGTTCATGA (SEQ ID NO: 1).

EXAMPLE 19

Adult SOD1-G93A Microglia Induce Motor Neuron Death in an NF-κB Dependent Mechanism In Vitro To examine whether NF-κB activation in microglia is involved in motor neuron death in the in vitro co-culture model of ALS, two independent approaches were employed to abolish NF-κB activation in microglia. First, DN-iκBα (also referred to as iκβα-SR) was overexpressed via adenovirus (Vector Biolabs, Philadelphia, Pa.) in SOD1-G93A and wild-type microglia. During initial studies using an adenovirus expressing RFP, an MOI of 25 resulted in highly efficient transduction of microglia. The sequence of DN-iκBα (SEQ ID NO: 2) is below.

SEQ ID NO: 2

```
atgtttcagccggcgggccatggccaggattgggcgatggaaggcccgcg cgatggcctgaaaaaagaacgcctggtggatgatcgccatgatgcgggcc tggatgcgatgaaagatgaagaatatgaacagatggtgaaagaactgcgc gaaattcgcctgcagccgcaggaagcgccgctggcggcggaaccgtggaa acagcagctgaccgaagatggcgatagctttctgcatctggcgattattc atgaagaaaaccgctgaccatggaagtgattggccaggtgaaaggcgat ctggcgtttctgaactttcagaacaacctgcagcagacccccgctgcatct ggcggtgattaccaaccagccgggcattgcggaagcgctgctgaaagcgg gctgcgatccggaactgcgcgattttcgcggcaacacccccgctgcatctg gcgtgcgaacagggctgcctggcgagcgtggcggtgctgacccagacctg caccccgcagcatctgcatagcgtgctgcaggcgaccaactataacggcc atacctgcctgcatctggcgagcattcatggctatctggcgattgtggaa catctggtgaccctgggcgcggatgtgaacgcgcaggaaccgtgcaacgg ccgcaccgcgctgcatctggcggtggatctgcagaacccggatctggtga gctgctgctgaaatgcggcgcggatgtgaaccgcgtgacctatcagggc tatagcccgtatcagctgacctggggccgcccgagcacccgcattcagca
```

Figure 4A:
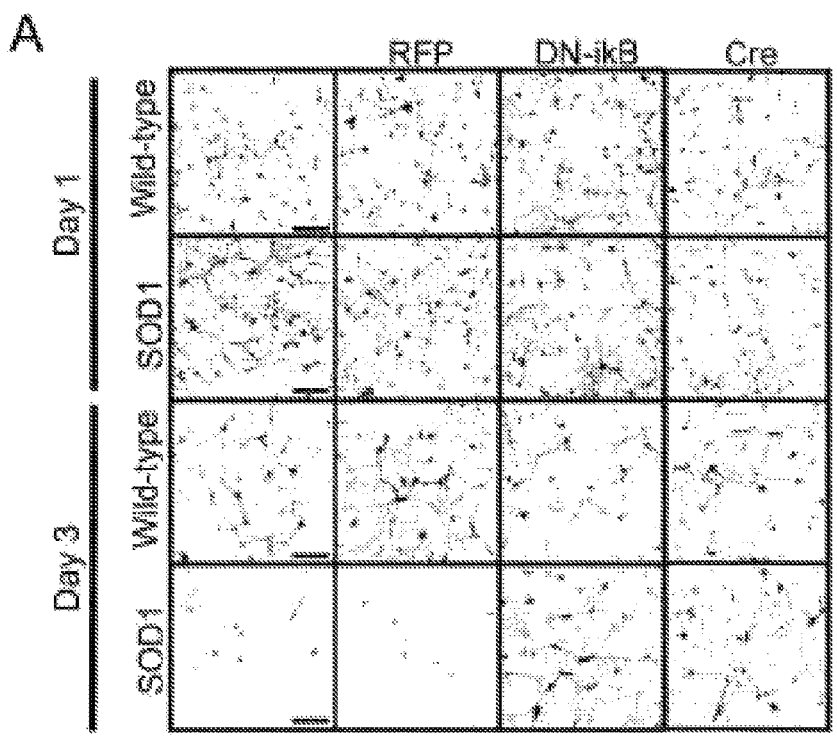
Figure 4B:
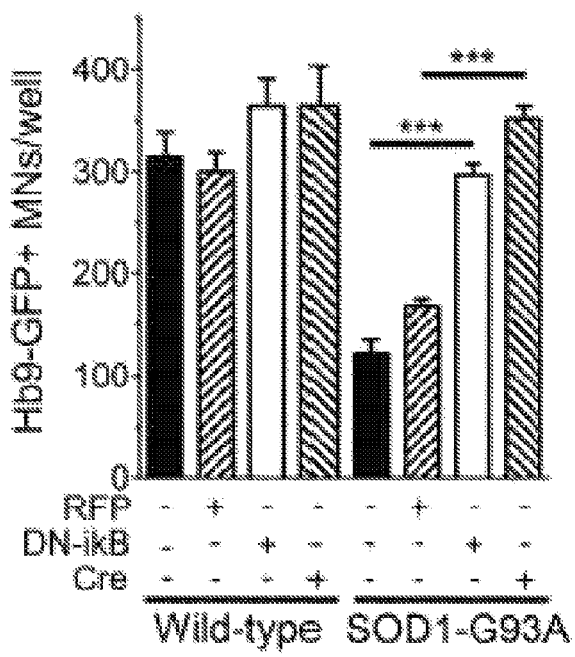

-continued gcagctgggccagctgaccctggaaaacctgcagatgctgccggaaagcg aagatgaagaaagctatgataccgaaagcgaatttaccgaagatgaactg ccgtatgatgattgcgtgtttggcggccagcgcctgaccctg A genetic approach was also used by isolating microglia from SOD1-G93A; IKKβf/f mice and infecting the microglia in vitro with an adenovirus expressing cre recombinase to remove IKKβf/f in microglia post-isolation. After 12 hours, no difference was observed in motor neuron survival or axon length of the motor neurons co-cultured with SOD1-G93A microglia compared to WT controls (FIG. 4A). However, after 72 hours of co-culture a 61% reduction was observed in motor neuron survival and marked reduction in axon length when motor neurons were co-cultured with SOD1-G93A microglia compared to WT (FIG. 4B). Live-imaging of these co-cultures captures the dynamic nature of microglia and rapid motor neuron death induced by SOD1-G93A microglia. Initially, wild-type microglia phagocytosed motor neuron debris which resulted from the FACS sorting and plating. Then, wild-type microglia proceeded to actively survey synapses of motor neurons, not disrupting intact synapses. On the contrary, SOD1-G93A microglia assaulted intact synapses, inducing the death of motor neurons, then phagocytosed the dead neurons. Remarkably, NF-κB inhibition either transgenically or by overexpression of DN-IκBα-SR, fully rescued motor neuron axon length and survival in vitro to wild-type levels (FIGS. 4A and 4B). Live-imaging showed SOD1-G93A microglia with NF-κB inhibition preserved intact motor neurons similar to wild-type microglia.

Figure 4C:
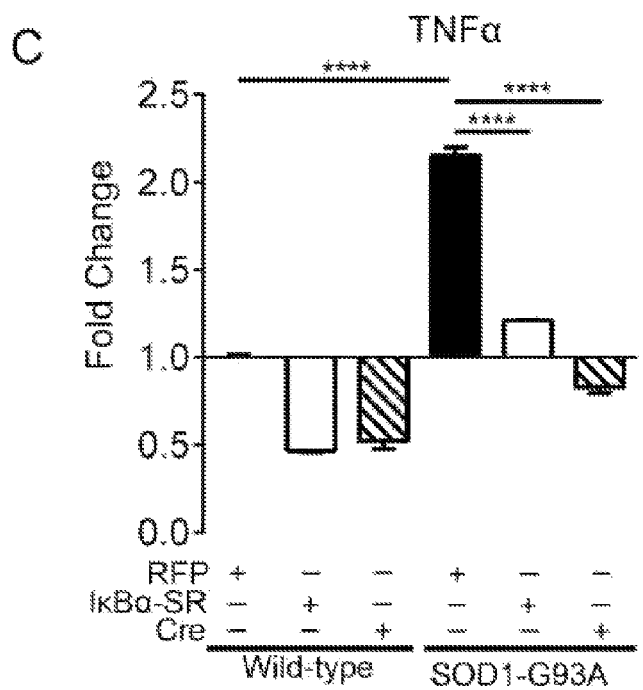
Figure 4D:
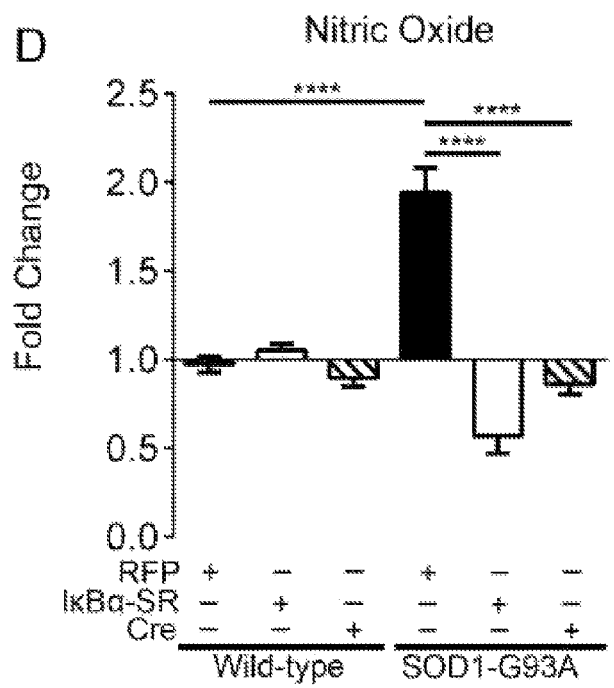
Figure 4E:
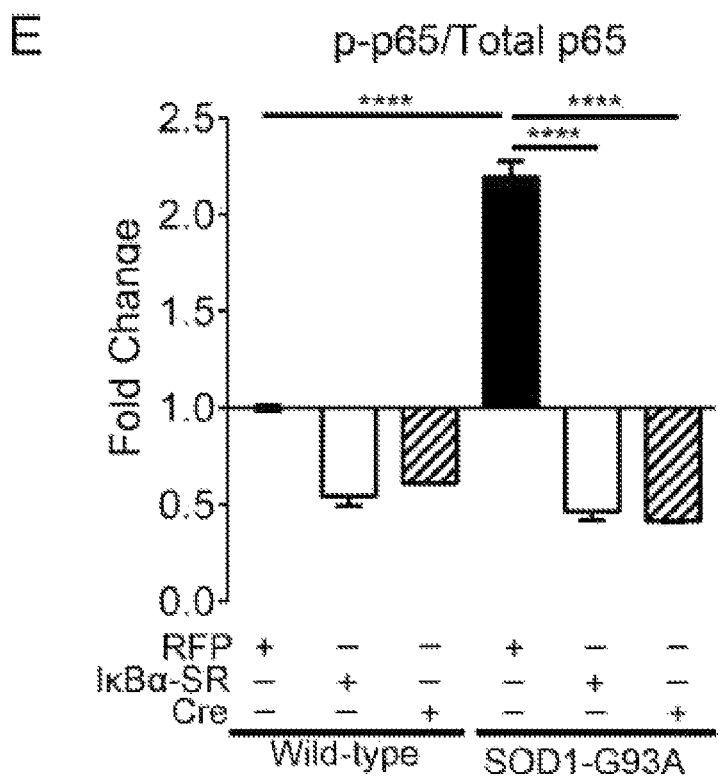

To examine the extent of NF-κB inhibition, nitric oxide (NO) and TNF-α levels were measured in the co-culture medium, both products of NF-κB activation and markers of pro-inflammatory microglia (Ghosh and Karin, 2002). TNF-α levels decreased by 45% and by 64% when NF-κB was inhibited in SOD1-G93A microglia using Ad-DN-iκBα and Ad-cre, respectively (FIG. 4C). Nitric oxide (NO) levels were reduced by 71% and by 56% in SOD1-G93A microglia using Ad-DN-iκBα and Ad-cre, respectively (FIG. 4D). Corresponding with TNF-α and NO levels, phospho-p65 was reduced by 79% and 81% using Ad-IκBα-SR and Ad-cre, respectively, compared to SOD1-G93A microglia (FIG. 4E). These data suggest that SOD1-G93A microglia induce motor neuron death in an NF-κB dependent mechanism.

EXAMPLE 20

SOD1-G93A Microglia Induce Motor Neuron Death in an NF-κB Dependent Mechanism In Vivo Since it was established that (1) NF-κB activation during the disease course in SOD1-G93A mice occurs predominantly in microglia (FIG. 2) and (2) SOD1-G93A microglia appear to utilize an NF-κB-dependent mechanism to induce motor neuron death in vitro (FIG. 4), it was determined whether NF-κB inhibition in microglia would alter the disease course in the SOD1-G93A mouse model. SOD1-G93A; IKKβf/f mice were crossed to mice expressing cre recombinase driven by the promoter for the gene c-fms which encodes Colony stimulating factor receptor 1 (CSF-1R). In reporter mice that express GFP under the regulation of the c-fms promoter, CSF-1R is expressed throughout the mononuclear phagocyte system of the mouse, but only microglia express CSF-1R in the postnatal mouse brain (Erblich et al., 2011; Sasmono et al., 2003). To confirm cell-type specificity of cre expression driven by the c-fms (CSF-1R) promoter, CSF-1R-cre mice were crossed to the Rosa26-Td-Tomato mouse strain that expresses RFP in all cre-expressing cells. RFP expression was observed only in Iba-1-positive microglia in the adult mouse spinal cord, and RFP expression was absent in motor neurons and astrocytes (FIGS. S3A and S3B).

Figure 5A:
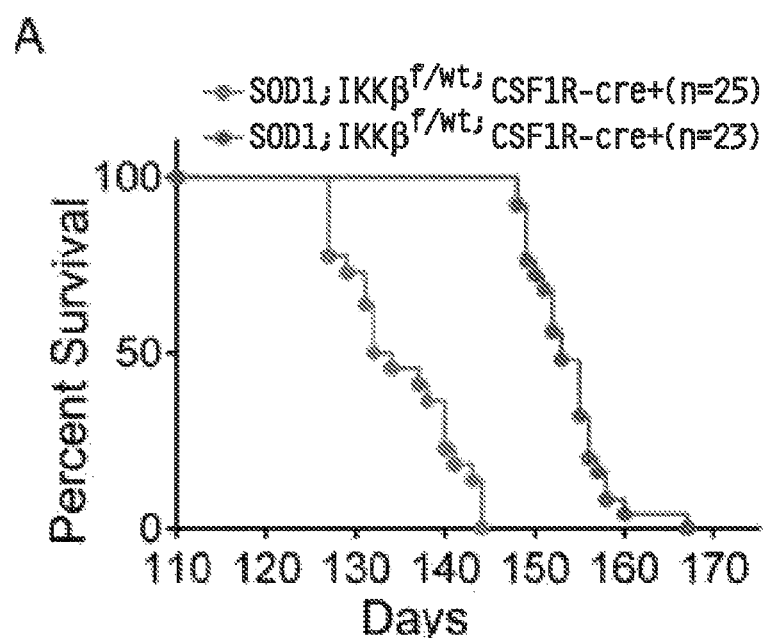

Wild-type and SOD1 CSF-1R-cre+ mice homozygous for IKKβf/f displayed serious immune dysfunction such as enlarged spleens, eye infections, and missing or very brittle teeth which have been previously reported in mice with myeloid cells devoid of NF-κB (Ruocco et al., 2005; Vallabhapurapu and Karin, 2009). These mice could not be maintained in the colony long enough to evaluate survival, thus, mice heterozygous for the flox'ed IKKβ allele (IKKβF/wt) were analyzed. To determine the efficiency of IKKβ knockdown in heterozygous mice, immunohistochemistry was performed for IKKβ in lumbar spinal cord sections from SOD1-G93A; IKKβf/wt; CSF-1R-cre+ and cre− mice. SOD1-G93A; IKKβf/wt; CSF-1R-cre+ showed a decrease in IKKβ staining compared to cre negative controls (FIG. S3C). To ensure knockdown was specific for IKKβ, we evaluated IKKγ, the regulatory subunit of the IKK signaling complex, and observed no difference between CSF-1R-cre+ and cre− mice (FIG. S3C). Reducing IKKβ, and thus NF-κB activation, resulted in a 20 day extension in median survival in SOD1-G93A; IKKβf/wt; CSF-1R-cre+ mice compared to cre− controls (133±days in cre− and 153±days in cre+) (FIG. 5A). While disease onset was not altered (102.8±1.1 days in cre− and 101.1±1.3 days in cre+), disease progression was extended by 47% in cre+ mice compared to cre− mice (34.8±1.4 days in cre− and 51.1.1±1.7 days in cre+) (FIGS. 5B and 5C). Video of age-matched littermates showed the SOD1-G93A; IKKβf/wt; CSF-1R-cre+ mouse was able to move around cage while SOD1-G93A; IKKβf/wt; CSF-1R-cre− littermate is at end-stage. To confirm the level of NF-κB inhibition that was achieved to slow down disease progression by 47%, lumbar spinal cord protein was examined for phospho-p65 from SOD1-G93A; IKKβf/wt; CSF-1R-cre+ or cre− mice at end-stage. Remarkably, phospho-p65 was reduced by 44% in SOD1-G93A; IKKβf/wt; CSF-1R-cre+ mice compared to cre− SOD1 controls (FIG. 5D), which expressed 7.5 fold more p65 than WT controls. Notably, NF-kB inhibition did not reduce the levels of mutant SOD1 in CSF-1R-cre+ mice compared to cre− SOD1 control mice (FIG. 5D).

Figure 5E:
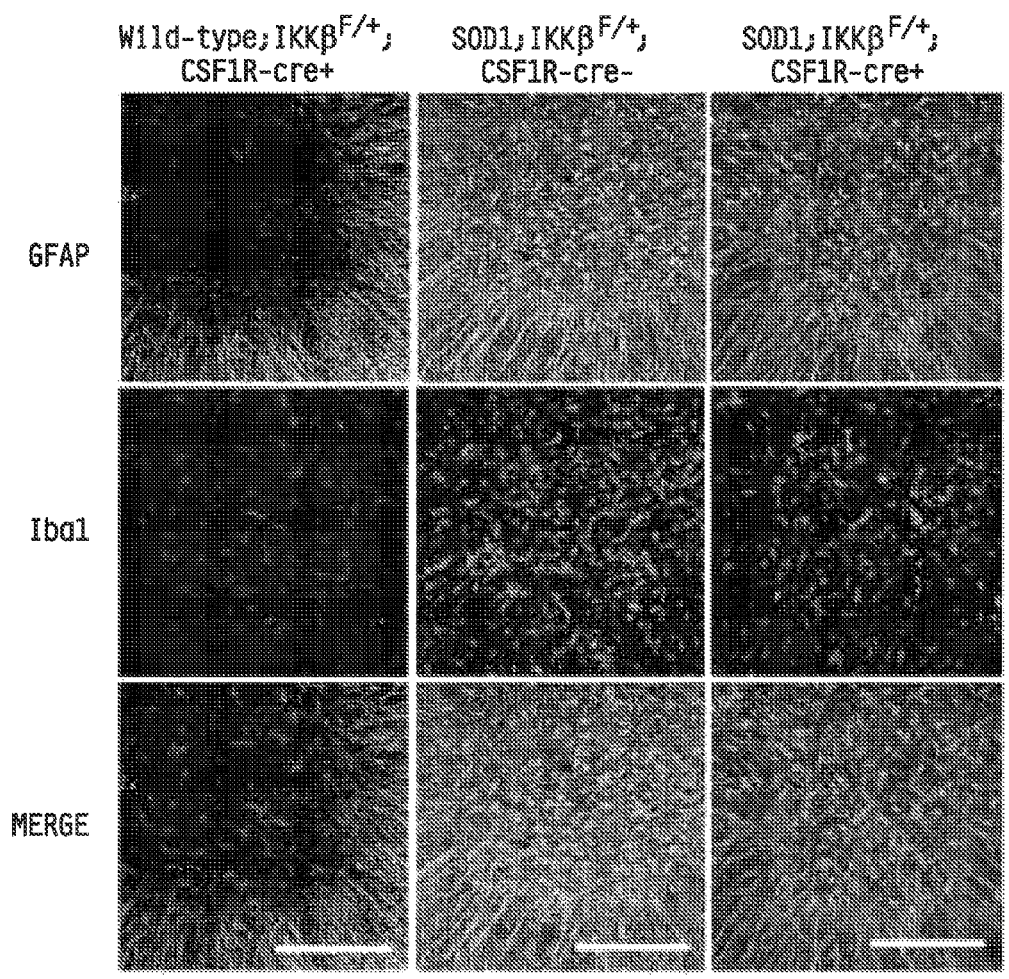
Figure 5F:
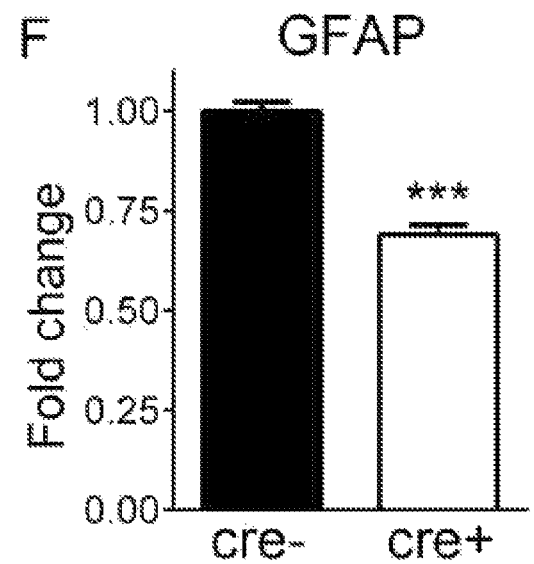
Figure 5G:
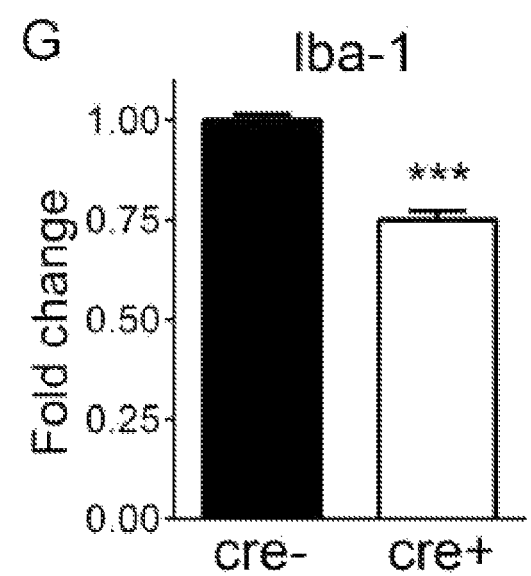

To determine the impact of NF-κB inhibition on astrogliosis and microgliosis, lumbar spinal cord sections were examined by immunohistochemistry for intensity of GFAP and Iba-1, respectively. No difference in gliosis could be detected between end-stage SOD1-G93A; IKKβf/wt; CSF-1R-cre+ and cre− mice. However, considering SOD1-G93A; IKKβf/wt; CSF-1R-cre+ have endured disease for an additional 3 weeks compared to controls, it is possible that differences in gliosis achieved earlier in disease are lost at end-stage. Indeed, the SOD1-G93A; IKKβf/wt; CSF-1R-cre+ mice were sacrificed at the same age as the cre−littermate control reached end-point, a significant decrease in Iba-1 (25%) and GFAP signal intensity (31%) was observed indicating microgliosis and astrogliosis are decreased in CSF-1R-cre+ mice compared to age-matched controls (FIGS. 5E, 5F, and 5G).

EXAMPLE 21

Figure 6A:
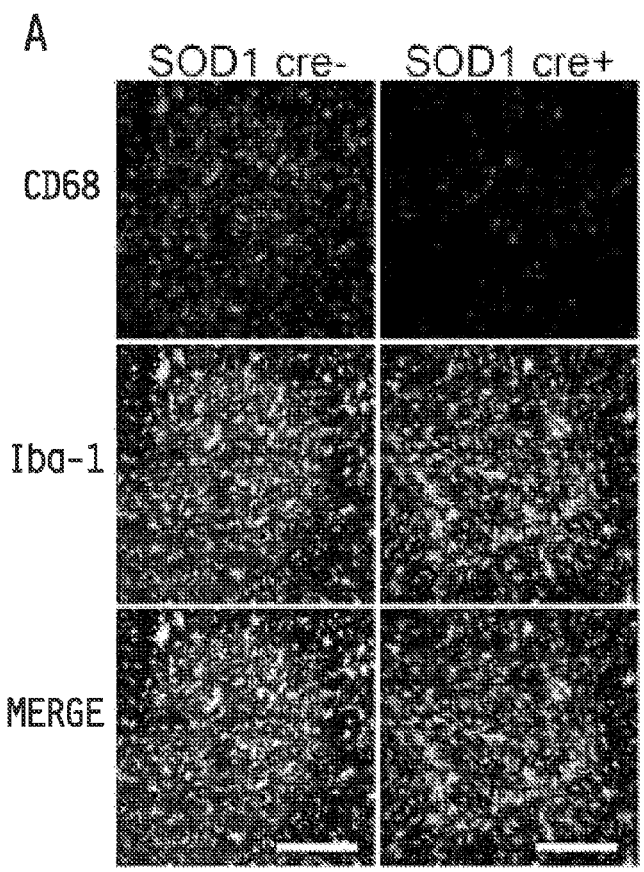
Figure 6B:
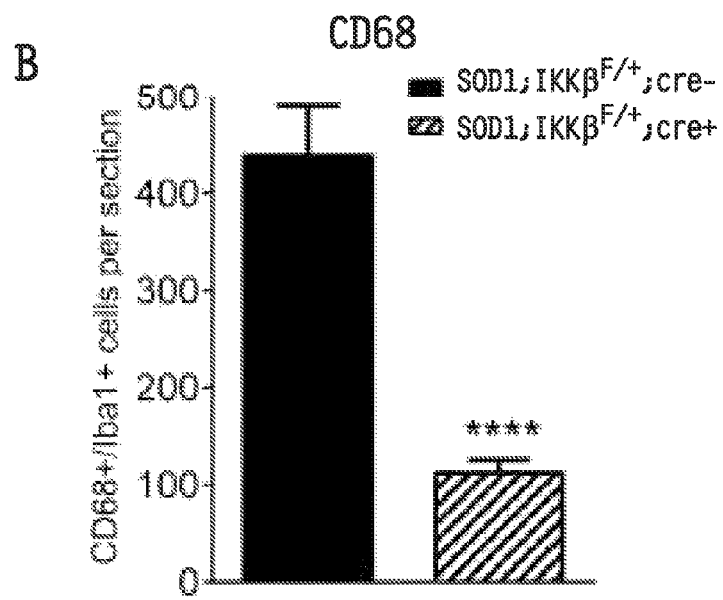
Figure 6C:
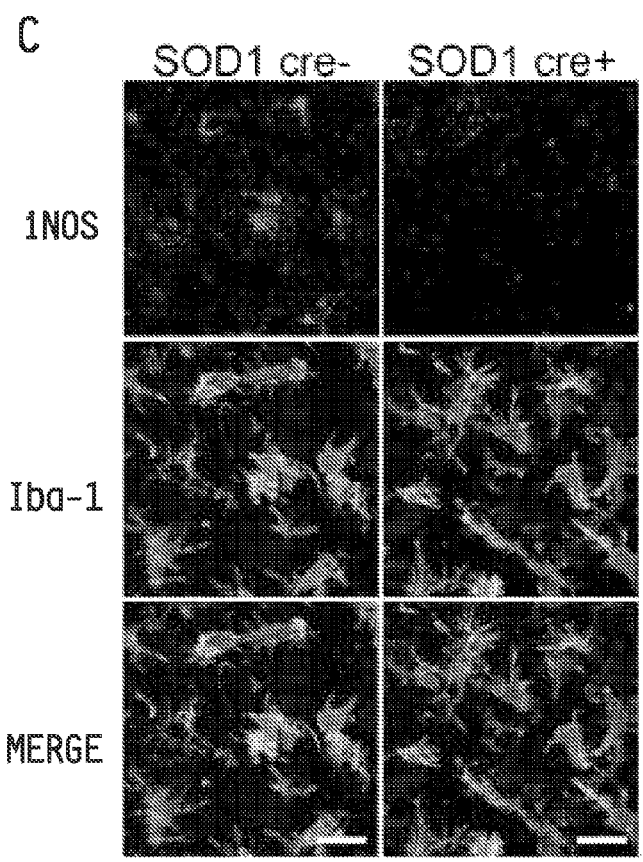
Figure 6D:
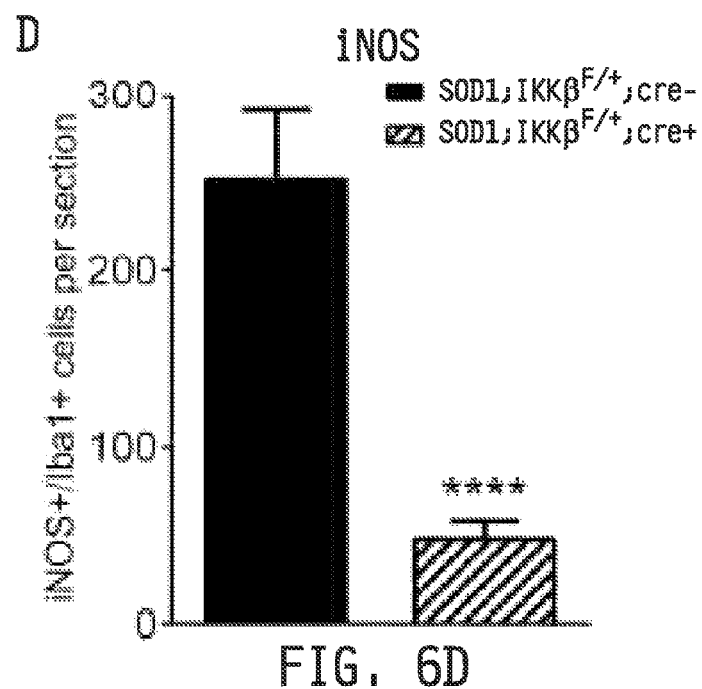
Figure 6E:
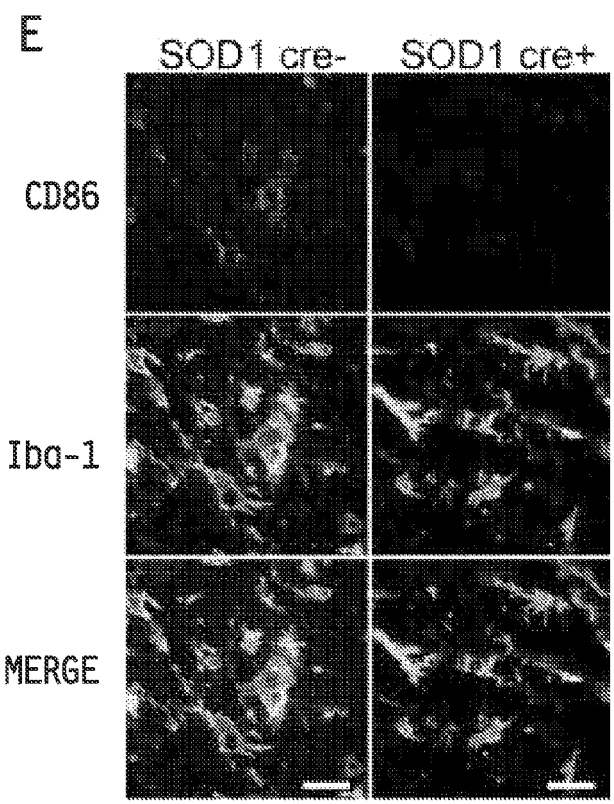
Figure 6F:
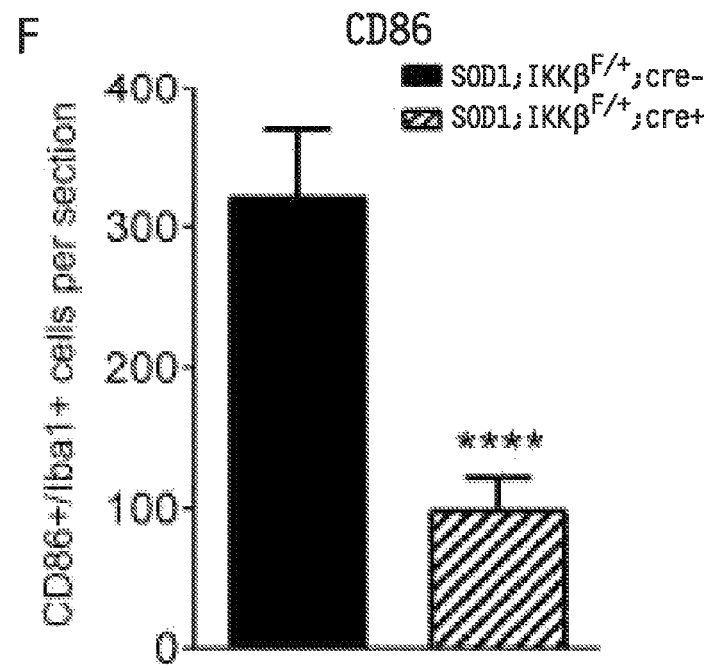

NF-κB Regulates SOD1-G93A Microglial Conversion to a Pro-Inflammatory, Neurotoxic Phenotype It was considered that the survival increase observed in SOD1-G93A; IKKβf/wt; CSF-1R-cre+ might be due to a dampened pro-inflammatory microglial response, so microglia were characterized for known markers of microglial activation such as CD68, iNOS, and CD86 (Kigerl et al., 2009). As disease progresses, it has been observed that SOD1-G93A mice exhibit a robust induction in CD68-positive microglia that is greatest at end-stage (data not shown) (Beers et al., 2011b). A marked reduction in the number of CD68 positive microglia in SOD1-G93A; IKKβf/wt; CSF-1R-cre+ mice compared to SOD1 cre-negative controls was observed (FIG. 6A). Quantification of CD68+/Iba1+ cells in lumbar spinal cord sections revealed mice with microglial NF-κB inhibition averaged 112.4±4.7 cells compared to SOD1 cre− littermates with an average of 438.3±13.4 cells per section (FIG. 6B). The number of iNOS+/Iba1+ cells per section was also significantly reduced from 251.1±15.0 in SOD1 controls to 47.8±3.1 in mice with microglial NF-κB inhibition (FIG. 6C, 6D). Following the same trend, mice with microglial NF-κB inhibition showed substantial reduction of CD86+/Iba1+ cells (97.8±7.4 per section) compared to SOD1 controls (320.3±15.6 cells per section) (FIGS. 6E and 6F). No alterations in the M2 markers CD206, arginase, and CD204 were observed by immunohistochemistry.

EXAMPLE 22

NF-κB Activation Selectively in Microglia Induces Motor Neuron Death In Vitro

It was considered that if NF-κB activation is the mechanism by which SOD1-G93A microglia induce motor neuron death, constitutively activating NF-κB in wild-type microglia would be sufficient to induce motor neuron death. Microglia were isolated from Rosa26-StopFloxIKKβCA mice containing inducible constitutively active IKKβ (IKKβCA) upon expression of cre recombinase. Post-isolation, microglia from these mice were infected with an adenovirus expressing cre recombinase (Ad-cre) to induce transcription of constitutively active IKKβ (microglia termed IKKβCA) or Ad-RFP as control (microglia termed WT). After 12 hours in co-culture with WT or IKKβCA microglia, no difference was observed in motor neuron axon length or survival (FIG. 7A). After 72 hours in co-culture IKKβCA microglia induced a 50% statistical decrease in motor neuron survival compared to controls (FIG. 7A, 7B). Live-imaging showed IKKβCA microglia rapidly inducing motor neuron death. It was confirmed by ELISA that NF-κB activation resulted in a 1.7-fold greater phospho-p65/total p65 in IKKβCA microglia compared to wild-type (FIG. 7C). The efficiency was evaluated of NF-κB induction by measuring nitric oxide (NO) and TNF-α levels in the co-culture medium. TNF-α levels increased 2.3-fold in co-cultures with IKKβCA microglia compared to WT microglia, which is comparable to TNF-α induction by SOD1-G93A microglia and characteristic of activated microglia (FIG. S4A). Nitric oxide (NO) levels in IKKβCA microglia/motor neuron co-culture were 1.5 fold greater than wild-type (FIG. S4B). These data indicate that constitutive NF-κB activation in microglia is sufficient to induce motor neuron death independent of the SOD1-G93A mutation.

EXAMPLE 23

Figure 7F:
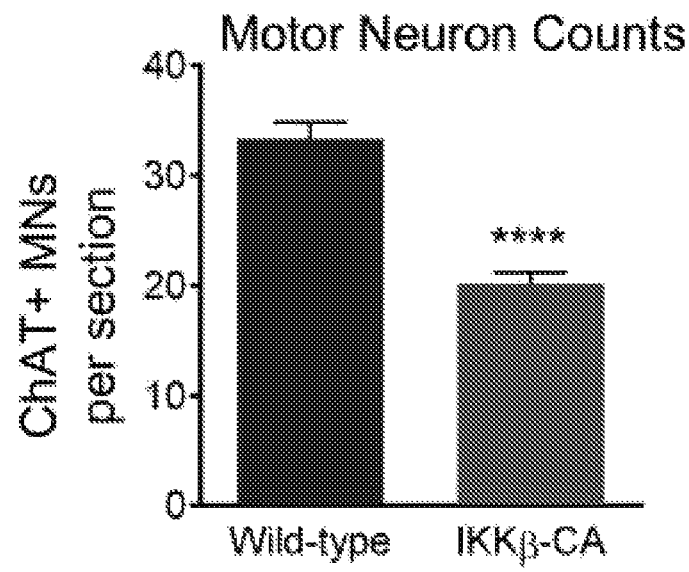
Figure 7G:
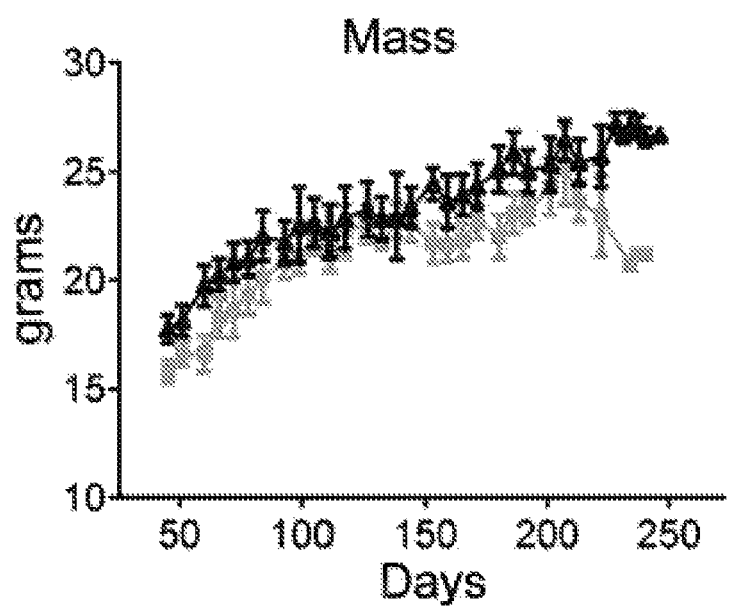
Figure 7H:
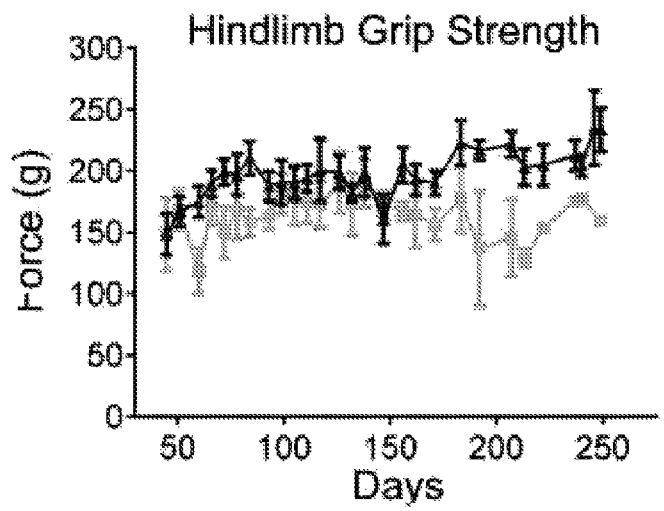
Figure 7I:
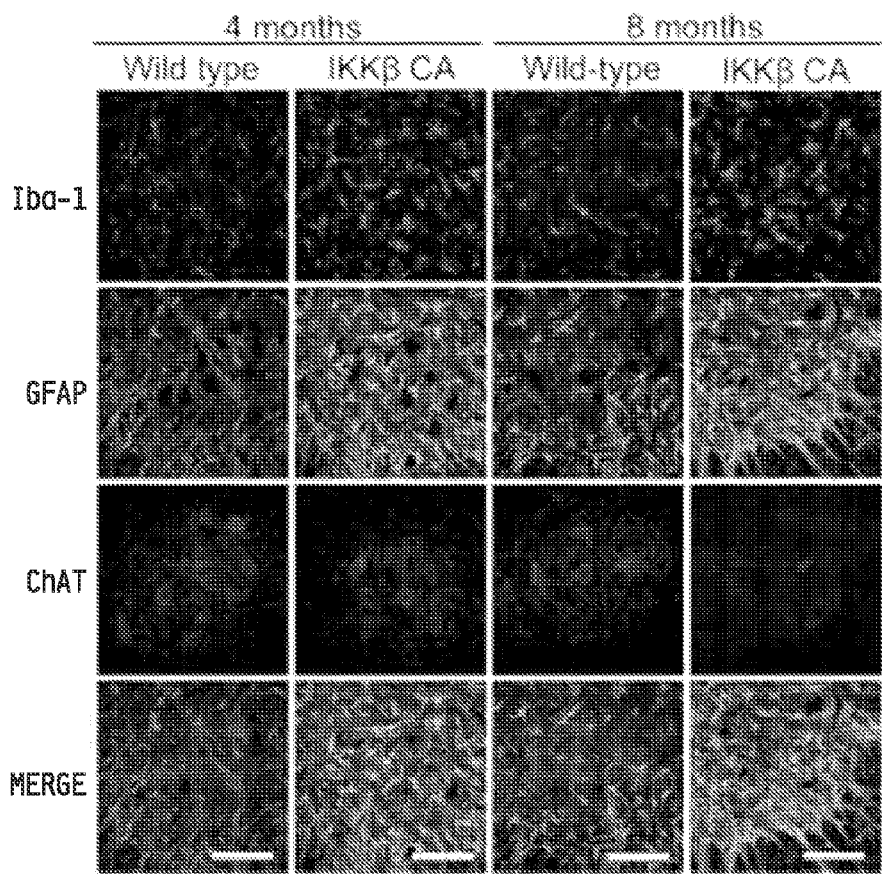

NF-κB Regulates Microglial Activation to a Pro-inflammatory, Neurotoxic Phenotype Constitutively active IKKβ(IKKβCA) was selectively expressed in myeloid cells in vivo, to induce an inflammatory state in wild-type microglia similar to that observed in ALS mice. Mice expressing CSF-1R-cre were crossed to Rosa26-Stop$^{Flox}$IKKβCA mice (termed IKKβCA). IKKβCA mice exhibited an 8.2 fold increase in phospho-p65 in lumbar spinal cord protein compared to cre-negative littermates (FIG. 7D). Immunohistochemistry of lumbar spinal cords of WT and IKKβCA littermates at 4 months and 8 months was performed (FIG. 7I). Enhanced microglial activation at 4 and 8 months in these mice also was associated with pronounced astrocytosis (FIG. 7E). By 8 months, a striking 40% decrease in ChAT+ MNs in the lumbar spinal cord was observed (FIG. 7F). MN loss in the spinal cord coincided with decreased mass and hind-limb grip strength in IKKβCA mice compared to wild-type littermates (FIGS. 7G and 7H). Thus, chronic activation of NF-κB signaling in myeloid cells created the pathological features of ALS in the spinal cord, i.e., gliosis and MN death. It is likely other neurons and brain regions are affected by microglial activation in IKKβCA mice.

To determine whether microglia in IKKβCA mice express activation markers, similar to those described above for activated (M1) microglia from SOD1-G93A mice, microglia from the IKKβCA and cre-negative littermates were analyzed for expression of CD68, iNOS, and CD86. A striking upregulation of CD68 and CD86 was observed in microglia from 4 month and 8 month-old IKKβCA mice (FIGS. S5A and S5B). Microglia from IKKβCA mice also differed drastically from those found in wild-type controls exhibiting a de-ramified morphology with shorter, thickened processes shown by Iba-1 staining. An increase in iNOS+ microglia was observed compared to wild-type controls at 8 months but not at 4 months in IKKβ CA mice (FIG. S5C). An increase in CD68 and CD86-positive microglia was observed in 8 month wild-type controls compared to 4 month-old controls which supports previous reports that microglial activation increases with aging (Norden and Godbout, 2013). These data suggest that chronic NF-κB activation induces an inflammatory (M1) microglia phenotype that causes MN death.

EXAMPLE 24

Reduction of Mutant SOD1 in Astrocytes in Combination with NF-κB Reduction in Microglia in SOD1-G93A Mice To evaluate the efficiency of reducing SOD1 in astrocytes in mice with suppressed NF-κB activation in microglia, SOD1; IKKβflox/wt; CSF1R-cre-positive and SOD1; IKKβflox/wt; CSF1R-cre-negative mice were injected intravenously with AAV9-SOD1-shRNA (shRNA sequence is SEQ ID NO: 1) at postnatal day 21. Along with the SOD1-shRNA, the AAV9 vector encodes green fluorescent protein (GFP) and allowed visualization of AAV9 transduction. Shown by immunohistochemistry, wide transduction of astrocytes in the lumbar spinal cord was observed. GFP co-localization with microglial marker Iba-1 was not observed, therefore it is unlikely microglia were transduced. By immunoblot analysis, mutant SOD1 levels were reduced by 60% in whole-lumbar spinal cord homogenate. Similarly, SOD1; IKKβflox/wt; CSF1R-cre+ mice exhibited a 50% reduction in phospho-p65 and IKKβ demonstrating reduction in NF-κB signaling. The cell types predominantly targeted with NF-κB suppression and mutant SOD1 reduction are listed in Table 3. SOD1; IKKβflox/wt; CSF1R-cre− mice that were not injected with virus were the control group. Only microglia were targeted in SOD1; IKKβflox/wt; CSF1R-cre+ mice. Astrocytes were the predominant cell targeted in mice injected at p21 with AAV9-SOD1-shRNA. However about 10% of motor neurons were transduced in the spinal cord with the p21 intravascular injection. Both microglia and astrocytes were targeted in SOD1; IKKβflox/wt; CSF1R-cre+ mice injected at p21 with AAV9-SOD1-shRNA.

Targeting both NF-κB activation in microglia and reducing SOD1 in astrocytes extended median survival to 168 days compared to 136 days in untreated, control mice (FIG. 9 A,B). This amounted to a 22.6% increase in median survival. Inhibiting NF-κB activation only in microglia increased median survival by 14% percent. Reducing mutant SOD1 in mainly astrocytes increased median survival by 16.8%. Due to the limited number of mice carrying both the SOD1-G93A transgene and CSF-1R-cre, both males and females were injected rather than only injecting AAV9-SOD1-shRNA in female mice.

While there was no difference in mean mass between CSF1R-cre− p21 injected mice and CSF1R-cre+ p21 injected mice, animal mass was sustained with survival in the cre+ littermates (FIG. 10A). When individual mice were evaluated for disease onset which is retrospectively defined as the age at which the mouse reaches peak weight, CSF1R-cre+; p21 injected mice reached onset on average at 126.4±2.1 days compared to 109.5±1.6 days of CSF1R-cre−; p21 injected mice. This is surprising since targeting microglia and astrocytes individually did not alter disease onset compared to untreated controls (FIG. 10B).

Disease progression was prolonged in SOD1-G93A; IKKβflox/wt; CSF1Rcre+ uninjected mice, CSF1R-cre− p21 injected mice and CSF1R-cre+ p21 injected mice (FIG. 10C). Thus, all conditions in which astrocytes and/or microglia were targeted resulted in an extension in disease progression.

Motor performance measured by accelerating rotarod (FIG. 11A), forelimb (FIG. 11B), and hind limb grip strength (FIG. 11C) was improved in all conditions in which astrocytes and/or microglia were targeted. SOD1-G93A; IKKβflox/wt; CSF1R-cre+ uninjected mice maintained rotarod performance, and increased forelimb and hind limb grip strength longer compared to CSF1R-cre− uninjected littermates (FIG. 11A,B,C). Similar to the late-stage differences in uninjected CSF1R-cre+ and CSF1R-cre− mice, p21 injected groups (CSF1R-cre+ and CSF1R-cre−) exhibited similar motor performance until the late-stage of disease, when CSF1R-cre+ mice maintained motor function longer with the increase in survival. These data suggest targeting microglia and astrocytes was beneficial in the SOD1-G93A mouse model.

TABLE 3

Cell types targeted in combinatorial approach.

SOD1-G93A; IKKβ$^{flox/wt}$

| AAV9 | | Cell types targeted | | |
|---|---|---|---|---|
| CSF1R-cre | SOD1-shRNA injection | Microglia | Astrocytes | Motor Neurons |
| − | uninjected | — | — | — |
| + | uninjected | 100% | — | — |
| − | p21 | — | 60% | 10% |
| + | p21 | 100% | 60% | 10% |
| − | p1 | — | 30% | 60% |
| + | p1 | 100% | 30% | 60% |

SOD1-G93A; IKKβflox/flox; CSF1R-cre+ and SOD1-G93A; IKKβflox/flox; CSF1R-cre− mice were generated and separated into 3 groups: Uninjected, injected at p21, and injected at p1. Uninjected CSF1R-cre− mice were the untreated group without any cell being targeted. CSF1R-cre+ mice had NF-κB signaling reduced in 100% of microglia. CSF1R-cre−; p21 injected mice, had full NF-κB activity in microglia and had reduced SOD1 levels of astrocytes. CSF1R-cre+; p21 injected mice, had reduced microglial NF-κB signaling and reduced levels of SOD1 in astrocytes. CSF1R-cre−; p1 injected mice had full NF-κB signaling and reduced levels of SOD1 in motor neurons and some astrocytes. CSF1R-cre+; p1 injected mice had reduced NF-κB signaling in microglia and reduced levels of SOD1 in motor neurons and some astrocytes.

EXAMPLE 25

Electrophoretic Mobility Shift Assays (EMSA) and Nuclear Western Blot

EMSA and supershift analyses were performed on whole spinal cord nuclear lysates as previously described (Dahlman & Guttridge, 2012). Nuclear westerns were performed using the same nuclear lysates as used for the EMSAs. The antibodies against p65, p60, c-Rel, and RelB are listed in Table 2.

What is claimed is:

1. A method for treating a patient with amyotrophic lateral sclerosis by decreasing the expression of NF-κB in the patient, the method comprising
administering to the patient a composition comprising an effective amount of a compound, and a pharmaceutically acceptable carrier therefor, wherein the compound decreases the expression of NF-κB in microglia of the patient, and wherein the compound is a nucleic acid; and
inhibiting motor neuron death in the patient.

2. The method of claim 1 wherein the nucleic acid is an shRNA.

3. The method of claim 2 wherein the nucleic acid comprises the sequence of SEQ ID NO: 1 or SEQ ID NO: 2.

4. The method of claim 3 wherein the nucleic acid comprises the sequence of SEQ ID NO:1.

5. The method of claim 3 wherein the nucleic acid comprises the sequence of SEQ ID NO:2.

6. The method of claim 1 wherein the amyotrophic lateral sclerosis is sporadic amyotrophic lateral sclerosis.

7. The method of claim 1 wherein administration of the composition increases the survival of the patient by 40 days or greater.

8. The method of claim 1 wherein the patient has a mutation in a superoxide dismutase 1 gene.

9. The method of claim 1 wherein the purity of the compound is at least 98 percent based on weight percent.

10. The method of claim 1 further comprising administering to the patient a composition comprising an effective amount of a compound that decreases the expression of superoxide dismutase 1 in astrocytes, motor neurons, neurons, and/or oligodendrocytes of the patient.

* * * * *

UNITED STATES PATENT AND TRADEMARK OFFICE
CERTIFICATE OF CORRECTION

PATENT NO. : 9,725,719 B2  
APPLICATION NO. : 15/034489  
DATED : August 8, 2017  
INVENTOR(S) : Brian K. Kaspar and Ashley E. Frakes Page 1 of 1

It is certified that error appears in the above-identified patent and that said Letters Patent is hereby corrected as shown below:

In the Specification

Column 1 Lines 18-20 replace with the following clause:
"This invention was made with Government support under NS064492 and NS077984 awarded by the National Institutes of Health. The Government has certain rights in the invention."

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
catggattcc atgttcatga                                                    20
```

<210> SEQ ID NO 2
<211> LENGTH: 942
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
atgtttcagc cggcgggcca tgccaggat tgggcgatgg aaggcccgcg cgatggcctg    60
aaaaaagaac gcctggtgga tgatcgccat gatgcgggcc tggatgcgat gaaagatgaa   120
gaatatgaac agatggtgaa agaactgcgc gaaattcgcc tgcagccgca ggaagcgccg   180
ctggcggcgg aaccgtggaa acagcagctg accgaagatg gcgatagctt tctgcatctg   240
gcgattattc atgaagaaaa accgctgacc atggaagtga ttggccaggt gaaaggcgat   300
ctggcgtttc tgaactttca gaacaacctg cagcagaccc cgctgcatct ggcggtgatt   360
accaaccagc cgggcattgc ggaagcgctg ctgaaagcgg gctgcgatcc ggaactgcgc   420
gattttcgcg gcaacacccc gctgcatctg gcgtgcgaac agggctgcct ggcgagcgtg   480
gcggtgctga cccagacctg caccccgcag catctgcata gcgtgctgca ggcgaccaac   540
tataacggcc atacctgcct gcatctggcg agcattcatg gctatctggc gattgtggaa   600
catctggtga ccctgggcgc ggatgtgaac gcgcaggaac cgtgcaacgg ccgcaccgcg   660
ctgcatctgg cggtggatct gcagaacccg gatctggtga gcctgctgct gaaatgcggc   720
gcggatgtga accgcgtgac ctatcagggc tatagcccgt atcagctgac ctggggccgc   780
ccgagcaccc gcattcagca gcagctgggc cagctgaccc tggaaaacct gcagatgctg   840
ccggaaagcg aagatgaaga aagctatgat accgaaagcg aatttaccga agatgaactg   900
ccgtatgatg attgcgtgtt tggcggccag cgcctgaccc tg                      942
```

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

```
catcagccct aatccatctg a                                              21
```

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
cgcgactaac aatcaaagtg a                                              21
```

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 5
ctaggccaca gaattgaaag atct                                           24

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtaggtggaa attctagcat catcc                                          25

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtcatttcca cagccctgtg a                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccttgtccta tagaagcaca a                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cagggccttc tccacaccag c                                              21

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctggctgtga agaccatc                                                  18

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 11
ggacatgttc agggatcgcc aggcg                                          25

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cgacgatgaa agcatgttta gctg                                           24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gagctgaagg gcatcgactt caag                                           24

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggactgggtg ctcaggtagt gg                                             22

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tcaggcccac ctagtcagat                                                20

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aaagcggtct gaggaggaa                                                 19

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 17
ctgttcctgt acggcatgg                                                    19

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggcattaaag cagcgtatcc                                                   20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aagggagctg cagtggagta                                                   20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ccgaaaatct gtgggaagtc                                                   20

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
ctgcatctgg ttcttgcaaa acacca                                            26

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cacgtgggct ccagcatt                                                     18

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 23
tcaccagtca tttctgcctt tg                                          22

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gggaagctgt tgtcccaag                                              19

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25 caagggagg taaaagagag c                                            21

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
ccaatggtcg ggcactgctc aa                                          22